United States Patent [19]

Aloup et al.

[11] Patent Number: 5,789,406
[45] Date of Patent: Aug. 4, 1998

[54] INDENO[1,2-E]PYRAZINE-4-ONES, THEIR PREPARATION AND THE MEDICAMENTS CONTAINING THEM

[75] Inventors: Jean-Claude Aloup, Villeneuve le Roi; François Audiau, Charenton le Pont; Michel Barreau, Montgeron; Dominique Damour, Orly; Arielle Genevois-Borella, Thiais; Patrick Jimonet, Villepreux; Serge Mignani, Chatenay-Malabry; Yves Ribeill, Villemoisson Sur Orge, all of France

[73] Assignee: Rhone-Poulenc Rorer S.A., Antony Cedex, France

[21] Appl. No.: 714,163

[22] PCT Filed: Mar. 23, 1995

[86] PCT No.: PCT/FR95/00357

§ 371 Date: Sep. 27, 1996

§ 102(e) Date: Sep. 27, 1996

[87] PCT Pub. No.: WO95/26349

PCT Pub. Date: Oct. 5, 1995

[30] Foreign Application Priority Data

Mar. 28, 1994 [FR] France ................... 94 03581

[51] Int. Cl.$^6$ ................... C02D 487/04; A61K 31/495
[52] U.S. Cl. ................... 514/233.2; 514/250; 544/115; 544/343
[58] Field of Search ................... 544/115, 343; 514/233.2, 250

[56] References Cited

U.S. PATENT DOCUMENTS

| | | | |
|---|---|---|---|
| 4,354,027 | 10/1982 | Loev et al. | 544/346 |
| 4,400,382 | 8/1983 | Brown et al. | 544/343 |
| 4,507,300 | 3/1985 | Brown et al. | 544/350 |
| 4,668,678 | 5/1987 | Brown et al. | 514/250 |
| 5,153,196 | 10/1992 | McQuaid et al. | 514/250 |
| 5,196,421 | 3/1993 | McQuaid et al. | 514/250 |

FOREIGN PATENT DOCUMENTS

| | | |
|---|---|---|
| 513530 | 12/1992 | European Pat. Off. . |
| 2696466 | 4/1994 | France . |
| 2707645 | 1/1995 | France . |
| WO9306103 | 4/1993 | WIPO . |
| 9400124 | 1/1994 | WIPO . |
| WO9400124 | 1/1994 | WIPO . |
| 94-07893 | 4/1994 | WIPO . |
| WO9418175 | 8/1994 | WIPO . |
| 95-02601 | 1/1995 | WIPO . |
| WO9502601 | 1/1995 | WIPO . |

OTHER PUBLICATIONS

Derwent Abstract of FR-A-2 696 466.
Derwent Abstract of FR-A-2 707 645.
McQuaid et al., "Synthesis and Excitatory Amino Acid Pharmacology of a Series of Heterocyclic-Fused Quinoxalinones and Quinazolinones", J. Med. Chem., 35(18):3319–3324 (1992).
Rashet et al., "A Facile Synthesis of Novel Triazoloquinoxalines and Triazinoquinozalinones [1]", J. Of Heterocyclic Chemistry, 27(3):691–694 (1990).

*Primary Examiner*—Mark L. Berch
*Attorney, Agent, or Firm*—Finnegan, Henderson, Farabow, Garrett & Dunner, L.L.P.

[57] ABSTRACT

The compounds of formula (I)

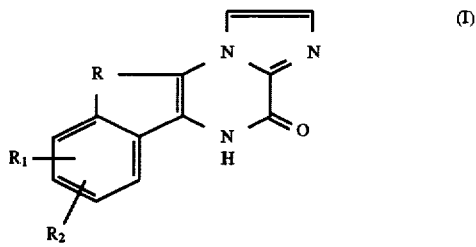

wherein R, $R_1$ and $R_2$ are defined in the disclosure, and salts thereof.

The compounds of formula (I) are non-competitive N-methyl-D-asparate (NMDA) receptor antagonists, particularly NMDA receptor glycine modulation site ligands, and are alpha-amino-3-hydroxy-5-methyl-4-isoxazolepropionic acid (AMPA) receptor antagonists, this receptor is also known as the quisqualate receptor.

9 Claims, No Drawings

INDENO[1,2-E]PYRAZINE-4-ONES, THEIR PREPARATION AND THE MEDICAMENTS CONTAINING THEM

The present invention relates to compounds of formula:

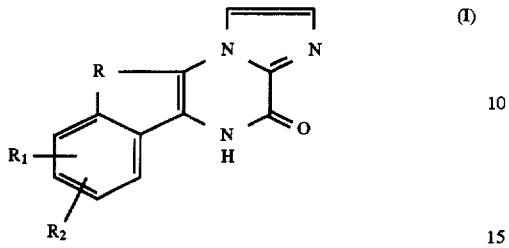

(I)

to their salts, to their preparation and to the medicaments containing them.

In the formula (I),

R represents an oxygen, sulphur or nitrogen atom, in which the nitrogen is substituted by an alkyl radical, or a radical C=$R_3$, C($R_4$)$R_5$ or CH—$R_6$, $R_1$ represents a hydroxyl, polyfluoroalkoxy, carboxyl, alkoxycarbonyl, —NH—CHO, —NH—CO—N(alk)Ar, in which Ar is optionally substituted by one or a number of substituents chosen from halogen atoms and alkyl, alkoxy, nitro, amino, hydroxyl, -alk-$NH_2$, —COO$R_{21}$, cyano and -alk-COO$R_{21}$ radicals, —N(alk)-CO—$NR_8R_9$, —N(alk-Ar)—CO—$NR_8R_9$, —NH—CO—$NR_9R_{12}$, —NH—CS—$NR_8R_9$, —N(alk)-CS—$NR_8R_9$, —NH—CO—$R_{10}$, —NH—CS—$R_{20}$, —NH—C(=$NR_{21}$)—$NR_7R_9$, —N(alk)-C(=$NR_{21}$)—$NR_7R_9$, —NH—$SO_2$—$NR_7R_9$, —N(alk)-$SO_2$—$NR_7R_9$, —CO—$NR_7R_9$, —NH—$SO_2$—$CF_3$, —NH—$SO_2$-alk, —$NR_9R_{11}$, —S(O)$_m$-alk-Ar, —$SO_2$—$NR_7R_9$, 2-oxo-1-imidazolidinyl, in which the 3-position is optionally substituted by an alkyl radical, or 2-oxo-1-perhydropyrimidinyl, in which the 3-position is optionally substituted by an alkyl radical, radical, $R_2$ represents a hydrogen or halogen atom or an alkyl, alkoxy, amino, —NH—CO—NH—Ar, —N=CH—N(alk)alk', nitro, cyano, phenyl, imidazolyl, acylamino, $SO_3H$, hydroxyl, polyfluoroalkoxy, carboxyl, alkoxycarbonyl, —NH—CHO, —NH—CO—N(alk)Ar, in which Ar is optionally substituted by one or a number of substituents chosen from halogen atoms and alkyl, alkoxy, nitro, amino, hydroxyl, -alk-$NH_2$, —COO$R_{21}$, cyano and -alk-COO$R_{21}$ radicals, —N(alk)-CO—$NR_8R_9$, —N(alk-Ar)—CO—$NR_8R_9$, —NH—CO—$NR_9R_{12}$, —NH—CS—$NR_8R_9$, —N(alk)-CS—$NR_8R_9$, —NH—CO—$R_{10}$, —NH—CS—$R_{20}$, —NH—C(=$NR_{21}$)—$NR_7R_9$, —N(alk)-C(=$NR_{21}$)—$NR_7R_9$, —NH—$SO_2$—$NR_7R_9$, —N(alk)-$SO_2$—$NR_7R_9$, —CO—$NR_7R_9$, —NH—$SO_2$—$CF_3$, —NH—$SO_2$-alk, —$NR_9R_{11}$, —S(O)$_m$-alk-Ar, —$SO_2$—$NR_7R_9$, 2-oxo-1-imidazolidinyl, in which the 3-position is optionally substituted by an alkyl radical, or 2-oxo-1-perhydropyrimidinyl, in which the 3-position is optionally substituted by an alkyl radical, radical, $R_3$ represents an oxygen atom or an NOR, NO-alk-COOX or CH—$R_{13}$ radical, $R_4$ represents an alkyl, -alk-Het or -alk-Ar radical, $R_5$ represents an alkyl (1–11 C in a straight or branched chain), -alk-Het or -alk-Ar radical, or else $R_4$ and $R_5$, together with the carbon atom to which they are attached, form a cycloalkyl radical, $R_6$ represents a hydrogen atom radical or a hydroxyl, alkyl (1–11 C in a straight or branched chain), —$NR_{14}R_{15}$, -alk-OH, -alk-$NR_{14}R_{15}$, -alk-Ar or -alk-Het radical, $R_7$ represents a hydrogen atom or an alkyl radical, $R_8$ represents a hydrogen atom or an alkyl, alk-COO$R_{21}$, -alk-Het", -alk-$NR_9R_7$, phenylalkyl, in which the phenyl ring is optionally substituted by one or a number of substituents chosen from halogen atoms and alkyl, alkoxy, nitro, amino, hydroxyl, -alk-$NH_2$, —COO$R_{21}$, cyano and -alk-COO$R_{21}$ radicals, phenyl, optionally substituted by one or a number of substituents chosen from halogen atoms and alkyl, alkoxy, nitro, amino, hydroxyl, -alk-$NH_{21}$, —COO$R_{21}$ cyano and -alk-COO$R_{21}$ radicals, or -Het" radical, $R_9$ represents a hydrogen atom or an alkyl radical, $R_{10}$ represents an alkyl (5–9 C in a straight or branched chain), alkoxy, -alk-COO$R_{21}$, -alk-Het", -alk-$NR_9R_7$, phenylalkyl, in which the phenyl ring is optionally substituted by one or a number of substituents chosen from halogen atoms and alkyl, alkoxy, nitro, amino, hydroxyl, -alk-$NH_2$, —COO$R_{21}$ cyano and -alk-COO$R_{21}$ radicals, phenyl, optionally substituted by one or a number of substituents chosen from halogen atoms and alkyl, alkoxy, nitro, amino, hydroxyl, -alk-$NH_2$, —COO$R_{21}$, cyano and -alk-COO$R_{21}$ radicals, or -Het" radical, $R_{11}$ represents an alkyl or Het" radical, $R_{12}$ represents a hydrogen atom or an alkyl, -alk-COO$R_{21}$, -alk-Het", -alk-$NR_9R_7$, phenylalkyl, in which the phenyl ring is optionally substituted by one or a number of substituents chosen from halogen atoms and alkyl, alkoxy, nitro, amino, hydroxyl, -alk-$NH_2$, —COO$R_{21}$, cyano and -alk-COO$R_{21}$ radicals, phenyl, substituted by one or a number of substituents chosen from halogen atoms and alkyl, alkoxy, nitro, amino, hydroxyl, -alk-$NH_2$, —COO$R_{21}$ cyano and -alk-COO$R_{21}$ radicals, or -Het" radical, $R_{13}$ represents a hydroxyl, alkyl, phenyl, -alk-Ar, -alk-Het, —$NR_{16}R_{17}$ or -Het radical, $R_{14}$ and $R_{15}$, which are identical or different, each represent an alkyl radical or else $R_{14}$ represents a hydrogen atom and $R_{15}$ represents a hydrogen atom or an alkyl, —COR$_{18}$, —CSR$_{19}$ or —$SO_2R_{20}$ radical, $R_{16}$ and $R_{17}$, which are identical or different, each represent an alkyl or cycloalkyl radical, $R_{18}$ represents an alkyl, cycloalkyl, phenyl, —COO-alk, —$CH_2$—COO$R_{21}$, —$CH_2$—$NH_2$, —NH-alk, —$NH_2$, —NH—Ar or —NH—Het radical, $R_{19}$ represents an —NH-alk, —NH—Ar, —$NH_2$ or —NH—Het radical, $R_{20}$ represents an alkyl or phenyl radical, $R_{21}$ represents a hydrogen atom or an alkyl radical, X represents a hydrogen atom or an alkyl radical, alk represents an alkyl or alkylene radical, alk' represents an alkyl radical, m is equal to 0, 1 or 2, Ar represents a phenyl radical, Het represents a saturated or unsaturated, mono- or polycyclic heterocycle containing 4 to 9 carbon atoms and one or a number of heteroatoms chosen from O, S and N, Het" represents a saturated or unsaturated, mono- or polycyclic heterocycle containing 1 to 9 carbon atoms and one or a number of heteroatoms chosen from O, S and N, the heterocycle optionally being substituted by one or a number of alkyl, phenyl or phenylalkyl radicals.

Except when otherwise mentioned, in the preceding and following definitions, the alkyl and alkoxy radicals and portions contain 1 to 6 carbon atoms in a straight or branched chain, the acyl portions contain 2 to 4 carbon atoms, the cycloalkyl radicals contain 3 to 6 carbon atoms and the halogen atoms are chosen from fluorine, chlorine, bromine and iodine.

Het preferably represents a pyridyl, furyl or pyrimidinyl ring.

Het" preferably represents a furyl, pyridyl, pyrimidinyl, thiazolinyl, pyrazinyl, thiazolyl, triazolyl, tetrazolyl, imidazolinyl, morpholinyl, imidazolyl, pyrrolyl, pyrrolidinyl, azetidinyl, piperazinyl, piperidinyl, thenyl, oxazolyl or oxazolinyl ring, these rings optionally being substituted by one or a number of alkyl, phenyl or phenylalkyl radicals.

The polyfluoroalkoxy radicals are preferably trifluoromethoxy radicals.

The compounds of formula (I) in which $R_2$ represents an N=CH—N(alk)alk' radical and/or $R_3$ represents an NOH, NO-alk-COOX or CH—$R_{13}$ radical exhibit isomeric forms (E and Z). These isomers and their mixtures form part of the invention.

The enantiomers and diastereoisomers of the compounds of formula (I) in which R represents a $C(R_4)R_5$, in which $R_4$ is other than $R_5$, or CH—$R_6$ radical also form part of the invention.

The compounds of formula (I) in which R represents an oxygen atom can be obtained by dealkylation, dehydration and desalification of the derivatives of formula:

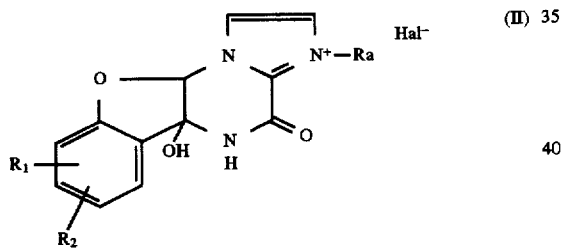

in which $R_1$ and $R_2$ have the same meanings as in the formula (I), Ra represents an alkyl radical and Hal represents a halogen atom. Hal preferably represents a bromine atom.

This reaction is generally carried out in the presence of imidazole, by heating at a temperature of between 100° and 200° C.

The derivatives of formula (II) can be obtained by reacting a 1-alkyl-1H-imidazole-2-carboxamide with a derivative of formula:

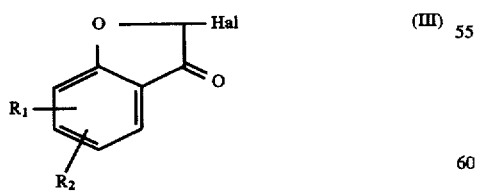

in which $R_1$ and $R_2$ have the same meanings as in the formula (I) and Hal represents a halogen atom. Hal preferably represents a bromine atom.

This reaction is generally carried out in an inert solvent, such as acetonitrile, at the boiling temperature of the reaction mixture.

The 1-alkyl-1H-imidazole-2-carboxamides can be obtained by application or adaptation of the method described by D. D. Davey, J. Org. Chem., 52, 4379 (1987).

The derivatives of formula (III) can be obtained by halogenation of the corresponding 3-coumaranones, by means of a halogenating agent, in an inert solvent, such as a chlorinated solvent (methylene chloride or chloroform, for example), at a temperature in the region of −15° C. Bromine or chlorine is preferably used.

The 3-coumaranones are commercially available or can be obtained by application or adaptation of the methods described by A. R. Deshpande et al., Synth. Commun., 20 (6), 809 (1990) and G. Schenk et al., Tetrahedron Lett., (19), 2375 (1968).

The compounds of formula (I) in which R represents a sulphur atom can be prepared by cyclization of a derivative of formula

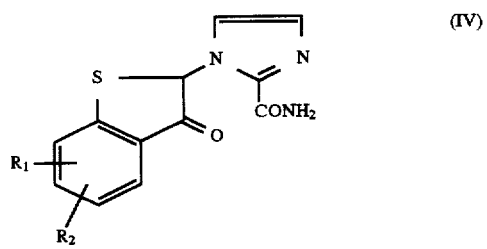

in which $R_1$ and $R_2$ have the same meanings as in the formula (I).

This cyclization is generally carried out by means of an acid such as hydrochloric acid in aqueous solution, at a temperature in the region of 20° C.

The derivatives of formula (IV) can be obtained by reacting ammonia with a derivative of formula:

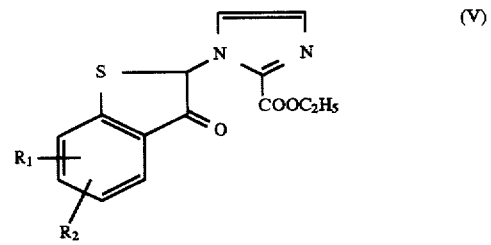

in which $R_1$ and $R_2$ have the same meanings as in the formula (I).

This reaction is generally carried out in an inert solvent, such as an alcohol, at a temperature of between 20° C. and the boiling temperature of the reaction mixture.

The derivatives of formula (V) can be obtained by condensation of ethyl imidazole-2-carboxylate with a derivative of formula:

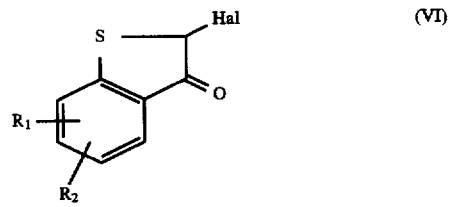

in which $R_1$ and $R_2$ have the same meanings as in the formula (I) and Hal represents a halogen atom and preferably a bromine atom.

This reaction is carried out in an inert solvent, such as an alcohol (methanol or ethanol, for example), at the boiling temperature of the reaction mixture.

Ethyl imidazole-2-carboxylate can be obtained according to the method described in U.S. Pat. No. 3,600,399.

The derivatives of formula (VI) can be obtained by adaptation of the method described by Z. I.

Miroshnichenko and M. A. Al'perovich, J. Gen. Chem. USSR, 32, 1218 (1962).

The compounds of formula (I) in which R represents a nitrogen atom substituted by an alkyl radical can be prepared by alkylation of a derivative of formula:

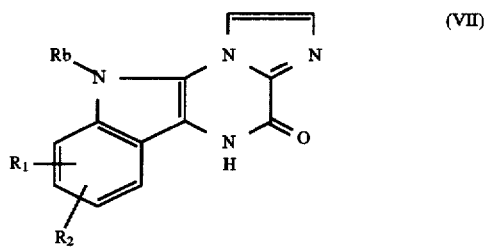

(VII)

in which $R_1$ and $R_2$ have the same meanings as in the formula (I) and Rb represents a hydrogen atom.

This reaction is preferably carried out by means of an alkyl halide, in the presence of an organic base, such as triethylamine, or an inorganic base, such as an alkali metal hydroxide (sodium hydroxide or potassium hydroxide, for example) or an alkali metal carbonate (sodium carbonate, for example), optionally in the presence of tetrabutylammonium bromide, in an inert solvent such as dimethyl sulphoxide, dimethylformamide or pyridine, at a temperature of between 20° and 50° C.

The derivatives of formula (VII) in which Rb represents a hydrogen atom can be prepared by hydrolysis of a corresponding derivative of formula (VII) in which Rb represents an acyl radical.

This reaction is carried out in an inert solvent such as an amide (dimethylformamide, for example), water or a mixture of these solvents, at a temperature varying from 5° C. to the boiling temperature of the reaction mixture.

The derivatives of formula (VII) in which Rb represents an acyl radical can be obtained by cyclization, in the presence of ammonium acetate, of the derivatives of formula:

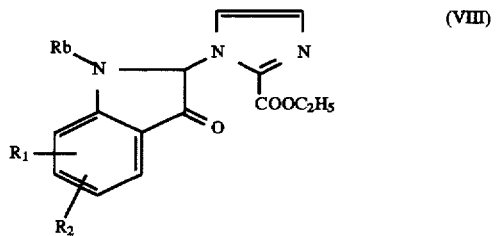

(VIII)

in which $R_1$ and $R_2$ have the same meanings as in the formula (I) and Rb represents an acyl radical.

This cyclization is preferably carried out in an inert solvent, such as acetic acid, at the boiling temperature of the reaction mixture.

The derivatives of formula (VIII) can be obtained by heating, at a temperature in the region of 120° C., ethyl imidazole-2-carboxylate and a derivative of formula:

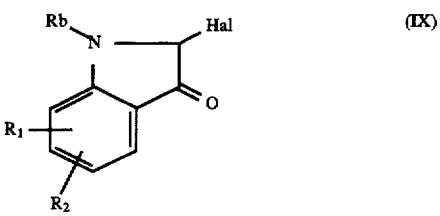

(IX)

in which $R_1$ and $R_2$ have the same meanings as in the formula (I), Rb represents an acyl radical and Hal represents a halogen atom and preferably a bromine atom.

The derivatives of formula (IX) can be obtained by adaptation of the method described by V. S. Velezheva et al., Khim. Farm. Zh., 24 (12), 46 (1990).

The compounds of formula (I) in which R represents a C=$R_3$ radical in which $R_3$ represents an oxygen atom can be prepared by hydrolysis of the corresponding compounds of formula (I) in which R represents a C=$R_3$ radical and $R_3$ represents an NOH radical.

This reaction is generally carried out by means of an acid, in aqueous medium, at the boiling temperature of the reaction mixture. Hydrochloric acid is preferably used as acid.

The compounds of formula (I) in which R represents a C=$R_3$ radical where $R_3$ represents an NOH radical can be prepared by reacting an alkyl nitrite with a corresponding compound of formula (I) in which R represents a CH—$R_6$ radical and $R_6$ represents a hydrogen atom.

This reaction is preferably carried out in an inert solvent, such as dimethyl sulphoxide, in the presence of an alkali metal hydride, such as sodium hydride, at a temperature in the region of 20° C. Isoamyl nitrite is preferably used.

The compounds of formula (I) in which R represents a C=$R_3$ radical and $R_3$ represents an NO-alk-COOX radical can be prepared by reacting a corresponding compound of formula (I), in which R represents a C=$R_3$ radical and $R_3$ represents an NOH radical, with a Hal-alk-COOX halide in which Hal represents a halogen atom and alk and X have the same meanings as in the formula (I).

This reaction is preferably carried out in the presence of a base, such as an alkali metal hydride such as sodium hydride, in an inert solvent, such as dimethyl sulphoxide, at a temperature in the region of 20° C.

The compounds of formula (I) in which R represents a C=$R_3$ radical and $R_3$ represents a CH—$R_{13}$ radical in which $R_{13}$ represents a hydroxyl radical can be prepared by hydrolysis of the corresponding compounds of formula (I) in which $R_{13}$ represents an —$NR_{16}R_{17}$ radical.

This reaction is preferably carried out by means of an acid, such as hydrochloric acid, in aqueous medium, at a temperature of between 20° and 40° C.

The compounds of formula (I) in which R represents a C=$R_3$ radical, $R_3$ represents a CH—$R_{13}$ radical and $R_{13}$ represents an —$NR_{16}R_{17}$ radical can be prepared by reacting a corresponding compound of formula (I), in which R represents a CH—$R_6$ radical and $R_6$ represents a hydrogen atom, with a derivative of formula

(X)

in which either Rc and Re, which are identical or different, each represent an —$NR_{16}R_{17}$ radical, $R_{16}$ and $R_{17}$ having the same meanings as in the formula (I), and Rd represents an alkoxy radical, such as tert-butoxy, or Rc, Rd and Re, which are identical, each represent an —$NR_{16}R_{17}$ radical, $R_{16}$ and $R_{17}$ having the same meanings as in the formula (I).

This reaction is generally carried out in an inert solvent, such as dimethylformamide, at a temperature of between 20° and 40° C.

The derivatives of formula (X) can be obtained by application or adaptation of the method described by H. Bredereck, Liebigs Ann. Chem., 762, 62 (1972).

The compounds of formula (I) in which R represents a C=$R_3$ radical, $R_3$ represents a CH—$R_{13}$ radical and $R_{13}$ represents an alkyl, phenyl, -alk-Het, -alk-Ar or -Het radical can be prepared by reacting a corresponding compound of formula (I), in which R represents a CH—$R_6$ radical and $R_6$ represents a hydrogen atom, with an aldehyde of formula OHC-Rf in which Rf represents an alkyl, phenyl, -alk-Het, -alk-Ar or —Het radical in which alk, Het and Ar have the same meanings as in the formula (I).

This reaction is generally carried out either in an inert solvent, such as dimethylformamide, 1,2-dimethoxyethane, a lower aliphatic alcohol (methanol or ethanol, for example) or a mixture of these solvents, in the presence of a base such as sodium hydroxide or potassium hydroxide or a strong organic base, such as 1,8-diazabicyclo[5,4,0]undec-7-ene, at a temperature of between 20° and 100° C., or in dimethyl sulphoxide, in the presence of an alkali metal hydride, such as sodium hydride, at a temperature in the region of 20° C., or in the presence of tetrabutylammonium bromide and of a base, such as an alkali metal hydroxide (sodium hydroxide or potassium hydroxide, for example), in dimethyl sulphoxide, at a temperature of between 20° C. and the boiling temperature of the reaction mixture, or in acetic acid or acetic anhydride, in the presence of ammonium acetate, at a temperature of between 20° C. and the boiling temperature of the reaction mixture.

The aldehydes OHC-Rf are commercially available or can be obtained (a) by oxidation of the corresponding alcohols HOH$_2$C-Rf (using $K_2Cr_2O_7$, in sulphuric medium; using $CrO_3$ in pyridine or $MnO_2$ in a chlorinated solvent (dichloromethane, for example), at a temperature in the region of 20° C., or using dimethyl sulphoxide and ClCO—COCl, by adaptation or application of the method described by D. Swern et al., J. Org. Chem., 44, 4148 (1979)); (b) by reduction of the corresponding carboxylic acids HOOC-Rf (using lithium aluminium hydride or $AlH_3$, in an inert solvent such as tetrahydrofuran, at a temperature of between 0° and 25° C.); (c) by reduction of the corresponding esters alkOOC-Rf (using diisobutylaluminium hydride, in an inert solvent, such as toluene, at a temperature of between −70° C. and 25° C., or lithium aluminium hydride, in an inert solvent, such as tetrahydrofuran, at a temperature of between 0° and 25° C.).

The corresponding alcohols HOH$_2$C-Rf in which Rf represents an -alk-Het or -alk-Ar radical are commercially available or can be obtained from the corresponding organometallic compounds by application or adaptation of the methods described by N. S. Narasimhan et al., Tetrahedron Lett., 22 (29), 2797 (1981); L. Estel et al., J. Het. Chem., 26, 105 (1989); N. S. Narasimhan et al., Synthesis, 957 (1983); N. Marsais et al., J. Heterocyclic Chem., 25, 81 (1988); H. W. Gshwend et al., Organic Reactions, 26, 1 (1976) and V. S. Snieckus, Chem. Rev., 90, 879 (1990). Preferably, the organolithium or organomagnesium derivative of the heterocycle or of benzene is reacted with formaldehyde, ethylene oxide or a Hal-alk-CH$_2$OP derivative where P is a protecting group (methyl ether, tetrahydropyranyl ether, benzyl ether or triethylsilyl ether, for example), Hal is a halogen atom and alk is an alkyl radical, followed by release of the alcohol functional group by application or adaptation of the methods described by W. Greene et al., Protecting Groups in Organic Synthesis, second edition, 1991, John Wiley and Sons.

The corresponding alcohols HOH$_2$C-Rf in which Rf represents an -alk-Het or -alk-Ar radical can also be obtained by reduction of the corresponding carboxylic acids or esters, by means of lithium aluminium hydride, in an inert solvent, such as tetrahydrofuran or diethyl ether, at the boiling temperature of the reaction mixture.

The corresponding alcohols HOH$_2$C-Rf in which Rf represents an -alk-Het radical can also be obtained by application or adaptation of the method described by J.Th. Meyer et al., Helv. Chem. Acta, 65, 1868 (1982) from Hal-alk (0–5C)-Het derivatives, in which Hal represents a halogen atom and alk and Het have the same meanings as in the formula (I), which are themselves obtained by reacting a halogenating agent (halogenated phosphorus derivative or thionyl chloride) with a corresponding HOH$_2$C-alk(0–5C)-Het derivative, optionally in an inert solvent, such as dichloromethane, at a temperature of between 20° and 40° C.

The corresponding carboxylic acids HOOC-Rf in which Rf represents a -Het, -alk-Het or -alk-Ar radical are commercially available or can be obtained from the corresponding heterocycles or from benzene by application or adaptation of the methods described by L. Estel et al., J. Heterocyclic Chem., 26, 105 (1989); N. S. Narasimhan et al., Synthesis, 957 (1983); A. Turck et al., Synthesis 881 (1988); A. J. Clarke et al., Tetrahedron Lett., 27, 2373 (1974); A. R. Katritzky et al., Org. Perp. Procedure Int., 20 (6), 585 (1988); N. Furukawa et al., Tetrahedron Let., 28 (47), 5845 (1987); H. W. Gschwend et al., Organic Reactions 26, 1 (1979) and V. Snieckus, Chem. Rev. 90, 879 (1990). Preferably, the corresponding organometallic derivative is prepared from the corresponding heterocycle or from benzene (organolithium or organomagnesium derivative, for example) and it is reacted either with $CO_2$ or with a Hal-alk-COOalk derivative in which Hal represents a halogen atom and alk an alkyl radical, followed by hydrolysis of the ester.

The Hal-alk-COOalk derivatives are commercially available or prepared by reacting Hal-alk-Hal, in which Hal represents a halogen atom and alk an alkyl radical, with an alkali metal cyanide, such as sodium cyanide or potassium cyanide, in a water/lower aliphatic alcohol mixture, at a temperature of between 0° C. and the boiling temperature of the reaction mixture, followed by reacting with an acid, such as hydrochloric acid, in the presence of a straight- or branched-chain $C_1$–$C_6$ aliphatic alcohol, at a temperature of between 0° C. and the boiling temperature of the reaction mixture.

The Hal-alk-Hal derivatives are commercially available or can be obtained from the corresponding dialcohols by application or adaptation of the methods described by C. Larock, "Comprehensive Organic Transformations", published by VHC, page 353 (1989).

The corresponding alkOOC-Rf esters are commercially available or can be obtained from the acids by reacting with an organic acid, such as hydrochloric acid or sulphuric acid, in a lower aliphatic alcohol, which is also used as esterification agent, at the boiling temperature of the reaction mixture.

The compounds of formula (I) in which R represents a C($R_4$)$R_5$ radical, $R_4$ represents an alkyl, -alk-Het or -alk-Ar radical and $R_5$ is identical to $R_4$ can be prepared by reacting a corresponding compound of formula (I), in which R represents a CH—$R_6$ radical and $R_6$ represents a hydrogen atom, with a halide of formula Hal-Rg in which Rg represents an alkyl, -alk-Het or -alk-Ar radical in which alk, Het and Ar have the same meanings as in the formula (I).

This reaction is preferably carried out in an inert solvent, such as dimethyl sulphoxide, dimethylformamide, tetrahydrofuran or dioxane, in the presence of a base, such as an alkali metal hydroxide (sodium hydroxide or potassium hydroxide, for example), optionally in the presence of tetrabutylammonium bromide, in dimethyl sulphoxide, or in the presence of an alkali metal hydride (sodium hydride, for example), at a temperature of between 20° C. and the boiling temperature of the reaction mixture.

The Hal-Rg derivatives are commercially available or can be prepared from the corresponding alcohols by application or adaptation of the methods described by R. C. Larock "Comprehensive Organic Transformations", published by VCH, page 353 (1989).

The compounds of formula (I) in which R represents a $C(R_4)R_5$ radical, $R_4$ represents an alkyl, -alk-Het or -alk-Ar radical and $R_5$ represents an alkyl (1–11C in a straight or branched chain), -alk-Het or -alk-Ar radical can be prepared by reacting a corresponding compound of formula (I), in which R represents a CH—$R_6$ radical and $R_6$ represents an alkyl, -alk-Het or -alk-Ar radical, with a halide of formula Hal-Rh in which Rh represents an alkyl (1–11C in a straight or branched chain), -alk-Het or -alk-Ar radical in which alk, Het and Ar have the same meanings as in the formula (I).

This reaction is preferably carried out in an inert solvent, such as dimethyl sulphoxide, dimethylformamide, tetrahydrofuran or dioxane, in the presence of a base, such as an alkali metal hydroxide (sodium hydroxide or potassium hydroxide, for example), optionally in the presence of tetrabutylammonium bromide, in dimethyl sulphoxide, or in the presence of an alkali metal hydride (sodium hydride, for example), at a temperature of between 20° C. and the boiling temperature of the reaction mixture.

The Hal-Rh halides are commercially available or can be prepared from the corresponding alcohols by adaptation of the methods described by R. C. Larock, "Comprehensive Organic Transformations", published by VCH, page 353 (1989).

The compounds of formula (I) in which R represents a $C(R_4)R_5$ radical and $R_4$ and $R_5$, with the carbon atom to which they are attached, form a cycloalkyl radical can be prepared by reacting a corresponding compound of formula (I), in which R represents a CH—$R_6$ radical and $R_6$ represents a hydrogen atom, with a derivative of formula Hal-alk-Hal in which Hal represents a halogen atom and alk represents an alkyl (2–5C) radical.

This reaction is preferably carried out in an inert solvent, such as dimethyl sulphoxide, dimethylformamide, tetrahydrofuran or dioxane, in the presence of a base, such an alkali metal hydroxide (sodium hydroxide or potassium hydroxide, for example), optionally in the presence of tetrabutylammonium bromide, in dimethyl sulphoxide, or in the presence of an alkali metal hydride (sodium hydride, for example), at a temperature of between 20° C. and the boiling temperature of the reaction mixture.

The Hal-alk-Hal derivatives are commercially available or can be prepared from the corresponding alcohols by adaptation of the methods described by K. C. Larock, "Comprehensive Organic Transformations", published by VCH, page 353 (1989).

The compounds of formula (I) in which R represents a CH—$R_6$ radical and $R_6$ represents a hydrogen atom can be prepared by dealkylation and desalification of the derivatives of formula:

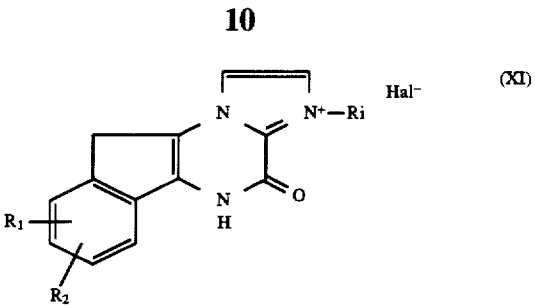

in which $R_1$ and $R_2$ have the same meanings as in the formula (I), Ri represents an alkyl radical and Hal represents a halogen atom and preferably a bromine atom.

This reaction is preferably carried out in the presence of imidazole, at a temperature of between 100° and 200° C. and in particular at 160° C.

The derivatives of formula (XI) can be obtained by reacting a 1-alkyl-1H-imidazole-2-carboxamide with a 2-haloindanone of formula:

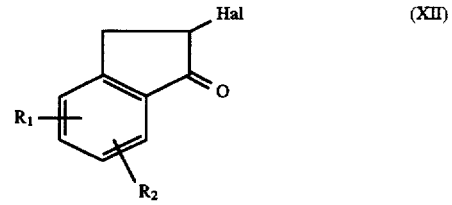

in which $R_1$ and $R_2$ have the same meanings as in the formula (I) and Hal represents a halogen atom and preferably a bromine atom.

This reaction is generally carried out in an inert solvent, such as dimethylformamide, at a temperature of between 50° and 150° C. and preferably at 115° C.

The derivatives of formula (XII) can be obtained by halogenation of the corresponding indanones by means of a halogenating agent, such as bromine or chlorine, in an inert solvent, such as a chlorinated solvent (methylene chloride or chloroform, for example), at a temperature of –15° C., or in acetic acid, at a temperature in the region of 20° C., or a copper halide, in dioxane, at a temperature in the region of 100° C., or by application or adaptation of the methods described by K. Mori, Agr. Biol. Chem., 27 (1), 22 (1963); J. Chakravarty, Indian J. Chem., 7 (3), 215 (1969), F. G. Holliman et al., J. Chem. Soc. 9 (1960), D. Mukhopadhya et al., J. Indian Chem. Soc., 47 (5), 450 (970) and in Patents DE 2,640,358 and EP 346,107.

The indanones can be obtained by application or adaptation of the methods described by M. Olivier et al., Bull. Soc. Chim. de France, 3092 (1973), R. Seka et al., Chem. Ber., 75B, 1730 (1942), J. J. Howbert et al., Synth. Commun., 20 (20), 3197 (1990), D. F. Biggs et al., J. Med. Chem., 19 (4), 472 (1976), C. K. Ingold et al., J. Chem. Soc., 1469 (1923), in Patents U.S. Pat. Nos. 4,263,319, 4,096,173, JP 80161237 and EP 314,400 and in the examples.

The compounds of formula (I) in which R represents a CH—$R_6$ radical and $R_6$ represents a hydrogen atom can also be prepared by cyclization, optionally in the presence of ammonium acetate, of a derivative of formula:

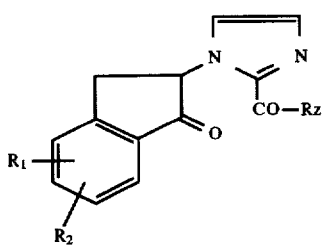 (XIII)

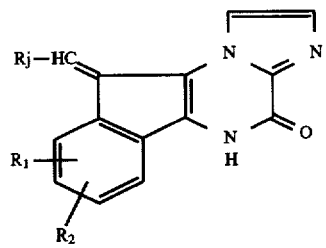 (XIV)

in which $R_1$ and $R_2$ have the same meanings as in the formula (I) and Rz represents an —$NH_2$ or -Oalk radical in which alk represents an alkyl radical.

This cyclization is carried out by means of an acid, such as acetic acid or hydrochloric acid, in aqueous medium or in an alcohol, such as ethanol or methanol, at the boiling temperature of the reaction mixture.

The derivatives of formula (XIII) in which Rz represents an —$NH_2$ radical can be obtained by reacting ammonia with a corresponding derivative of formula (XIII) in which Rz represents an -Oalk radical.

This reaction is generally carried out in an inert solvent, such as an alcohol, at a temperature of between 20° C. and the boiling temperature of the reaction mixture.

The derivatives of formula (XIII) in which Rz represents an -Oalk radical can be obtained by reacting a 2-haloindanone of formula (XII) with a 2-alkoxycarbonylimidazole.

This reaction is carried out either by fusion at a temperature of between 130° and 180° C., or in an inert solvent, such as dimethylformamide, in the presence of a base, such as an alkali metal hydride (sodium hydride, for example), at a temperature in the region of 20° C., or in an inert solvent, such as a chlorinated solvent such as chloroform, in the presence of a nitrogenous organic base (1,8-diazabicyclo[5, 4,0]-undec-7-ene, for example), at a temperature in the region of 20° C., or in an inert solvent, such as an alcohol (ethanol or propanol, for example), an aromatic solvent such as toluene, or a chlorinated solvent (chloroform, for example), optionally in the presence of sodium iodide, at the boiling temperature of the reaction mixture, or in acetone, in the presence of an alkali metal carbonate, at a temperature of between 20° C. and the boiling temperature of the reaction mixture.

The 2-alkoxycarbonylimidazoles can be obtained by application or adaptation of the method described in U.S. Pat. No. 3,600,399.

The compounds of formula (I) in which R represents a CH—$R_6$ radical in which $R_6$ represents a hydroxyl radical can be prepared by reduction of the corresponding compounds of formula (I) in which R represents a C=$R_3$ radical and $R_3$ represents an oxygen atom.

This reaction is preferably carried out in an inert solvent, such as an alcohol (methanol or ethanol, for example), in the presence of sodium borohydride, at a temperature of between 15° and 40° C.

The compounds of formula (I) in which R represents a CH—$R_6$ radical in which $R_6$ represents an alkyl (2–11C), -alk-Ar or -alk-Het radical can be prepared by hydrogenation of a derivative of formula:

in which $R_1$ and $R_2$ have the same meanings as in the formula (I) and Rj represents an alkyl, in a straight or branched chain containing 1 to 10 carbon atoms, phenyl, -alk(1–5C)-Ar, -alk(1–5C)-Het or Het radical in which Het and Ar have the same meanings as in the formula (I).

This reduction is generally carried out by means of hydrogen, under a pressure of 1 to 50 bar, in an inert solvent, such as dimethylformamide, acetic acid, ethyl acetate, an alcohol (methanol or ethanol, for example) or a mixture of these solvents, in the presence of a hydrogenation catalyst, such as palladium-on-charcoal, palladium hydroxide or palladium (N. Rico et al., Nouveau Journal de Chimie, 10, 1, 25 (1986)), at a temperature between 20° C. and 60° C., or by adaptation of the method described by L. M. Strawn et al., J. Med. Chem., 32, 2104 (1989), which consists in reducing the compound with hydroxylamine sulphate and $H_2NOSO_3H$ in water, at a pH of between 6 and 7, at a temperature of 10° C.

The derivatives of formula (XIV) in which Rj represents a straight- or branched-chain alkyl radical containing 7 to 10 carbon atoms can be prepared as described above for their homologues (compounds of formula (I) in which R represents a C=$R_3$ radical, $R_3$ represents a CH—$R_{13}$ radical and $R_{13}$ represents an alkyl radical).

The compounds of formula (I) in which R represents a CH—$R_6$ radical in which $R_6$ represents a methyl radical can be prepared by reduction of the corresponding compounds of formula (I) in which R represents a C=$R_3$ radical, $R_3$ represents a CH—$R_{13}$ radical and $R_{13}$ represents a hydroxyl or —$NR_{16}R_{17}$ radical.

This reduction is generally carried out by means of hydrogen, under a pressure of 1 to 50 bar, in an inert solvent, such as dimethylformamide, acetic acid, ethyl acetate, an alcohol (methanol or ethanol, for example) or a mixture of these solvents, in the presence of a hydrogenation catalyst, such as palladium-on-charcoal or palladium hydroxide, at a temperature of between 20° C. and 60° C.

The compounds of formula (I) in which R represents a CH—$R_6$ radical and $R_6$ represents an -alk(1C)-OH radical can be prepared by reduction of the corresponding compounds of formula (I) in which R represents a C=$R_3$ radical, $R_3$ represents a CH—$R_{13}$ radical and $R_{13}$ represents a hydroxyl radical.

This reduction is generally carried out using a reducing agent, such as sodium borohydride, in an inert solvent, such as an alcohol (methanol or ethanol, for example), at a temperature in the region of 20° C.

The compounds of formula (I) in which R represents a CH—$R_6$ radical and $R_6$ represents an -alk(2–6C)-OH radical can be prepared by reduction of the derivatives of formula (XIV) in which $R_1$ and $R_2$ have the same meanings as in the formula (I) and Rj represents an -alk(1–5C)—O—$CH_2$—Ar radical in which alk and Ar have the same meanings as in the formula (I).

This reduction is generally carried out by means of hydrogen, under a pressure of 1 to 50 bar, in an inert solvent, such as dimethylformamide, acetic acid, ethyl acetate, an alcohol (methanol or ethanol, for example) or a mixture of these solvents, in the presence of a hydrogenation catalyst, such as palladium-on-charcoal, palladium hydroxide or palladium (N. Rico et al., Nouveau Journal de Chimie, 10, 1, 25 (1986)), at a temperature of between 20° C. and 60° C., or by adaptation of the method described by L. M. Strawn et al., J. Med. Chem., 32, 2104 (1989), which consists in reducing the compound with hydroxylamine sulphate and $H_2NOSO_3H$ in water, at a pH of between 6 and 7, at a temperature of 10° C.

The derivatives of formula (XIV) in which Rj represents an -alk(1-5C)—O—$CH_2$—Ar radical can be obtained by reaction of a corresponding compound of formula (I), in which R represents a CH—$R_6$ radical and $R_6$ represents a hydrogen atom, with an OHC-alk(1-5C)—O—$CH_2$—Ar aldehyde.

This reaction is carried out under the same conditions as those mentioned above for the reaction of the compounds of formula (I) in which R represents a CH—$R_6$ radical and $R_6$ represents a hydrogen atom with the aldehydes of formula OHC-Rf.

The OHC-alk(1-5C)—O—$CH_2$—Ar derivatives can be obtained by application or adaptation of the methods described by P. Schorigin et al., Chem. Ber., 68, 838 (1935) or by A. Gaiffe et al., C. R. Acad. Sc. Paris, série C, 266, 1379 (1968).

The compounds of formula (I) in which R represents a CH—$R_6$ radical in which $R_6$ represents an —$NR_{14}R_{15}$ or -alk-$NR_{14}R_{15}$ radical and $R_{14}$ and $R_{15}$ each represent a hydrogen atom can be prepared by hydrolysis of a corresponding compound of formula (I) in which R represents a CH—$R_6$ radical in which $R_6$ represents an —$NR_{14}R_{15}$ or -alk-$NR_{14}R_{15}$ radical, $R_{14}$ represents a hydrogen atom and $R_{15}$ represents a —$COR_{18}$ radical and $R_{18}$ represents an alkyl radical.

This hydrolysis is generally carried out by means of an acid, such as hydrochloric acid, in aqueous medium, at the boiling temperature of the reaction mixture.

The compounds of formula (I) in which R represents a CH—$R_6$ radical in which $R_6$ represents an —$NR_{14}R_{15}$ radical and $R_{14}$ and $R_{15}$ each represent a hydrogen atom can also be prepared by reduction of a corresponding compound of formula (I) in which R represents a C=$R_3$ radical in which $R_3$ represents an NOH radical.

This reduction is generally carried out by means of zinc, in the presence of ammonium acetate and 28% aqueous ammonia solution, in an aliphatic alcohol, such as ethanol, at the boiling temperature of the reaction mixture.

The compounds of formula (I) in which R represents a CH—$R_6$ radical in which $R_6$ represents an —$NR_{14}R_{15}$ radical, $R_{14}$ represents a hydrogen atom and $R_{15}$ represents a —$COR_{18}$ radical and $R_{18}$ represents an alkyl radical can be prepared by reacting a reducing agent with a corresponding compound of formula (I) in which R represents a C=$R_3$ radical and $R_3$ represents an NOH radical, followed by a treatment with an $(RkCO)_2O$ anhydride in which Rk represents an alkyl (1-5C) radical.

This reaction is generally carried out in acetic acid, at a temperature of between 50° and 100° C. Zinc is preferably used as reducing agent.

The compounds of formula (I) in which R represents a CH—$R_6$ radical and $R_6$ represents an $NR_{14}R_{15}$ or -alk-$NR_{14}R_{15}$ radical, in which $R_{14}$ and $R_{15}$, which are identical or different, each represent an alkyl radical or else $R_{14}$ represents a hydrogen atom and $R_{15}$ represents an alkyl, —$COR_{18}$ or —$SO_2R_{20}$ radical and $R_{18}$ represents an alkyl, cycloalkyl, phenyl, —COO-alk or —$CH_2$—$COOR_{21}$ radical, can be prepared by reacting a corresponding compound of formula (I), in which R represents a CH—$R_6$ radical, $R_6$ represents an —$NR_{14}R_{15}$ or -alk-$NR_{14}R_{15}$ radical, $R_{14}$ represents a hydrogen atom and $R_{15}$ represent a hydrogen atom or an alkyl radical in the compounds in which $R_{14}$ and $R_{15}$, which are different, each represent an alkyl radical, with a halide of formula Hal-Rl in which Rl represents an alkyl, —$COR_{18}$ or —$SO_2R_{20}$ radical in which $R_{18}$ represents an alkyl, cycloalkyl, phenyl, —COO-alk or —$CH_2$—$COOR_{21}$ radical, $R_{20}$ and $R_{21}$ have the same meanings as in the formula (I) and alk represents alkyl.

This reaction is preferably carried out in an inert solvent, such as dimethylformamide, tetrahydrofuran or dimethyl sulphoxide, in the presence of a base, such as tertiary amine (triethylamine, for example) or aromatic amine (pyridine, for example), or an inorganic base, such as an alkali metal hydroxide (sodium hydroxide or potassium hydroxide, for example), at a temperature of between 20° C. and the boiling temperature of the reaction mixture.

The Hal-Rl halides are commercially available or those in which Rl represents a —$COR_{18}$ radical can be obtained from the corresponding carboxylic acids by adaptation of the methods described by B. Helferich et al., Organic Synth., I, 147; R. Adams et al., Organic Synth., I, 394 or J. Cason, Organic Synth., III, 169 and those in which Rl represents an —$SO_2R_{20}$ radical can be obtained from the corresponding sulphonic acids by reaction with a halogenated phosphorus derivative ($PCl_5$ or $POCl_3$, for example) or with thionyl chloride, optionally in an inert solvent, such as dichloromethane, at a temperature of between 20° and 40° C.

The compounds of formula (I) in which R represents a CH—$R_6$ radical and $R_6$ represents an —$NR_{14}R_{15}$ or -alk-$NR_{14}R_{15}$ radical, in which $R_{14}$ represents a hydrogen atom, $R_{15}$ represents a —$COR_{18}$ or —$CSR_{19}$ radical and $R_{18}$ and $R_{19}$ represent an —NH-alk, —$NH_2$, —NH—Ar or —NH—Het radical, can be prepared by reaction of a corresponding compound of formula (I), in which R represents a CH—$R_6$ radical and $R_6$ represents an —$NR_{14}R_{15}$ or -alk-$NR_{14}R_{15}$ radical and $R_{14}$ and $R_{15}$ each represent a hydrogen atom, with an Rm-N=C=Rn derivative in which Rm represents a trimethylsilyl, alkyl or phenyl radical or a saturated or unsaturated, mono- or polycyclic heterocycle containing 4 to 9 carbon atoms and one or a number of heteroatoms (O, S and N) and Rn represents an oxygen or sulphur atom, optionally followed by hydrolysis.

This reaction is preferably carried out in an inert solvent, such as dimethylformamide, tetrahydrofuran or dioxane, at a temperature of between 20° C. and the boiling temperature of the reaction mixture. For the compounds in which $R_{18}$ and $R_{19}$ are $NH_2$ radicals, this reaction is followed by hydrolysis of the silylated derivative obtained above by means of an aqueous solution, at a temperature of between 20° and 50° C.

The Rm-N=C=Rn derivatives are commercially available or can be obtained from the corresponding Rm-$NH_2$ primary amines by reaction with phosgene or with thiophosgene by application or adaptation of the methods described by R. L. Shriner et al., Organic Synth., II, 453 and G. M. Dyon, Organic Synth., I, 165. The Rm-$NH_2$ primary amines in which Rm is a heterocycle can be obtained by application of the methods described by B. A. Tertov et al., Khim. Geterotsikl. Soedin, II, 1552 (1972), which consists in reacting the organolithium of the heterocycle under consideration with $PhN_3$ in the presence of acetic acid, or by adaptation of the methods described by R. C. Larock, "Comprehensive Organic Transformations", published by VCH, page 399, which consist in reacting the organolithium or organomagnesium derivative of the heterocycle with, for example, $(PhO)_2PON_3$, $H_2NOCH_3$ or $N_3CH_2Si(CH_3)_3$. The organolithium or organomagnesium derivative of the heterocycle can be obtained from the heterocycle by application or adaptation of the methods described by D. L. Comins et al., J. Org. Chem., 52, 104 (1987); N. Furukana et al., Tetrahedron Lett., 28 (47), 5845 (1987); A. R. Katritzky et al., Org. Prep. Procedure Int., 20 (6), 585 (1988), A. J. Clarke et al., Tetrahedron Lett., 27, 2373 (1974) and H. W. Gschwend et al., Organic Reaction 26, 1 (1979).

The compounds of formula (I) in which R represents a CH—$R_6$ radical and $R_6$ represents an $NR_{14}R_{15}$ or -alk-$NR_{14}R_{15}$ radical, in which $R_{14}$ represents a hydrogen atom, $R_{15}$ represents a —$COR_{18}$ radical and $R_{18}$ represents a $CH_2$—$NH_2$ radical, can be prepared by reaction of a corresponding compound of formula (I), in which R represents a CH—$R_6$ radical and $R_6$ represents an —$NR_{14}R_{15}$ or -alk-$NR_{14}R_{15}$ radical and $R_{14}$ and $R_{15}$ each represent a hydrogen atom, with a HOOC—$CH_2$—NH-Ro acid in which Ro represents a protecting group of the amine functional group, such as tert-butoxycarbonyl, followed by hydrolysis.

This reaction is preferably carried out in an inert solvent, such as dimethylformamide, in the presence of hydroxybenzotriazole or of 1-(3-dimethylaminopropyl)-3-ethylcarbodiimide and of an organic base, such as a trialkyamine (triethylamine, for example), at a temperature of between 0° and 5° C. Hydrolysis is generally carried out by means of trifluoroacetic acid, at a temperature in the region of 20° C.

The compounds of formula (I) in which R represents a CH—$R_6$ radical, $R_6$ represents an -alk-$NR_{14}R_{15}$ radical and $R_{14}$ and $R_{15}$ each represent a hydrogen atom can also be prepared by reaction of bromine and sodium hydroxide with a derivative of formula

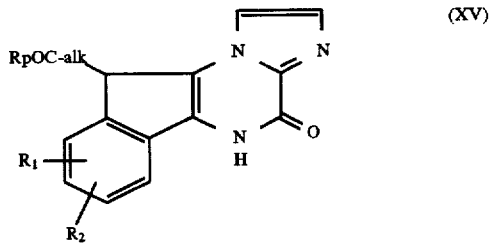

(XV)

in which $R_1$ and $R_2$ have the same meanings as in the formula (I), alk represents an alkyl radical and Rp represents an $NH_2$ radical.

This reaction is generally carried out in aqueous medium, at a temperature of between 20° and 70° C.

The derivatives of formula (XV) can be obtained by reaction of ammonia with a corresponding derivative of formula (XV) in which Rp represents an alkoxy radical.

This reaction is generally carried out in an inert solvent, such as an alcohol, at a temperature in the region of 20° C.

The corresponding derivatives of formula (XV) in which Rp represents an alkoxy radical can be obtained by hydrogenation of a derivative of formula (XIV) in which $R_1$ and $R_2$ have the same meanings as in the formula (I), Rj represents an -alk-CORp radical, Rp represents an alkoxy radical and alk represents an alkyl radical.

This reaction is generally carried out either by means of hydrogen under a pressure of 1 to 50 bar, in the presence of a catalyst, such as palladium-on-charcoal, palladium hydroxide or palladium (N. Rico et al., Nouveau Journal de Chimie, 10, 1, 25, (1988)), in an inert solvent, such as acetic acid, ethyl acetate or an alcohol, at a temperature of between 20° and 60° C., or by adaptation of the method described by L. M. Strawn, J. Med. Chem., 32, 2104 (1989), which consists in reducing the compound with hydroxylamine sulphate and $H_2NOSO_3H$ in water, at a pH of between 6 and 7, at a temperature of 10° C.

The derivatives of formula (XIV) in which Rj represents an -alk-CORp radical and Rp represents an alkoxy radical can be obtained by reaction of a corresponding compound of formula (I), in which R represents a CH—$R_6$ radical and $R_6$ represents a hydrogen atom, with an aldehyde of formula OHC-alk-CORp, in which Rp represents an alkoxy radical and alk represents an alkyl radical. This reaction is generally carried out either in an inert solvent, such as dimethylformamide, 1,2-dimethoxyethane, an alcohol (methanol or ethanol, for example) or a mixture of these solvents, in the presence of a base, such as sodium hydroxide or potassium hydroxide, or a strong organic base, such as 1,8-diazabicyclo[5.4.0]undec-7-ene, at a temperature of between 20° and 100° C., or in dimethyl sulphoxide, in the presence of an alkali metal hydride, such as sodium hydride, at a temperature in the region of 20° C., or in the presence of tetrabutylammonium [lacuna] and of a base, such as an alkali metal hydroxide (sodium hydroxide or potassium hydroxide, for example), in dimethyl sulphoxide, at a temperature of between 20° and 100° C.

The OHC-alk-CORp derivatives are commercially available or can be obtained by reduction of the corresponding HOOC-alk-CORp carboxylic acids in which Rp represents an alkoxy radical and alk represents an alkyl radical, for example by application or adaptation of the methods described by H. C. Brown et al., J. Am. Chem. Soc., 106, 8001 (1984) and J. Org. Chem., 52, 5400 (1987). The HOOC-alk-CORq acids are commercially available or can be obtained, for example, by application or adaptation of the methods described by H. Hunsdieker et al., Chem. Ber., 75, 256 (1942) and R. F. Naylor, J. Chem. Soc., 1108 (1947).

The compounds of formula (I) in which $R_1$ and optionally $R_2$ represent a hydroxyl radical can also be prepared by hydrolysis of a derivative of formula:

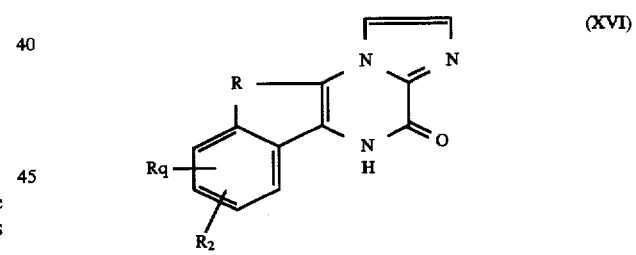

(XVI)

in which R and $R_2$ have the same meanings as in the formula (I) and Rq represents an alkoxy radical.

This reaction is carried out by any method known for the hydrolysis of an alkoxy functional group to a hydroxyl functional group which does not modify the remainder of the molecule. This hydrolysis is preferably carried out by means of hydrobromic acid, at the boiling temperature of the reaction mixture.

The derivatives of formula (XVI) in which Rq represents an alkoxy radical can be obtained by analogy with the processes mentioned above for the preparation of the compounds of formula (I) and in the examples.

The compounds of formula (I) in which $R_1$ and optionally $R_2$ represent a carboxyl radical can also be prepared by hydrolysis of a compound of formula (XVI) in which R and $R_2$ have the same meanings as in the formula (I) and Rq represents a cyano radical.

This hydrolysis is generally carried out in the presence of a strong acid, such as hydrochloric acid or sulphuric acid, at a temperature in the region of 100° C. by adaptation of the methods described by E. Reitz, Organic Synth., III, 851 or R. Adams et al., Organic Synth., I, 436.

The derivatives of formula (XVI) in which Rq represents a cyano radical can be obtained by analogy with the general processes described above for the preparation of the compounds of formula (I).

The compounds of formula (I) in which $R_1$ and optionally $R_2$ represent an alkoxycarbonyl radical can also be prepared by esterification of a corresponding compound of formula (I) in which $R_1$ represents a carboxyl radical.

This esterification is carried out by any method known for the esterification of an acid, such as that described by S. Natelson et al., Organic Synth., III, 382 and E. Aliel et al., Organic Synth., IV, 169. Use is preferably made of an alcohol (methyl alcohol or ethyl alcohol, for example), in the presence of an organic acid (hydrochloric acid or sulphuric acid, for example), in the alcohol under consideration and at the boiling temperature of the reaction mixture.

The compounds of formula (I) in which $R_1$ and optionally $R_2$ represent an —NHCHO radical can also be prepared by reaction of a compound of formula (XVI), in which R and $R_2$ have the same meanings as in the formula (I) and Rq represents an amino radical, with $H_3C$—COOCHO.

This reaction is generally carried out in formic acid, at a temperature in the region of 20° C., optionally in the presence of sodium acetate as acid acceptor when the compound charged to the reaction is in the salified form.

The compounds of formula (I) in which $R_1$ and optionally $R_2$ represent an —N(alk)-CONR$_8$R$_9$, —N(alk-Ar)— CONR$_8$R$_9$, —NH—CSNR$_8$R$_9$ or —N(alk)-CSNR$_8$R$_9$ radical in which $R_8$ and $R_9$ are not hydrogen atoms, an —NH— CO—NR$_9$R$_{12}$ radical in which $R_9$ and $R_{12}$ are not hydrogen atoms, an —NH—COR$_{10}$ radical, an —NH—SO$_2$—NR$_7$R$_9$ radical in which $R_7$ is an alkyl radical, an —NH—SO$_2$— CF$_3$ radical or an —NH—SO$_2$-alk radical can also be prepared by reaction of a compound of formula (XVI), in which R and $R_2$ have the same meanings as in the formula (I) and Rq represents an —NH-alk, —NH-alk-Ar or —NH$_2$ radical in which alk and Ar have the same meanings as in the formula (I), with a derivative of formula Hal-Rr in which Hal represents a halogen atom and Rr represents a —CONR$_8$R$_9$ or —CSNR$_8$R$_9$ radical in which $R_8$ and $R_9$ have the same meanings as in the formula (I) with the exception of hydrogen, a —CO—NR$_9$R$_{12}$ radical in which $R_9$ and $R_{12}$ have the same meanings as in the formula (I) with the exception of hydrogen, a —COR$_{10}$ radical in which $R_{10}$ has the same meanings as in the formula (I), an —SO$_2$—NR$_7$R$_9$ radical in which $R_9$ has the same meanings as in the formula (I) and $R_7$ is an alkyl radical, an —SO$_2$— CF$_3$ radical or an —SO$_2$-alk radical in which alk has the same meanings as in the formula (I).

This reaction is preferably carried out in an inert solvent, such as dimethylformamide, in the presence of an acid acceptor, such as a trialkyamine (triethyamine, for example), at a temperature of between 20° C. and the boiling temperature of the reaction mixture.

The Hal-Rr derivatives in which Rr represents a —CONR$_8$R$_9$ or —CONR$_9$R$_{12}$ radical are commercially available or those in which Hal represents a chlorine atom can be prepared by reaction of the HNR$_8$R$_9$ or HNR$_9$R$_{12}$ amine with phosgene by application or adaptation of the method described by H. Tilles, J. Am. Chem. Soc., 81, 714 (1959).

The HNR$_8$R$_9$ and HNR$_9$R$_{12}$ amines are commercially available or can be obtained by reaction of the H$_2$NR$_8$ or H$_2$NR$_{12}$ primary amine with a HalR$_9$ derivative in which Hal represents a halogen atom (chlorine or bromine, for example) and R$_9$ has the same meanings as in the formula (I) with the exception of hydrogen. This reaction is generally carried out in an inert solvent, such as dimethylformamide, in the presence of a trialkylamine (triethylamine, for example), at a temperature in the region of 20° C.

The H$_2$NR$_8$ or H$_2$NR$_{12}$ primary amines in which $R_8$ or $R_{12}$ represents an -alk-NR$_9$R$_7$ or alk-Het" radical, alk, Het", $R_7$ and $R_9$ having the same meanings as in the formula (I) with the exception of hydrogen, are commercially available or can be obtained by reaction of the potassium salt of phthalimide or of NaN(SiMe$_3$)$_2$ either with a Hal-alk-NR$_9$R$_7$ derivative where Hal represents a halogen atom (chlorine or bromine, for example), alk, $R_7$ and $R_9$ having the same meanings as in formula (I) with the exception of hydrogen, followed by hydrolysis in acidic medium (hydrochloric acid or hydrobromic acid, for example), or with a TsOH$_2$C-alk-Het" derivative in which Ts represents a tosylate residue and alk and Het" have the same meanings as in the formula (I), followed by hydrolysis in acidic medium (hydrochloric acid or hydrobromic acid, for example). These reactions are carried out in an inert solvent, such as dimethylformamide, in the presence of an organic base, such as triethylamine or pyridine, at a temperature of between 0° C. and the boiling temperature of the reaction mixture. The hydrolysis reactions are carried out by means of an aqueous acidic solution (hydrochloric acid, for example), at a temperature of between 20° and 100° C. The Hal-alk-NR$_7$R$_9$ derivatives are commercially available or can be obtained by reaction of Hal-alk-Hal and of a HNR$_9$R$_7$ amine; Hal represents a halogen atom (chlorine or bromine, for example), alk, $R_7$ and $R_9$ having the same meanings as in the formula (I) with the exception of hydrogen. This reaction is carried out in an inert solvent, such as dimethylformamide, in the presence of an organic base, such as triethylamine or pyridine, at a temperature of between 0° C. and the boiling temperature of the reaction mixture. The TsOH$_2$C-alk-Het" derivatives can be obtained from the corresponding HOH$_2$C-alk-Het" alcohols by reaction with the chloride of para-toluenesulphonic acid. This reaction is generally carried out in an inert solvent, such as dimethylformamide or dimethyl sulphoxide, in the presence of an organic base, such as triethylamine or pyridine, at a temperature of between 0° C. and the boiling temperature of the reaction mixture. The HOH$_2$C-alk-Het" alcohols are commercially available or prepared according to the same procedures as for the HO-alk-Het compounds.

The H$_2$N—R$_8$ or H$_2$NR$_{12}$ primary amines in which $R_8$ or $R_{12}$ represents an alk-CO$_2$R$_{21}$ radical are commercially available or can be obtained by application or adaptation of the methods described by D. J. G. Ives et al., J. Chem. Soc., 516 (1943) and in Patent DP 597,305. Preferably, sodium cyanide or potassium cyanide is reacted with a Hal-alk-CO$_2$R$_{21}$ derivative where Hal represents a halogen atom (chlorine or bromine, for example) and alk and R$_{21}$ have the same meanings as in the formula (I), followed by a reduction reaction.

The H$_2$NR$_8$ or H$_2$NR$_{12}$ primary amines in which $R_8$ or $R_{12}$ represents an alk-CO$_2$R$_{21}$ radical can also be obtained by reaction of the potassium salt of phthalimide or of NaN(SiMe$_3$)$_2$ with Hal-alk-CO$_2$R$_{21}$ derivatives or Hal represents a halogen atom (chlorine or bromine, for example) and alk and R$_{21}$ have the same meanings as in the formula (I), by adaptation or application of the methods described in Houben-Weyl, Volume E16 d, Part 2, page 665 (1992).

The Hal-Rs derivatives in which Rs represents a —CS— NR$_8$R$_9$ radical can be obtained by application or adaptation of the methods described by E. Lieber et al., Can. J. Chem., 41, 1643 (1963) or by U. Hasserodt, Chem. Ber., 101, 113 (1968).

The Hal-CO—R$_{10}$ derivatives are commercially available or can be prepared from the corresponding carboxylic acids by adaptation of the methods described by B. Helferich et al., Organic Synth., I, 147; R. Adams et al., Organic Synth., I, 394 or I. Cason, Organic Synth., III, 109.

The derivatives of formula (XVI) in which Rq represents an —NH$_2$, —NH-alk or —NH-alkAr radical can be obtained by analogy with the processes described above for the preparation of the compounds of formula (I).

The compounds of formula (I) in which R$_1$ and optionally R$_2$ represent an —NH—CO—NR$_9$R$_{12}$, —N(alk)-CO—NR$_8$R$_9$ or —N(alk-Ar)—CO—NR$_8$R$_9$ radical can also be prepared by reaction of a derivative of formula (XVI), in which R and R$_2$ have the same meanings as in the formula (I) and Rq represents an —NH$_2$, —NH-alk or —NH-alk-Ar radical in which alk and Ar have the same meanings as in the formula (I), with a halotrialkylsilane, such as chlorotrimethylsilane, in the presence of an alkali metal hydride (sodium hydride, for example), followed by reaction with a coupling agent, such as carbodiimidazole, and then with an amine of formula HN—R$_9$R$_{12}$ or HN—R$_8$R$_9$ in which R$_8$, R$_9$ and R$_{12}$ have the same meanings as in the formula (I).

This reaction is preferably carried out in an inert solvent, such as dimethylformamide, at a temperature of between 20° and 100° C.

The compounds of formula (I) in which R$_1$ and optionally R$_2$ represent an —NH—CO—NR$_9$R$_{12}$, —N(alk)-CO—NR$_8$R$_9$ or —N(alk-Ar)—CO—NR$_8$R$_9$ radical can also be prepared by reaction of a derivative of formula (XVI), in which R and R$_2$ have the same meanings as in the formula (I) and Rq represents an —NH$_2$, —NH-alk or —NH-alk-Ar radical in which alk and Ar have the same meanings as in the formula (I), with a derivative of formula:

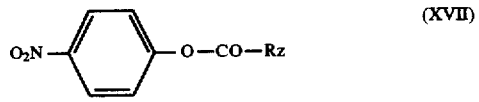

(XVII)

in which Rz represents an —NR$_9$R$_{12}$ or —NR$_8$R$_9$ radical, R$_8$, R$_9$ and R$_{12}$ having the same meanings as in the formula (I).

This reaction is preferably carried out in an inert solvent, such as dimethylformamide, at a temperature of between 20° C. and the boiling temperature of the reaction mixture.

The derivatives of formula (XVII) can be obtained by application or adaptation of the method described by T. Konakahara et al., Synthesis, 103 (1993).

The compounds of formula (I) in which R$_1$ and optionally R$_2$ represent an —NH—CONR$_9$R$_{12}$ radical, R$_9$ represents a hydrogen atom and R$_{12}$ represents a phenyl radical substituted by an amino radical or a phenylalkyl radical substituted by an amino radical can also be prepared by reduction of a corresponding compound of formula (I) in which R$_1$ and optionally R$_2$ represent an —NH—CONR$_9$R$_{12}$ radical, R$_9$ represents a hydrogen atom and R$_{12}$ represents a phenyl radical substituted by a nitro radical or a phenylalkyl radical substituted by a nitro radical.

This reaction is carried out by any method known for the reduction of a nitro functional group to an amino functional group. Reduction is preferably carried out by means of iron and hydrochloric acid, in an inert solvent, such as dimethylformamide, an alcohol (methanol or ethanol, for example) or a mixture of these solvents, at a temperature in the region of 80° C.

The compounds of formula (I) in which R$_1$ and optionally R$_2$ represent an —NH—CONR$_9$R$_{12}$ radical, R$_9$ represents a hydrogen atom and R$_{12}$ represents a phenyl radical substituted by a hydroxyl radical or a phenylalkyl radical substituted by a hydroxyl radical can also be prepared by hydrolysis of a corresponding compound of formula (I) in which R$_1$ and optionally R$_2$ represent an —NH—CONR$_9$R$_{12}$ radical, R$_9$ represents a hydrogen atom and R$_{12}$ represents a phenyl radical substituted by an alkoxy radical or a phenylalkyl radical substituted by an alkoxy radical.

This hydrolysis is carried out by any method which makes it possible to hydrolyse an alkoxy is functional group. Hydrolysis is preferably carried out by means of hydrobromic acid at the boiling temperature of the reaction mixture.

The compounds of formula (I) in which R$_1$ and optionally R$_2$ represent an NH—CONR$_9$R$_{12}$ radical, R$_9$ represents a hydrogen atom and R$_{12}$ represents a phenyl radical substituted by an alk(1C)-NH$_2$ radical or a phenylalkyl radical substituted by an alk(1C)-NH$_2$ radical can also be prepared by hydrogenation of a corresponding compound of formula (I) in which R$_1$ and optionally R$_2$ represent an —NH—CONR$_9$R$_{12}$ radical, R$_9$ represents a hydrogen atom and R$_{12}$ represents a phenyl radical substituted by a cyano radical or a phenylalkyl radical substituted by a cyano radical.

This reaction is generally carried out by means of hydrogen, under a pressure of 1 to 50 bar, in the presence of a catalyst, such as palladium-on-charcoal, palladium hydroxide or Raney nickel, in an inert solvent, such as acetic acid, ethyl acetate or an alcohol, at a temperature of between 20° and 60° C.

The compounds of formula (I) in which R$_1$ and optionally R$_2$ represent an —NH—CONR$_9$R$_{12}$, —N(alk)CONR$_8$R$_9$, —N(alk-Ar)CONR$_8$R$_9$, —NHCSNR$_8$R$_9$ or —N(alk)CSNR$_8$R$_9$ radical in which R$_9$ represents a hydrogen atom, R$_8$ represents a hydrogen atom or an optionally substituted phenylalkyl or alkyl radical, an alk-COOR$_{21}$ radical or an optionally substituted phenyl radical and R$_{12}$ represents a hydrogen atom or an optionally substituted phenylalkyl or alkyl radical, an -alk-COOR$_{21}$ radical or a substituted phenyl radical can also be prepared by reaction of a compound of formula (XVI), in which R and R$_2$ have the same meanings as in the formula (I) and Rq represents an —NH$_2$, —NHalk or —NHalk-Ar radical, alk and Ar having the same meanings as in the formula (I), with a derivative of formula Rs=C=N-Rt in which Rt represents an —Si(CH$_3$)$_3$, benzoyl or alkyl radical, a phenylalkyl radical in which the phenyl ring is optionally substituted by one or a number of substituents chosen from halogen atoms and alkyl, alkoxy, nitro, amino, hydroxyl, -alk-NH$_2$, carboxyl, cyano, —COOR$_{21}$ and -alk-COOR$_{21}$ radicals, an -alk-COOR$_{21}$ radical or a phenyl radical optionally substituted by one or a number of substituents chosen from halogen atoms and alkyl, alkoxy, nitro, amino, hydroxyl, -alk-NH$_{21}$ carboxyl, cyano, —COOR$_{21}$ and -alk-COOR$_{21}$ radicals, in which alk and R$_{21}$ have the same meanings as in the formula (I) and Rs represents an oxygen or sulphur atom.

This reaction is generally carried out in an inert solvent, such as dimethylformamide, optionally in the presence of a trialkylamine (triethylamine, for example), at a temperature of between 20° and 100° C.

The Rs=C=N-Rt derivatives can be obtained from the corresponding primary amines by reaction with phosgene or with thiophosgene by application or adaptation of the methods described by R. L. Shriner et al., Organic Synth. II, 453 and G. M. Dyon, Organic Synth., I, 165. The primary amines can be prepared, for example, by reduction of the corresponding primary amides by adaptation of the methods described by R. C. Larock, "Comprehensive Organic Transformations", published by VCH, page 432 (1989), which consists in using, as reducing agent, either BH$_3$, $BH_3S(CH_3)_2$, $NaBH_4$ or $AlLiH_4$. The corresponding primary amides can be obtained from the corresponding carboxylic acids by reaction with urea by adaptation of the method described by J. L. Guthrie et al., Org. Syntheses, IV, 513.

The Rs=C=N-Rt derivatives in which Rt is a phenyl radical substituted by one or a number of substituents chosen from halogen atoms and alkyl, alkoxy, nitro, amino, hydroxyl, -alk-$NH_2$, —$COOR_{21}$, cyano and -alk-$COOR_{21}$ radicals can be obtained by reaction of trichloromethyl chloroformate in the presence of the corresponding aniline, by adaptation of the method described by R. Katakai, J. Org. Chem., 50, 715 (1985). The corresponding anilines are either commercially available or obtained by reduction of the corresponding nitro derivatives by adaptation of the methods described by R. C. Larock, "Comprehensive Organic Transformations", published by VCH, page 441 (1989), which generally consists in reducing the nitro derivatives using hydrogen, in the presence of a catalyst, such as Raney nickel or palladium-on-charcoal; or from the corresponding halogenated derivatives by adaptation of the methods described by R. C. Larock, "Comprehensive Organic Transformations", published by VCH, page 399 (1989), which consist in preparing the magnesium derivative of the benzene under consideration and by reacting, for example, with $NH_2Cl$, $NH_2OCH_3$ or $N_3CH_2Si(CH_3)_3$.

The corresponding carboxylic acids in which $R_{10}$ represent an -alk-Het" radical are commercially available or can be prepared in the way described above for the Het-alk-$CO_2H$ carboxylic acids.

The compounds of formula (I) in which $R_1$ and optionally $R_2$ represent an —NH—CO—$R_{10}$ radical in which $R_{10}$ represents an alkoxy radical can also be prepared by reaction of a derivative of formula (XVI), in which R and $R_2$ have the same meanings as in the formula (I) and Rq represents an amino radical, with a Hal-COOalk derivative, in which Hal represents a halogen atom and alk represents an alkyl radical, and heating the dialkoxy obtained, optionally in the presence of amine.

This reaction is generally carried out in an inert solvent, such as dioxane or tetrahydrofuran, in the presence of an alkali metal hydride, such as sodium hydride, at a temperature of between 20° C. and the boiling temperature of the reaction mixture. The dialkoxy is then heated in the same solvent, optionally in the presence of a base, such as an amine (triethylamine or N-methylpiperazine, for example).

The compounds of formula (I) in which $R_1$ and optionally $R_2$ represent an NH—CS—$R_{20}$ radical can also be prepared by reaction of $P_2S_5$ with a corresponding compound of formula (I) in which $R_1$ represents an —NH—CO—$R_{10}$ radical in which $R_{10}$ represents an alkyl or phenyl radical.

This reaction is generally carried out in an inert solvent, such as xylene or toluene, at a temperature of between 20° C. and the boiling temperature of the reaction mixture.

The compounds of formula (I) in which $R_1$ and optionally $R_2$ represent an —NH—C(=$NR_{21}$)—$NR_7R_9$ or —N(alk)-C(=$NR_{21}$)—$NR_7R_9$ radical in which $R_{21}$ represents a hydrogen atom or an alkyl radical and $R_7$ represents a hydrogen atom can also be prepared by reaction of methyl iodide with a corresponding compound of formula (I) in which $R_1$ represents an —NH—CS—$NR_8R_9$ or —N(alk)-CS—$NR_8R_9$ radical and $R_8$ represents a hydrogen atom, followed by ammonia or by an alkylamine.

This reaction is preferably carried out in an inert solvent, such as water, dimethylformamide or an alcohol, optionally in the presence of a mercuric salt (preferably mercuric chloride), at a temperature of between 0° C. and the boiling temperature of the reaction mixture.

The compounds of formula (I) in which $R_1$ and optionally $R_2$ represent a —CO—$NR_7R_8$ radical can also be prepared by reaction of a corresponding compound of formula (I) in which $R_1$ and optionally $R_2$ represent a carboxyl radical or a reactive derivative of this acid by any method known to those skilled in the art which makes it possible to change from an acid to an amide. This compound is preferably reacted with a $HNR_7R_8$ amine.

When the acid is used, the preparation is carried out in the presence of a coupling agent used in peptide chemistry, such as a carbodiimide (for example, N,N'-dicyclohexylcarbodiimide) or N,N'-carbonyl-diimidazole, in an inert solvent, such as an ether (tetrahydrofuran or dioxane, for example), an amide (dimethylformamide) or a chlorinated solvent (methylene chloride, 1,2-dichloroethane or chloroform, for example), at a temperature of between 0° C. and the reflux temperature of the reaction mixture. When an ester is used, the preparation is then carried out either in an organic medium, optionally in the presence of an acid acceptor, such as a nitrogenous organic base (trialkylamine, pyridine, 1,8-diazabicyclo[5.4.0]undec-7-ene or 1,5-diazabicyclo[4.3.0]non-5-ene, for example), in a solvent such as mentioned above, or a mixture of these solvents, at a temperature of between 0° C. and the reflux temperature of the reaction mixture, or in a two-phase water/organic medium in the presence of an alkali metal or alkaline-earth metal base (sodium hydroxide or potassium hydroxide) or of an alkali metal or alkaline-earth metal carbonate or bicarbonate, at a temperature of between 0° and 40° C.

The compounds of formula (I) in which $R_1$ and optionally $R_2$ represent an —$NR_9R_{11}$ radical and $R_{11}$ represents a Het" radical can also be prepared by reaction of a compound of formula (XVI), in which R and $R_2$ have the same meanings as in the formula (I) and Rq represents an —$NH_2$ or —NHalk radical in which alk has the same meanings as in the formula (I), with a Hal-Het" derivative in which Hal represents a halogen atom and Het" has the same meanings as in the formula (I).

This reaction is preferably carried out in an inert solvent, such as dimethylformamide or dimethyl sulphoxide, in the presence of an alkali metal hydride, such as sodium hydride, at a temperature of between 20° and 100° C.

The Hal-Het" derivatives can be obtained by halogenation of the corresponding heterocycles by adaptation of the methods described by H. M. Gilow et al., J. Org. Chem., 2221 (1981); K. H. R. Wooldridge, Adv. Heterocycl. Chem., 14, 1 (1972).

The compounds of formula (I) in which $R_1$ and optionally $R_2$ represent an —$S(O)_m$-alk-Ar radical and m is equal to 1 or 2 can be prepared by oxidation of the corresponding compounds of formula (I) in which $R_1$ and optionally $R_2$ represent an —$S(O)_m$-alk-Ar radical in which alk and Ar have the same meanings as in the formula (I) and m is equal to 0.

This reaction is carried out by any method known for the oxidation of a sulphur atom to sulphone or sulphoxide. Preferably, sulphoxides are obtained by means of oxidizing agents, such as sodium periodate, in an inert solvent, such as a water/alcohol mixture, at a temperature in the region of 20° C., and the sulphones by means of an oxidizing agent, such as hydrogen peroxide, in an organic acid, such as acetic acid, at a temperature in the region of 20° C.

The compounds of formula (I) in which $R_1$ and optionally $R_2$ represent a 2-oxo-1-imidazolidinyl or 2-oxo-1-perhydropyrimidinyl radical can also be prepared by cyclization of a derivative of formula (XVI) in which R and $R_2$ have the same meanings as in the formula (I) and Rq represents an —NH—CO—NH—$(CH_2)_n$-Hal radical in which Hal represents a halogen atom, alk represents an alkyl radical and n is equal to 2 or 3.

This reaction is preferably carried out in an inert solvent, such as dimethyl sulphoxide, in the presence of an alkali metal hydride, such as sodium hydride, at a temperature of between 0° and 60° C.

The derivatives of formula (XVI) in which R and $R_2$ have the same meanings as in the formula (I) and Rq represents an —NH—CO—NH—$(CH_2)_n$-Hal radical in which Hal represents a halogen atom and n is equal to 2 or 3 can be prepared by analogy with the processes described above for the compounds of formula (I) and in the examples.

The compounds of formula (I) in which $R_1$ and optionally $R_2$ represent an —NH—CO—$NR_9R_{12}$ or —NH—$COR_{10}$ radical in which $R_{12}$ and $R_{10}$ represent -alk-$COOR_{21}$ radicals and $R_{21}$ represents a hydrogen atom can also be prepared by hydrolysis of a corresponding compound of formula (I) in which $R_1$ represents an —NH—CO—$NR_9R_{12}$ or —NH—$COR_{10}$ radical in which $R_{12}$ and $R_{10}$ represent -alk-$COOR_{21}$ radicals and $R_{21}$ represents an alkyl radical.

This hydrolysis is carried out by means of a base, such as an alkali metal hydroxide (sodium hydroxide or potassium hydroxide, for example) in an inert solvent, such as an alcohol (ethanol or methanol, for example), at a temperature of between 20° and 60° C.

The compounds of formula (I) in which $R_1$ and optionally $R_2$ represent an —$NR_9R_{10}$ radical, $R_9$ represents a hydrogen atom, $R_{11}$ represents a Het" radical and Het" represents a 2-imidazolinyl radical can also be prepared by cyclization of a derivative of formula (XVI) in which R and $R_2$ have the same meanings as in the formula (I) and Rq represents an —N=C($SCH_3$)—NH—$(CH_2)_2$—$NH_2$ radical.

This reaction is generally carried out in an inert solvent, such as a lower aliphatic alcohol (methanol or ethanol, for example), in the presence of an alkali metal alkoxide, such as sodium methoxide, at a temperature in the region of 20° C.

The derivatives of formula (XVI) in which R and $R_2$ have the same meanings as in the formula (I) and Rq represents an —N=C($SCH_3$)—NH—$(CH_2)_2$—$NH_2$ radical can be obtained by application or adaptation of the processes described by A. Katsuhiko et al., J. Org. Chem., 57, 417 (1992).

It is understood by a person skilled in the art that, in order to implement the processes described above according to the invention, it may be necessary to introduce protecting groups of the amino, hydroxyl and carboxyl functional groups, in order to avoid side reactions. These groups are those which may be removed without affecting the rest of the molecule. Examples of protecting groups of the amino functional group which may be mentioned are tert-butyl or methyl carbamates which may be regenerated using iodotrimethylsilane. Examples of protecting groups of the hydroxyl functional group which may be mentioned are the triethylsilyl and benzyl groups. Mention may be made, as protecting groups of the carboxyl functional groups, of esters (methoxymethyl ester, tetrahydropyranyl ester or benzyl ester, for example), oxazoles and 2-alkyl-1,3-oxazolines. Other protecting groups which may be used are described by W. Greene et al., Protecting Groups in Organic Synthesis, second edition, 1991, John Wiley & Sons.

The compounds of formula (I) can be purified by the usual known methods, for example by crystallization, chromatography or extraction.

The enantiomers of the compounds of formula (I) in which R represents a $C(R_4)R_5$ or CH—$R_6$ radical can be obtained by resolution of the racemic mixtures, for example by chromatography on a chiral column according to W. H. Pirckle et al., Asymetric Synthesis, Vol. 1, Academic Press (1983) or by synthesis from chiral precursors.

The diastereoisomers of the compounds of formula (I) in which R represents a $C(R_4)R_5$ or CH—$R_6$ radical containing one or a number of chiral carbons and the various E and Z isomers of the compounds of formula (I) can be separated by the usual known methods, for example by crystallization or chromatography.

The compounds of formula (I) containing a basic residue can optionally be converted to addition salts with an inorganic or organic acid by the action of such an acid in an organic solvent such as an alcohol, a ketone, an ether or a chlorinated solvent.

The compounds of formula (I) containing an acid residue can optionally be converted to metal salts or to addition salts with nitrogenous bases according to methods known per se. These salts can be obtained by reacting a metal base (alkali metal or alkaline-earth metal, for example), ammonia, an amine or a salt of an amine with a compound of formula (I), in a solvent. The salt formed is separated by the usual methods.

These salts also form part of the invention.

There may be mentioned, as examples of pharmaceutically acceptable salts, the addition salts with inorganic or organic acids (such as acetate, propionate, succinate, benzoate, fumarate, maleate, oxalate, methanesulphonate, isethionate, theophyllineacetate, salicylate, methylenebis(β-hydroxynaphthoate), hydrochloride, sulphate, nitrate and phosphate), the salts with alkali metals (sodium, potassium or lithium) or with alkaline-earth metals (calcium or magnesium), the ammonium salt or the salts of nitrogenous bases (ethanolamine, trimethylamine, methylamine, benzylamine, N-benzyl-β-phenethylamine, choline, arginine, leucine, lysine or N-methylglucamine).

The compounds of formula (I) exhibit advantageous pharmacological properties. These compounds are antagonists of the α-amino-3-hydroxy-5-methyl-4-isoxazolepropionic acid (AMPA) receptor, also known under the name of the quisqualate receptor.

Moreover, the compounds of formula (I) are non-competitive antagonists of the N-methyl-D-aspartate (NMDA) receptor and, more particularly, they are ligands for the glycine-modulatory sites of the NMDA receptor.

These compounds are thus useful for treating or preventing all ischaemias (such as focal or global ischaemia) resulting from cerebrovascular accidents, a cardiac arrest, arterial hypotension, a heart or pulmonary surgical operation or severe hypoglycaemia. They are also useful in the treatment of effects due to anoxia, whether perinatal or resulting from drowning or cerebrospinal lesions. These compounds can also be used for treating or preventing the development of neurodegenerative diseases, Huntington's chorea, Alzheimer's disease, amyotrophic lateral sclerosis, olivopontocerebellar atrophy and Parkinson's disease. These compounds can also be used with respect to epileptogenic and/or convulsive symptoms, for the treatment of cerebral or spinal traumas, traumas related to degeneration of the inner ear (R. Pujol et al., Neuroreport, 3, 299–302 (1992)) or of the retina (J. L. Monsinger et al., Exp. Neurol., 113, 10–17 (1991)), of anxiety (Kehne et al., Eur. J. Pharmacol., 193, 283 (1991)), of depression (Trullas et al., Eur. J. Pharmacol., 185, 1 (1990)), of schizophrenia (Reynolds, TIPS, 13, 116 (1992)), of Tourette's syndrome and of hepatic encephalopathies, as analgesics (Dickenson et al., Neurosc. Letters, 121, 263 (1991)), anti-inflammatories (Sluta et al., Neurosci. Letters, 149, 99–102 (1993)), antianorexics (Sorrels et al., Brain Res., 572, 265 (1992)), antimigraines and antiemetics, and for treating poisonings by neurotoxins or other agonist substances of the NMDA receptor, and neurological disorders associated with viral diseases such as AIDS (Lipton et al., Neuron, 7, 111 (1991)), rabies, measles and tetanus (Bagetta et al., Br. J. Pharmacol., 101, 776 (1990)). These compounds are also useful for preventing symptoms of withdrawal from drugs and from alcohol and inhibiting addiction to and dependence on opiates. They can also be used in the treatment of deficiencies related to mitochondrial anomalies such as mitochondrial myopathy, Leber's syndrome, Wernicke's encephalopathy, Rett's syndrome, homocysteinaemia, hyperprolinaemia, hydroxybutyricaminoaciduria, saturnine encephalopathy (chronic lead poisoning) and sulphite oxidase deficiency.

The affinity of the compounds of formula (I) with respect to the AMPA receptor was determined by studying the antagonism of the specific binding of [$^3$H]-AMPA on rat cerebral cortex membranes (Honoré et al., Neuroscience Letters, 54, 27 (1985)). The [$^3$H]-AMPA is incubated in the presence of 0.2 mg of proteins at 4° C. for 30 minutes in 10 mM $KH_2PO_4$, 100 mM KSCN, pH 7.5 buffer. The non-specific binding is determined in the presence of 1 mM L-glutamate. The bonded radioactivity is separated by filtration on Pharmacia filters (Printed Filtermate A). The inhibiting activity of these products is less than or equal to 100 μM.

The affinity of the compounds of formula (I) for the glycine site linked to the NMDA receptor was determined by studying the antagonism of the specific binding of [$^3$H]-DCKA on rat cerebral cortex membranes according to the method described by T. Canton et al., J. Pharm. Pharmacol., 44, 812 (1992). The [$^3$H]-DCKA (20 nM) is incubated in the presence of 0.1 mg of proteins at 4° C. for 30 minutes in 50 mM, pH 7.5, HEPES buffer. The non-specific binding is determined in the presence of 1 mM glycine. The bonded radioactivity is separated by filtration on Whatman GF/B filters. The inhibiting activity of these products is less than or equal to 100 μM.

The compounds of formula (I) have a low toxicity. Their $LD_{50}$ in mice is greater than 50 mg/kg by the IP route.

The compounds of formula (I) are preferred in which

R represents a C=$R_3$ radical, $R_1$ represents a hydroxyl, polyfluoroalkoxy, carboxyl, —NH—CHO, —N(alk)-CO—$NR_8R_9$, —NH—CO—$NR_9R_{12}$, —NH—CS—$NR_8R_9$, NH—CO—$R_{10}$, —NH—$SO_2$—$NR_7R_9$, —CO—$NR_7R_9$, —NH—$SO_2$-alk, —$NR_9R_{11}$, —S(O)$_m$-alk-Ar, —$SO_2$—$NR_7R_9$ or 2-oxo-1-imidazolidinyl radical, $R_2$ represents a hydrogen atom and $R_3$ represents an oxygen atom or an NOH radical, or R represents a CH—$R_6$ radical, $R_1$ represents a hydroxyl, polyfluoroalkoxy, carboxyl, —NH—CHO, —N(alk)-CO—$NR_8R_9$, —NH—CO—$NR_9R_{12}$, —NH—CS—$NR_8R_9$, NH—CO—$R_{10}$, —NH—$SO_2$—$NR_7R_9$, —CO—$NR_7R_9$, —NH—$SO_2$-alk, $NR_9R_{11}$, —S(O)$_m$-alk-Ar, —$SO_2$—$NR_7R_9$ or 2-oxo-1-imidazolidinyl radical, $R_2$ represents a hydrogen atom and $R_6$ represents a hydrogen atom radical or an —$NR_{14}R_{15}$ radical.

Those among these compounds are preferred in which $R_1$ is in the 8- or 9-position.

The following compounds are particularly advantageous:

9-phenylacetamido-5H,10H-imidazo[1,2-a]indeno[1,2-e]pyrazine-4-one, 8-ethoxycarbonylamino-5H,10H-imidazo[1,2-a]indeno[1,2-e]pyrazine-4-one, 8-[3-(3-cyanophenyl)ureido]-5H,10H-imidazo[1,2-a]indeno[1,2-e]pyrazine-4-one, 8-[3-(3-methoxyphenyl)ureido]-5H,10H-imidazo[1,2-a]indeno[1,2-e]pyrazine-4-one, 8-phenylacetamido-5H,10H-imidazo[1,2-a]indeno[1,2-e]pyrazine-4-one, 8-(3-phenylethylureido)-5H,10H-imidazo[1,2-a]indeno[1,2-e]pyrazine-4-one, 8-(3-methylureido)-5H,10H-imidazo[1,2-a]indeno[1,2-e]pyrazine-4-one, 8-(3-benzylureido)-5H,10H-imidazo[1,2-a]indeno[1,2-e]pyrazine-4-one, 8-(3-tert-butylureido)-5H,10H-imidazo[1,2-a]indeno[1,2-e]pyrazine-4-one, 8-(3-phenylpropionamido)-5H,10H-imidazo[1,2-a]indeno[1,2-e]pyrazine-4-one, 8-benzamido-5H,10H-imidazo[1,2-a]indeno[1,2-e]pyrazine-4-one, 8-(4-phenylbutyrylamino-5H,10H-imidazo[1,2-a]indeno[1,2-e]pyrazine-4-one, 8-(5-phenylvalerylamino-5H,10H-imidazo[1,2-a]indeno[1,2-e]pyrazine-4-one, 8-(3-ethoxycarbonylmethylureido)-5H,10H-imidazo[1,2-a]indeno[1,2-e]pyrazine-4-one, 8-(3-carboxymethylureido)-5H,10H-imidazo[1,2-a]indeno[1,2-e]pyrazine-4-one, 8-(3,3-dimethylureido)-5H,10H-imidazo[1,2-a]indeno[1,2-e]pyrazine-4-one, 8-hydroxy-5H,10H-imidazo[1,2-a]indeno[1,2-e]pyrazine-4-one, 8-(3-aminopropionamido-5H,10H-imidazo[1,2-a]indeno[1,2-e]pyrazine-4-one, 8-aminoacetamido-5H,10H-imidazo[1,2-a]indeno[1,2-e]pyrazine-4-one, 8-[3-(3-nitrophenyl)ureido]-5H,10H-imidazo[1,2-a]indeno[1,2-e]pyrazine-4-one, 8-[3-(2-methoxyphenyl)ureido]-5H,10H-imidazo[1,2-a]indeno[1,2-e]pyrazine-4-one, 8-[3-(2-nitrophenyl)ureido]-5H,10H-imidazo[1,2-a]indeno[1,2e-]pyrazine-4-one, 8-[3-(4-aminophenyl)ureido]-5H,10H-imidazo[1,2-a]indeno[1,2-e]pyrazine-4-one, 8-[3-(4-methoxyphenyl)ureido]-5H,10H-imidazo[1,2-a]indeno[1,2e-]pyrazine-4-one, 8-(4-methylpentanoyl)amino-5H,10H-imidazo[1,2-a]indeno[1,2-e]pyrazine-4-one, N,N-dimethyl-4-oxo-4,5-dihydro-10H-imidazo[1,2-a]indeno[1,2e-]pyrazine-8-sulphonamide, 8-(3-phenylthioureido)-5H,10H-imidazo[1,2-a]indeno[1,2-e]pyrazine-4-one, 8-(3-methylthioureido)-5H,10H-imidazo[1,2-a]indeno[1,2-e]pyrazine-4-one, 8-(2-oxo-1-imidazolinyl)-5H,10H-imidazo[1,2-a]indeno[1,2e-]pyrazine-4-one, 8-formamido-5H,10H-imidazo[1,2-a]indeno[1,2-e]pyrazine-4-one, 8-(3-ethoxycarbonylpropionylamino)-5H,10H-imidazo[1,2-a]indeno[1,2-e]pyrazine-4-one, 8-[3-(2-ethoxycarbonylethyl)ureido]-5H,10H-imidazo[1,2-a]indeno[1,2-e]pyrazine-4-one, 8-[3-(2-carboxyethyl)ureido]-5H,10H-imidazo[1,2-a]indeno[1,2-e]pyrazine-4-one, 8-[3-(4-fluorophenyl)ureido]-5H,10H-imidazo[1,2-a]-indeno[1,2-e]pyrazine-4-one, 8-[3-(3-fluorophenyl)ureido]-5H,10H-imidazo[1,2-a]indeno[1,2-e]pyrazine-4-one, 8-[3-(2-fluorophenyl)ureido]-5H,10H-imidazo[1,2-a]-indeno[1,2-e]pyrazine-4-one, 8-(3-ethylureido)-5H,10H-imidazo[1,2-a]indeno[1,2-e]pyrazine-4-one, 8-[3-morpholinoureido]-5H,10H-imidazo[1,2-a]indeno[1,2-e]pyrazine-4-one, 10-amino-8-(3-methylureido)-5H,10H-imidazo[1,2-a]indeno[1,2-e]pyrazine-4-one, 10-hydroxyimino-8-(3-methylureido)-5H,10H-imidazo[1,2-a]indeno[1,2-e]pyrazine-4-one, 8-(3-methylureido)-5H-imidazo[1,2-a]indeno[1,2-e]pyrazin-4,10-dione, 8-[3-(3-aminophenyl)ureido]-5H,10H-imidazo[1,2-a]indeno[1,2e-]pyrazine-4-one, 5H,10H-imidazo[1,2a-]indeno[1,2-e]-pyrazine-4-one-8-carboxylic acid, 8-ureido-5H,10H-imidazo[1,2-a]indeno[1,2-e]pyrazine-4-one, 8-[3-(2-aminoethyl)thioureido]-5H,10H-imidazo[1,2-a]indeno[1,2e-]pyrazine-4-one, 8-thioureido-5H,10H-imidazo[1,2-a]indeno[1,2-e]pyrazine-4-one, 8-[(2-imidazolin-2-yl)amino]-5H,10H-imidazo[1,2-a]indeno[1,2e-]pyrazine-4-one, 8-[(1-pyrrolidinyl)carbonylamino]-5H,10H-imidazo[1,2-a]indeno[1,2-e]pyrazine-4-one, 8-[(1-azetidinyl)carbonylamino]-5H,10H-imidazo[1,2-a]indeno[1,2e-]pyrazine-4-one, 8-(3-propylureido)-5H,10H-imidazo[1,2-a]indeno[1,2e-]pyrazine-4-one, 8-(3-isopropylureido)-5H,10H-imidazo[1,2-a]indeno[1,2e-]pyrazine-4-one, 8-(3-butylureido)-5H,10H-imidazo[1,2-a]indeno[1,2-e]pyrazine-4-one, 8-[(2-thiazolin-2-yl)amino]-5H,10H-imidazo[1,2-a]indeno[1,2-e]pyrazine-4-one, 8-(1,3-dimethylureido)-5H,10H-imidazo[1,2-a]indeno[1,2e-]pyrazine-4-one, 8-[3-(3-carbomethoxyphenyl)ureido]-5H,10H-imidazo[1,2-a]indeno[1,2e-]pyrazine-4-one, 8-[3-(3-carboxyphenyl)ureido]-5H,10H-imidazo[1,2-a]indeno[1,2-e]pyrazine-4-one, 8-[3-(4-carboxyphenyl)ureido]-5H,10H-imidazo[1,2-a]indeno[1,2e-]pyrazine-4-one, 8-[3-(4-carbomethoxybenzyl)ureido]-5H,10H-imidazo[1,2-a]indeno[1,2e-]pyrazine-4-one, 8-[3-(4-carboxybenzyl)ureido]-5H,10H-imidazo[1,2-a]indeno[1,2e-]pyrazine-4-one, 8-[3-(2-fluorobenzyl)ureido]-5H,10H-imidazo[1,2-a]indeno[1,2e-]pyrazine-4-one, 8-[3-(3-fluorobenzyl)ureido]-5H,10H-imidazo[1,2-a]indeno[1,2e-]pyrazine-4-one, 8-[3-(4-fluorobenzyl)ureido]-5H,10H-imidazo[1,2-a]indeno[1,2-e]pyrazine-4-one, 9-carboxy-5H,10H-imidazo[1,2-a]indeno[1,2-e]pyrazine-4-one, 9-carboxamido-5H,10H-imidazo[1,2-a]indeno[1,2-e]pyrazine-4-one, 9-(N-diethylcarboxamido)-5H,10H-imidazo[1,2-a]indeno[1,2-e]pyrazine-4-one, 9-(N-ethylcarboxamido)-5H,10H-imidazo[1,2-a]indeno[1,2-e]pyrazine-4-one, 9-(3-methylureido)-5H,10H-imidazo[1,2-a]indeno[1,2-e]pyrazine-4-one, 8-[3-(4-methoxybenzyl)ureido]-5H,10H-imidazo[1,2-a]indeno[1,2e-]pyrazine-4-one, 8-methylsulphonamido-5H,10H-imidazo[1,2-a]indeno[1,2-e]pyrazine-4-one and their salts.

The following examples illustrate the invention.

EXAMPLE 1

0.84 ml of triethylamine and then 0.61 ml of phenylacetyl chloride are added dropwise to a suspension of 0.63 g of 9-amino-5H,10H-imidazo[1,2-a]indeno[1,2e-]pyrazine-4-one hydrochloride in 25 ml of dimethylformamide; the temperature of the reaction mixture then rises to 30° C. The suspension is brought to reflux for 2 hours (complete dissolution). After cooling to a temperature in the region of 20° C., the insoluble material is removed and the filtrate concentrated to dryness under reduced pressure (15 mm Hg, 2 kPa). The oil thus obtained is taken up in a mixture of ethyl acetate and distilled water. The solid formed is filtered and washed with 50 ml of boiling water and then 50 ml of acetone. 0.40 g of 9-phenylacetamido-5H,10H-imidazo[1,2-a]indeno[1,2-e]pyrazine-4-one hydrate are thus obtained in the form of a greenish-grey solid which decomposes at around 215° C. (analysis $C_{21}H_{18}N_4O_3.0.3H_2O$, % calculated C: 67.37, H: 4.85, N: 14.96, % found C: 67.2, H: 4.6, N: 15.2).

9-Amino-5H,10H-imidazo[1,2-a]indeno[1,2-e]pyrazine-4-one hydrochloride can be prepared in the following way: 0.84 g of 9-acetamido-5H,10H-imidazo[1,2-a]indeno[1,2-e]pyrazine-4-one in 6 ml of 6N hydrochloric acid is heated at reflux until completely dissolved. After cooling to a temperature in the region of 20° C., the precipitate formed is filtered, washed with ethyl acetate and then dried under partial vacuum (1 mm Hg, 0.13 kPa) at 45° C. There is thus obtained 0.79 g of the expected product in the form of a beige powder, the melting point of which is greater than 260° C.

9-Acetamido-5H,10H-imidazo[1,2-a]indeno[1,2-e]pyrazine-4-one can be obtained in the following way: 1 g of 4-acetamido-2-(2-ethoxycarbonyl-1H-imidazol-1-yl)indanone and 26 g of ammonium acetate in 33 ml of acetic acid are heated at reflux for 3 hours. After cooling to a temperature in the region of 20° C., the precipitate formed is filtered, washed with water and dried under reduced pressure (1 mm Hg, 0.13 kPa) at 45° C. There is thus obtained 0.69 g of the expected product in the form of a brown powder, the melting point of which is greater than 260° C.

4-Acetamido-2-(2-ethoxycarbonyl-1H-imidazol-1-yl]indanone can be prepared according to the following protocol: 14.87 g of ethyl 1H-imidazole-2-carboxylate and 14.14 g of 4-acetamido-2-bromoindanone (65% pure) are heated at 110° C. for 15 minutes. After cooling to a temperature in the region of 20° C., the crude product is purified by flash chromatography on a silica column, using ethyl acetate and then a mixture of ethyl acetate and methanol (90/10 by volume) as eluents. 4.34 g of the expected product are thus isolated in the form of a greenish-grey solid melting at 160° C.

4-Acetamido-2-bromoindanone can be obtained in the following way: 1.6 ml of bromine, in solution in 5 ml of acetic acid, are added dropwise over approximately 1 hour to 9.92 g of 4-acetamidoindanone and 1.6 ml of concentrated hydrobromic acid in solution in 110 ml of acetic acid. After stirring for 2 hours at a temperature in the region of 20° C., 1.6 ml of bromine, in solution in 5 ml of acetic acid, are again added. The reaction is continued for 1 hour and the reaction mixture is then poured into ice-cold water. The organic phase is extracted with ethyl acetate, washed with water and dried to lead to 13.44 g of the expected product in the form of a beige solid (65% pure) used as is in the subsequent syntheses.

4-Acetamidoindanone can be prepared according to the following process: 16.7 ml of triethylamine and then 8.5 ml of acetyl chloride are added to 17.5 g of 4-aminoindanone, in solution in 120 ml of tetrahydrofuran, at a temperature in the region of 10° C. The reaction is continued for 15 hours at a temperature in the region of 20° C. The reaction mixture is concentrated to dryness under reduced pressure (15 mm Hg, 2 kPa) and the residue obtained taken up in a mixture of ethyl acetate and distilled water. The organic phase is washed with water, dried and concentrated to dryness under reduced pressure. After purification by flash chromatography on a silica column, using ethyl acetate as eluent, 10.84 g of the expected product are isolated in the form of a beige powder melting at 145° C.

4-Aminoindanone can be obtained according to the method described by V. Hach and M. Protiva, Collect. Czech. Chem. Commun., 23, 1902 (1958).

EXAMPLE 2

0.36 ml of N-methylpiperazine is added dropwise to 0.5 g of 8-ethoxycarbonylamino-4-ethoxycarbonyloxy-10H-imidazo[1,2-a]indeno[1,2-e]-pyrazine, in solution in 10 ml of tetrahydrofuran, at a temperature in the region of 20° C. The reaction is continued for 30 minutes at the same temperature and the reaction mixture is then concentrated to dryness under reduced pressure (15 mm Hg, 2 kPa). The residue is taken up in a mixture of dichloromethane and methanol, the precipitate formed is filtered, washed with 10 ml of methanol and dried under partial vacuum (1 mm Hg, 0.13 kPa) at 400° C. There is thus obtained 0.21 g of 8-ethoxycarbonylamino-5H,10H-imidazo[1,2-a]indeno[1,2e-]pyrazine-4-one in the form of a reddish powder melting at 260° C. (analysis $C_{16}H_{14}N_4O_3 \cdot 0.6H_2O$, % calculated C: 61.92, H: 4.55, N: 18.06, % found C: 61.9, H: 4.5, N: 18.3).

8-Ethoxycarbonylamino-4-ethoxycarbonyloxy-10H-imidazo[1,2-a]indeno[1,2-e]pyrazine can be prepared in the following way: 1.22 g of 60% sodium hydride are added progressively to a suspension of 3.5 g of 8-amino-5H,10H-imidazo[1,2-a]indeno[1,2-e]pyrazine-4-one in 200 ml of dioxane. The reaction mixture is then heated at 55° C. for 2 hours. After cooling to a temperature in the region of 20° C., 4.2 ml of ethyl chloroformate are rapidly added to the reaction mixture and the reaction is continued for 2 hours at a temperature in the region of 20° C. Hydrolysis leads to a solid which is filtered; the filtrate is concentrated to dryness under reduced pressure (15 mm Hg, 2 kPa) and the residue is taken up in water, filtered and dried. Purification by flash chromatography on a silica column, using a mixture of dichloromethane and methanol (95/5 by volume) as eluent, leads to 2 g of the expected product in the form of a pale pink solid melting at 169° C. after recrystallization from absolute ethanol (Analysis $C_{19}H_{188}N_4O_5$, % calculated C: 59.69, H: 4.74, N: 14.65, % found C: 59.9, H: 5.1, N: 14.8).

8-Amino-5H,10H-imidazo[1,2-a]indeno[1,2e-]pyrazine-4-one can be prepared in the following way: a mixture of 9.7 g of 5H,10H-8-nitroimidazo[1,2-a]indeno[1,2-e]pyrazine-4-one, 370 ml of 0.1N aqueous sodium hydroxide solution and 0.3 g of 10% palladium-on-charcoal is hydrogenated at a temperature in the region of 20° C. under a pressure of 1.2 bar for 23 hours. The suspension is acidified with 80 ml of 1N hydrochloric acid and is then filtered. The solid obtained is taken up in 600 ml of boiling water. The mixture is treated with animal charcoal and filtered while hot through celite. The filtrate crystallizes after cooling in an ice bath. The crystals are separated by filtration and washed twice with 50 ml of ethyl ether. There are thus obtained 4.7 g of 5H,10H-8-aminoimidazo[1,2-a]indeno[1,2-e]pyrazine-4-one mono-hydrochloride in the form of a beige solid melting above 260° C. (N.M.R. spectrum: (300 MHz, $d_6$-DMSO, δ in ppm): 4.02 (s,2H, —$CH_2$— at 10), 7.00 (broad d, J=8 Hz, 1H, —$H_7$), 7.20 (broad s, 1H, —$H_9$), 7.74 (d, J=8 Hz, 1H, —$H_6$), 7.77 and 8.07 (2 broad s, each 1H, —H of the imidazole), 12.65 (broad unresolved peak, 1H, —CO—NH—)).

5H,10H-8-Nitroimidazo[1,2a-]indeno[1,2-e]pyrazine-4-one can be prepared in the following way: 1 g of potassium nitrate is added in 10 minutes at a temperature in the region of 5° C. to a solution of 2.6 g of 5H,10H-imidazo[1,2a-]indeno[1,2e-]pyrazine-4-one hydrochloride in 20 ml of concentrated sulphuric acid (d=1.83). The mixture is stirred for 30 minutes at the same temperature and for 3 hours at 25° C. and is then poured into 150 ml of ice-cold water. The crystals which appear are separated by filtration, washed with distilled water and then with acetone and dried under reduced pressure (1 mm Hg, 0.13 kPa) at 80° C. There are thus obtained 2.1 g of 8-nitro-5H,10H-imidazo[1,2-a]indeno[1,2e-]pyrazine-4-one which decomposes without melting above 300° C. (N.M.R. spectrum: (200 MHz, $d_6$-DMSO, δ in ppm): 4.23 (s, 2H, —$CH_2$— at 10), 7.68 and 8.12 (2 broad s, each 1H, —H of the imidazole), 8.07 (dd, J=8.5 Hz, 1H, —H6), 8.38 (dd, J=8.5 and 1.5 Hz, 1H, —H7), 8.50 (d, J=1.5 Hz, 1H, —H9), 12.64 (broad unresolved peak, 1H, —CONH—)).

5H,10H-Imidazo[1,2a-]indeno[1,2-e]pyrazine-4-one can be prepared in the following way: a solution of 4.8 g of 3-methyl-4-oxo-5H,10H-imidazo[1,2-a]indeno[1,2e-]pyrazinium bromide in 30 g of imidazole is heated for 24 hours at 160° C., cooled to 100° C. and then poured into a stirred mixture of 75 g of ice and 75 g of distilled water. The insoluble material is filtered, washed twice with a total of 2 ml of distilled water and then dried under reduced pressure (10 mm Hg, 1.3 kPa) at 50° C. The product thus obtained (4 g) is dissolved in 80 ml of dimethylformamide and the solution, to which 20 g of silica is added, is concentrated to dryness under reduced pressure (15 mm Hg, 2 kPa) at 100° C. The mixture is introduced into a column with a diameter of 4.2 cm containing 240 g of silica and is then eluted with a dichloromethane/methanol (97/3 by volume) mixture, 60 ml fractions being collected. Fractions 10 to 70 are combined, treated with 1.5 g of decolorizing charcoal, filtered and concentrated to dryness under reduced pressure (15 mm Hg, 2 kPa) at 55° C. The product obtained (1.7 g) is dissolved in 350 ml of boiling methanol and the solution, to which 0.1 g of decolorizing charcoal is added, is filtered while hot, concentrated under reduced pressure (15 mm Hg, 2 kPa) at 40° C. in order to bring its volume to approximately 30 ml and then stored at 5° C. for 60 hours. The crystals are separated by filtration, washed twice with a total of 20 ml of ice-cold methanol and dried under reduced pressure (1 mm Hg, 0.13 kPa) at 60° C. There are thus obtained 1.1 g of 5H,10H-imidazo[1,2-a]indeno[1,2-e]-pyrazine-4-one which decomposes without melting at 350° C. [Rf=0.77, thin layer chromatography on silica gel, solvent: dichloromethane/methanol (8/2 by volume)].

3-Methyl-4-oxo-5H,10H-imidazo[1,2-a]indeno[1,2-e]pyrazinium bromide can be prepared in the following way: a solution of 5 g of 1-methyl-1H-imidazole-2-carboxamide and 12 g of 85% 2-bromoindanone in 100 ml of anhydrous dimethylformamide is stirred for 28 hours at 115° C. and is then cooled to a temperature in the region of 20° C. The insoluble material is separated by filtration, washed twice with a total of 20 ml of ice-cold dimethylformamide and dried under reduced pressure (10 mm Hg, 1.3 kPa). There are thus obtained 4.8 g of 3-methyl-4-oxo-5H,10H-imidazo[1,2-a]indeno[1,2-e]pyrazinium bromide (N.M.R. spectrum:

(200 MHz, d$_6$-DMSO, δ in ppm): 4.13 (s, 2H, —CH$_2$ at 10), 4.34 (s, 3H, N$^+$—CH$_3$), 7.47 (mt, 2H, —H7 and —H8), 7.68 and 7.96 (2d, J=7.5 Hz, each 1H, —H6 and —H9), 8.32 and 8.45 (2d, J=1 Hz, each 1H, H of the imidazole), 13.60 (broad unresolved peak, 1H, NH)).

1-Methyl-1H-imidazole-2-carboxamide can be prepared according to the process described by D. D. Davey, J. Org. Chem., 52, 4379 (1987).

EXAMPLE 3

2 ml of triethylamine and then 2.1 g of 3-cyanophenyl isocyanate, in solution in 10 ml of dimethylformamide, are added dropwise to a suspension of 2 g of 8-amino-5H,10H-imidazo[1,2-a]indeno[1,2-e]pyrazine-4-one hydrochloride in 30 ml of dimethylformamide. The reaction mixture is heated for 2 hours at 60° C. and then left overnight at a temperature in the region of 20° C. The precipitate formed is filtered, washed with distilled water and then with isopropyl ether and dried under reduced pressure (1 mm Hg, 0.13 kPa) at 40° C. There are thus obtained 1.2 g of 8-[3-(3-cyanophenyl)ureido]-5H,10H-imidazo[1,2a-]indeno[1,2-e]pyrazine-4-one hydrate in the form of a beige solid, the melting point of which is greater than 260° C. (Analysis C$_{21}$H$_{14}$N$_6$O$_2$.0.4H$_2$O, % calculated C: 63.00, H: 4.03, N: 20.99, % found C: 63.1, H: 4.4, N: 21.3).

EXAMPLE 4

2 ml of triethylamine and then 2.16 g of 3-methoxyphenyl isocyanate, in solution in 10 ml of dimethylformamide, are added dropwise to a suspension of 2 g of 8-amino-5H,10H-imidazo[1,2-a]indeno[1,2-e]pyrazine-4-one hydrochloride in 30 ml of dimethylformamide. The reaction is continued for 5 hours at a temperature in the region of 20° C. The precipitate formed is filtered, washed with water and then with isopropyl ether and dried under reduced pressure (1 mm Hg, 0.13 kPa) at 40° C. There are obtained 1.4 g of 8-[3-(3-methoxyphenyl)ureido]-5H,10H-imidazo[1,2-a]indeno[1,2e-]pyrazine-4-one in the form of a beige solid, the melting point of which is greater than 260° C. (Analysis C$_{21}$H$_{17}$N$_5$O$_3$.0.69H$_2$O, % calculated C: 65.11, H: 4.42, N: 18.08, % found C: 64.8, H: 4.4, N: 17.8).

EXAMPLE 5

1.6 ml of triethylamine and then, after dissolution, 1 ml of phenylacetyl chloride are added to a suspension of 1 g of 8-amino-5H,10H-imidazo[1,2-a]indeno[1,2e-]pyrazine-4-one hydrochloride in 45 ml of dimethylformamide. The reaction mixture is brought to reflux for 6 hours. After cooling to a temperature in the region of 20° C., the precipitate formed is filtered and then recrystallized from 30 ml of dimethylformamide. The solid thus obtained is filtered, washed with water and then with ethyl ether and dried under partial vacuum (1 mm Hg, 0.13 kPa) at 80° C. There is obtained 0.9 g of 8-phenylacetamido-5H,10H-imidazo[1,2-a]indeno[1,2e-]pyrazine-4-one in the form of a yellow solid, the melting point of which is greater is 260° C. (Analysis C$_{21}$H$_{16}$N$_4$O$_2$.1.6H$_2$O.0.4DMF, % calculated C: 70.78, H: 4.53, N: 15.72, % found C: 70.8, H: 4.2, N: 16.0).

EXAMPLE 6

2.3 ml of triethylamine, followed by a solution of 1.61 g of phenethyl isocyanate in 10 ml of dimethyl sulphoxide, are added dropwise to 1.5 g of 8-amino-5H,10H-imidazo[1,2-a]indeno[1,2e-]pyrazine-4-one hydrochloride in suspension in 50 ml of dimethyl sulphoxide. The reaction is continued for 15 hours at a temperature in the region of 20° C. The precipitate formed is filtered, washed with water and recrystallized from 5 ml of dimethylformamide. After filtration, washing with water and then with acetone and drying under reduced pressure (1 mm Hg, 0.13 kPa) at 80° C., there is obtained 0.23 g of 8-(3-phenethylureido)-5H,10H-imidazo[1,2-a]indeno[1,2e-]pyrazine-4-one in the form of a yellow solid, the melting point of which is greater than 260° C. (Analysis C$_{21}$H$_{16}$N$_4$O$_2$.0.78H$_2$O.0.25DMF.0.25DMSO, % calculated C: 68.56, H: 4.97, N: 18.17, % found C: 68.3, H: 4.6, N: 18.6).

EXAMPLE 7

2.3 ml of triethylamine and then, after dissolution, 0.65 ml of methyl isocyanate, in solution in 10 ml of dimethylformamide, are added to 1.5 g of 8-amino-5H,10H-imidazo[1,2-a]indeno[1,2-e]pyrazine-4-one hydrochloride in suspension in 50 ml of dimethylformamide. The reaction is continued for 15 hours at a temperature in the region of 20° C. 0.65 ml of methyl isocyanate, in solution in 10 ml of dimethylformamide, is again added and stirring is maintained for an additional 4 hours at the same temperature. The insoluble material is then filtered, washed with water and recrystallized from dimethylformamide and then from dimethyl sulphoxide. After washing with water and with acetone, the product is dried under reduced pressure (1 mm Hg, 0.13 kPa) at 100° C. There is thus obtained 0.3 g of 8-(3-methylureido)-5H,10H-imidazo[1,2-a]indeno[1,2-e]pyrazine-4-one in the form of a beige solid, the melting point of which is greater than 260° C. (Analysis C$_{15}$H$_{13}$N$_5$O$_2$1.26H$_2$O, % calculated C: 61.01, H: 4.44, N: 23.72, % found C: 61.4, H: 4.8, N: 24.1).

EXAMPLE 8

The preparation is carried out as in Example 7, from 1.5 g of 8-amino-5H,10H-imidazo[1,2-a]indeno[1,2-e]pyrazine-4-one hydrochloride, 2.3 ml of triethylamine, 2 times 1.5 ml of benzyl isocyanate and 60 ml of dimethylformamide. The insoluble material thus formed is filtered and then recrystallized from dimethylformamide. After filtration, copious washing with water and with acetone and drying under vacuum, there is obtained 0.74 g of 8-(3-benzylureido)-5H,10H-imidazo[1,2-a]indeno[1,2e-]pyrazine-4-one in the form of an ecru solid which decomposes at 230° C. (Analysis C$_{21}$H$_{17}$N$_5$O$_2$.1.55H$_2$O, % calculated C: 67.91, H: 4.61, N: 18.86, % found C: 67.8, H: 4.5, N: 18.9).

EXAMPLE 9

The preparation is carried out as in Example 7, from 1.2 g of 8-amino-5H,10H-imidazo[1,2-a]indeno[1,2-e]pyrazine-4-one hydrochloride, 1.8 ml of triethylamine, 2 times 0.6 ml of tert-butyl isocyanate and 25 ml of dimethylformamide. After addition of 100 ml of distilled water to the reaction mixture, the precipitate formed is filtered and recrystallized from dimethylformamide. The solid thus obtained is washed with water, then with ethyl ether and dried under reduced pressure (1 mm Hg, 0.13 kPa) at 80° C. There is obtained 0.31 g of 8-(3-tert-butylureido)-5H,10H-imidazo[1,2-a]indeno[1,2-e]pyrazine-4-one in the form of a brown solid, the melting point of which is greater than 260° C. (Analysis C$_{18}$H$_{19}$N$_5$O$_2$0.83H$_2$0.0.03DMF, % calculated C: 64.08, H: 5.68, N: 20.76, % found C: 63.7, H: 5.9, N: 20.6).

EXAMPLE 10

1.25 ml of hydrocinnamoyl chloride are added dropwise, at a temperature in the region of 20° C., to 1 g of 8-amino- 5H,10H-imidazo[1,2-a]indeno[1,2e-]pyrazine-4-one, dissolved in 75 ml of dimethylformamide. The reaction mixture is brought to reflux for 6 hours. After cooling to a temperature in the region of 20° C., the precipitate formed is filtered and recrystallized from dimethylformamide. The solid thus obtained is filtered, washed with water and then with ethyl ether and dried under partial vacuum (1 mm Hg, 0.13 kPa) at 80° C. [lacuna] 0.69 g of 8-(3-phenylpropionamido)-5H, 10H-imidazo[1,2-a]indeno[1,2-e]pyrazine-4-one in the form of a yellow solid which decomposes at 200° C. (Analysis $C_{22}H_{18}N_4O_2 \cdot 0.93H_2O \cdot 0.15DMF$, % calculated C: 71.34, H: 4.90, N: 15.13, % found C: 71.0, H: 5.0, N: 15.2).

EXAMPLE 11

The preparation is carried out as in Example 10, from 1 g of 8-amino-5H,10H-imidazo[1,2-a]indeno[1,2-e]pyrazine-4-one and 1 ml of benzoyl chloride in 75 ml of dimethylformamide. The reaction is continued for 8 hours at reflux. The suspension is filtered and the filtrate concentrated to dryness under reduced pressure (15 mm Hg, 2 kPa). The residue is taken up in dimethylformamide while hot and the solution left overnight at 0° C. The precipitate formed is filtered, washed with water and dried under vacuum (1 mm Hg, 0.13 kPa) at 80° C. There is thus obtained 0.28 g of 8-benzamido-5H,10H-imidazo[1,2a-]indeno[1,2-e]pyrazine-4-one in the form of a pink solid, the melting point of which is greater than 260° C. (Analysis $C_{20}H_{14}N_4O_2 \cdot 0.79H_2O \cdot 0.40DMF$, % calculated C: 70.17, H: 4.12, N: 16.37, % found C: 70.0, H: 3.9, N: 16.4).

EXAMPLE 12

A few drops of dimethylformamide and then, dropwise, 2.8 ml of thionyl chloride are added to 5 g of 4-phenylbutyric acid, in solution in 60 ml of anhydrous dichloromethane, at a temperature in the region of 20° C. After reacting overnight at the same temperature, the reaction mixture is concentrated to dryness under reduced pressure. The chloride of 4-phenylbutyric acid thus prepared is added dropwise to 1 g of 8-amino-5H,10H-imidazo[1,2-a]indeno[1,2-e]pyrazine-4-one, in solution in 75 ml of dimethylformamide, at a temperature in the region of 20° C. The reaction mixture is heated at reflux for 7 hours. The precipitate formed is filtered and recrystallized from dimethylformamide. After filtration, washing with water and then ethyl ether and drying under partial vacuum (1 mm Hg, 0.13 kPa) at 80° C., there is obtained 0.64 g of 8-(4-phenylbutyrylamino- 5H,10H-imidazo[1,2-a]indeno[1,2-e]pyrazine-4-one in the form of an ochre solid which decomposes at 190° C. (Analysis $C_{23}H_{20}N_4O_2 \cdot 0.63H_2O \cdot 0.79DMF$, % calculated C: 71.86, H: 5.24, N: 14.57, % found C: 71.5, H: 5.1, N: 14.8).

EXAMPLE 13

The preparation is carried out as in Example 12, from 5 g of 5-phenylvaleric acid, 2.5 ml of thionyl chloride, 60 ml of dichloromethane, 1 g of 8-amino-5H,10H-imidazo[1,2-a]indeno[1,2-e]pyrazine-4-one and 75 ml of dimethylformamide. After refluxing for 7 hours, the insoluble material is filtered and recrystallized from dimethylformamide. After filtration, washing with water and drying under reduced pressure (1 mm Hg, 0.13 kPa) at 80° C., there is obtained 0.58 g of 8-(5-phenylvalerylamino-5H,10H-imidazo[1,2-a]indeno[1,2-e]pyrazine-4-one in the form of a yellow solid which decomposes at 170° C. (Analysis $C_{24}H_{22}N_4O_2 \cdot 0.41DMF$, % calculated C: 72.34, H: 5.56, N: 14.06, % found C: 72.0, H: 5.6, N: 13.8).

EXAMPLE 14

The preparation is carried out as in Example 7, from 3 g of 8-amino-5H,10H-imidazo[1,2-a]indeno[1,2-e]pyrazine-4-one and 2 times 2.8 ml of ethyl 2-isocyanatoacetate in 170 ml of dimethylformamide. The insoluble material thus obtained is filtered and recrystallized from dimethylformamide. After filtration, washing with water and drying under reduced pressure (1 mm Hg, 0.13 kPa) at 60° C., there are obtained 2.6 g of 8-(3-ethoxycarbonylmethylureido)-5H, 10H-imidazo[1,2-a]indeno[1,2-e]pyrazine-4-one in the form of a pink solid, the melting point of which is greater than 260° C. (Analysis $C_{18}H_{17}N_5O_4 \cdot 0.75H_2O \cdot 0.20DMF$, % calculated C: 58.85, H: 4.66, N: 19.06, % found C: 58.9, H: 5.0, N: 18.9).

EXAMPLE 15

20 ml of 30% sodium hydroxide solution are added, at a temperature in the region of 20° C., to 1 g of 8-(3-ethoxycarbonylmethylureido)-5H,10H-imidazo[1,2-a]indeno[1,2-e]pyrazine-4-one in suspension in 40 ml of ethanol. The reaction is continued for 18 hours at 50° C. After cooling to a temperature in the region of 20° C., the precipitate formed is filtered, then taken up in 20 ml of distilled water and the mixture is acidified using concentrated hydrochloric acid. The suspension is stirred for 2 hours at a temperature in the region of 20° C. and then filtered, washed with water and dried under partial vacuum (1 mm Hg, 0.13 kPa) at 100° C. After recrystallization from dimethylformamide, there is obtained 0.22 g of 8-(3-carboxymethylureido)-5H,10H-imidazo[1,2-a]indeno[1,2-e]pyrazine-4-one dihydrate in the form of a beige solid, the melting point of which is greater than 260° C. (Analysis $C_{16}H_{12}N_5O_4 \cdot 2.0 \cdot H_2O \cdot 0.1DMF$, % calculated C: 56.64, H: 3.86, N: 20.64, % found C: 56.7, H: 3.8, N: 21.0).

EXAMPLE 16

1.2 ml of dimethylcarbamoyl chloride are added dropwise to 1.5 g of 8-amino-5H,10H-imidazo[1,2-a]indeno[1,2-e]pyrazine-4-one and 0.15 g of 4-dimethylaminopyridine in 45 ml of pyridine. After reacting for 5 hours at a temperature in the region of 20° C., 1.2 ml of dimethylcarbamoyl chloride are again added. The reaction is continued overnight at the same temperature and the reaction mixture is then heated at 50° C. for 1 hour. After cooling, the insoluble material is filtered, washed with water and dried. The solid thus obtained is recrystallized from dimethylformamide, washed with water and then dried under partial vacuum (1 mm Hg, 0.13 kPa) at 50° C. There is obtained 0.3 g of 8-(3,3-dimethylureido)-5H,10H-imidazo[1,2-a]indeno[1,2-e]pyrazine-4-one dihydrate in the form of a pink solid, the melting point of which is greater than 260° C. (Analysis $C_{16}H_{15}N_5O_2 \cdot 2H_2O$, % calculated C: 62.13, H: 4.89, N: 22.64, % found C: 62.2, H: 4.6, N: 22.4).

EXAMPLE 17

0.5 g of 8-methoxy-5H,10H-imidazo[1,2-a]indeno[1,2e-]pyrazine-4-one, in suspension in 20 ml of concentrated hydrobromic acid, is heated at reflux for 6 hours. After cooling to a temperature in the region of 20° C., the insoluble material is filtered and recrystallized from dimethylformamide to lead, after filtration, washing with ethyl ether and drying under partial vacuum (1 mm Hg, 0.13 kPa) at 80° C., to 0.14 g of 8-hydroxy-5H,10H-imidazo[1,2-a]indeno[1,2-e]pyrazine-4-one in the form of a yellow solid, the melting point of which is greater than 260° C. (N.M.R.

spectrum [200 MHz, d₆-DMSO, δ in ppm]: 3.96 (s, 2H, —CH₂— at 10), 6.84 (broad d, J=8 Hz, 1H, —H7), 7.04 (broad s, 1H, —H9), 7.69 (d, J=8 Hz, 1H, —H6), 7.86 and 8.15 (2s, each 1H, H of the imidazole), 9.73 (broad unresolved peak, 1H, OH), 12.80 (broad s, 1H, CONH)).

8-Methoxy-5H,10H-imidazo[1,2-a]indeno[1,2-e]pyrazine-4-one can be obtained in the following way: 6.3 g of ethyl 1-[2-(5-methoxy-1-oxoindanyl)]imidazole-2-carboxylate are dissolved in a 4N solution of ammonium acetate in glacial acetic acid. After refluxing for 12 hours, the mixture is cooled to a temperature in the region of 20° C. and filtered. The solid obtained is washed with water to neutral pH and with 50 ml of acetone and is then recrystallized while hot from 75 ml of dimethylformamide. The crystals formed are separated by filtration and mixed successively with 50 ml of water and 50 ml of acetone. There are thus obtained 3.3 g of the product in the form of a beige solid melting above 260° C. (N.M.R. spectrum: (200 MHz, d₆-DMSO, δ in ppm): 3.82 (s, 3H, —OCH₃), 3.98 (s, 2H, —CH₂— at 10), 6.98 (dd, J=8 and 1.5 Hz, 1H, —H7), 7.22 (d, J=1.5 Hz, 1H, —H9), 7.56 and 7.97 (2s, each 1H, —H of the imidazole), 7.78 (d, J=8 Hz, 1H, —H6), 12.30 (broad s, 1H, —CO—NH—)).

Ethyl 1-[2-(5-methoxy-1-oxoindanyl)]imidazole-2-carboxylate can be prepared in the following way: a mixture of 13.9 g of 2-bromo-5-methoxy-1-indanone and 16.2 g of 2-ethoxycarbonylimidazole in 300 ml of toluene is brought to reflux for 9 hours. The toluene is then evaporated under reduced pressure and the residue is taken up in dichloromethane and water. The organic phase is extracted with dichloromethane and washed with water. After the usual treatment, the crude product is purified by chromatographing twice in succession on a silica column with respectively mixtures of dichloromethane and ethyl acetate (70/30 by volume) and dichloromethane and methanol (98/2 by volume). There are thus obtained 7.5 g of ethyl 1-[2-(5-methoxy-1-oxoindanyl)]imidazole-2-carboxylate (Rf=0.38, thin layer chromatography on silica gel, eluent: dichloromethane/ethyl acetate (70/30 by volume)).

2-Bromo-5-methoxy-1-indanone can be synthesized as described by D. Mukhopadhya and D. N. Chaudhury, J. Indian Chem. Soc., 47(5), 450 (1970).

EXAMPLE 18

A few drops of dimethylformamide and then, dropwise, 1.5 ml of thionyl chloride are added, at a temperature in the region of 20° C., to a suspension of 5 g of N-(9-fluorenylmethyloxycarbonyl)-β-alanine in 100 ml of anhydrous dichloromethane. After stirring overnight at the same temperature, the reaction mixture is concentrated to dryness under reduced pressure (1 mm Hg, 0.13 kPa). The acid chloride thus prepared is dissolved in 30 ml of anhydrous dimethylformamide and added dropwise to a solution prepared from 2 g of 8-amino-5H,10H-imidazo[1,28a]indeno[1,2e-]pyrazine-4-one hydrochloride and 4.5 ml of triethylamine in 50 ml of dimethylformamide, at a temperature in the region of 20° C. The reaction is continued for 7 hours at 100° C. The precipitate, formed after cooling to 0° C., is filtered and then taken up in 25 ml of piperidine. The suspension is stirred for 1 hour at a temperature in the region of 20° C. and the insoluble material is filtered and recrystallized from a mixture of dioxane and 1N hydrochloric acid (50/50 by volume). After filtration, washing with dioxane and then drying under partial vacuum (1 mm Hg, 0.13 kPa) at 50° C., there is obtained 0.65 g of 8-(3-aminopropionamido-5H,10H-imidazo[1,2-a]indeno[1,2-e]pyrazine-4-one hydrochloride in the form of a yellow solid, the melting point of which is greater than 260° C. (Analysis C₁₆H₁₆ClN₅O₂.2.0H₂O 0.86HCl.0.15DMF, % calculated C: 55.58, H: 4.66, Cl: 10.25, N: 20.25, % found C: 55.6, H: 4.3, Cl: 9.9, N: 19.9).

EXAMPLE 19

The preparation is carried out as in Example 18, from 8 g of N-(9-fluorenylmethyloxycarbonyl)glycine, 2.45 ml of thionyl chloride and 2 g of 8-amino-5H,10H-imidazo[1,2-a]indeno[1,2e-]pyrazine-4-one. Recrystallization from a mixture of dioxane and 1N hydrochloric acid (50/50 by volume) leads to 0.19 g of 8-aminoacetamido-5H,10H-imidazo[1,2-a]indeno[1,2-e]pyrazine-4-one hydrochloride in the form of a beige solid, the melting point of which is greater than 260° C. (Analysis C₁₅H₁₄ClN₅O₂.0.74H₂O.0.87HCl.0.05DMF, % calculated C: 61.01, H: 4.44, N: 23.72, % found C: 61.4, H: 4.7, N: 23.6).

EXAMPLE 20

1.53 ml of triethylamine are added, at a temperature in the region of 20° C., to a suspension of 1.5 g of 8-amino-5H,10H-imidazo[1,2-a]indeno[1,2-e]pyrazine-4-one hydrochloride in suspension in 15 ml of dimethylformamide. After solubilization, 1.79 g of 3-nitrophenyl isocyanate, in solution in 10 ml of dimethylformamide, are added dropwise. The reaction mixture is stirred for 15 hours at the same temperature and the suspension is filtered, washed with water and then with isopropyl ether and dried under partial vacuum (1 mm Hg, 0.13 kPa). There are thus obtained 1.2 g of 8-[3-(3-nitrophenyl)ureido]-5H,10H-imidazo[1,2-a]indeno[1,2e-]pyrazine-4-one hydrate in the form of a yellow solid, the melting point of which is greater than 260° C. (Analysis C₂₀H₁₆N₆O₅, % calculated C: 57.14, H: 3.84, N: 19.99, % found C: 57.2, H: 4.0, N: 20.1).

EXAMPLE 21

The preparation is carried out in the same way as in Example 20, from 1 g of 8-amino-5H,10H-imidazo[1,2-a]indeno[1,2-e]pyrazine-4-one hydrochloride, 1 ml of triethylamine and 0.97 ml of 2-methoxyphenyl isocyanate. After reacting for 6 hours at a temperature in the region of 20° C., the insoluble material is filtered and washed with water and then with isopropyl ether. 0.3 g of 8-[3-(2-methoxyphenyl)ureido]-5H,10H-imidazo[1,2-a]indeno[1,2-e]pyrazine-4-one are thus obtained in the form of a beige solid, the melting point of which is greater than 260° C. (Analysis C₂₁H₁₇N₅O₃.0.76H₂O, % calculated C: 65.11, H: 4.42, N: 18.08, % found C: 64.8, H: 4.3, N: 18.4).

EXAMPLE 22

The preparation is carried out in the same way as in Example 20, from 1.5 g of 8-amino-5H,10H-imidazo[1,2-a]indeno[1,2-e]pyrazine-4-one hydrochloride, 1.53 ml of triethylamine and 1.79 g of 2-nitrophenyl isocyanate. After reacting for 6 hours at a temperature in the region of 20° C., the insoluble material is filtered and washed with water and then with isopropyl ether. 0.7 g of 8-[3-(2-nitrophenyl)ureido]-5H,10H-imidazo[1,2-a]indeno[1,2-e]pyrazine-4-one dihydrate are thus obtained in the form of an orangey solid, the melting point of which is greater than 260° C. (Analysis C₂₀H₁₈N₆O₆.0.83H₂O, % calculated C: 54.79, H: 4.14, N: 19.17, % found C: 54.5, H: 3.8, N: 19.1).

EXAMPLE 23

9 ml of concentrated hydrochloric acid are added dropwise to 0.46 g of 8-[3-(4-nitrophenyl)ureido]-5H,10H- imidazo[1,2-a]indeno[1,2-e-]pyrazine-4-one, in suspension in 5 ml of methanol, at a temperature in the region of 20° C. After stirring for 15 minutes, 0.42 g of iron powder and then 10 ml of dimethylformamide are progressively added. The reaction mixture is heated for 10 hours at 80° C. and then, after cooling, the insoluble material is filtered, washed with methanol and then with isopropyl ether and dried under reduced pressure (1 mm Hg, 0.13 kPa) at 50° C. There is obtained 0.22 g of 8-[3-(4-aminophenyl)ureido]-5H,10H-imidazo[1,2-a]indeno[1,2-e-]pyrazine-4-one dihydrochloride in the form of a beige solid, the melting point of which is greater than 260° C. (N.M.R. spectrum: [200 MHz, $d_6$-$d_6$-$(CD_3)_2SO$, δ in ppm]: 4.10 (s, 2H, —$CH_2$— at 10), 7.35 (d, J=8.5 Hz, 2H, aromatic —H ortho to the —$NH_2$), 7.48 (broad d, J=8.5 Hz, 1H, —H7), 7.61 (d, J=8.5 Hz, 2H, aromatic —H meta to the —$NH_2$), 7.86 (d, J=8.5 Hz, 1H, —H6), 7.88 (broad s, 1H, —H9), 7.99 and 8.25 (2 broad s, each 1H, —H of the imidazole), from 8.50 to 9.00 (broad unresolved peak, —NHCONH—), 9.78 (broad s, 3H, —$NH_3^+Cl^-$), from 12.90 to 13.2 (broad unresolved peak, 1H, —NHCO— of the ring)).

8-[3-(4-Nitrophenyl)ureido]-5H,10H-imidazo[1,2-a]indeno[1,2e-]pyrazine-4-one can be obtained in the following way: the preparation is carried out as in Example 20, from 0.69 g of 8-amino-5H,10H-imidazo[1,2a]indeno[1,2e-]pyrazine-4-one hydrochloride, 0.35 ml of triethylamine and 0.82 g of 4-nitrophenyl isocyanate. After stirring for 4 hours at a temperature in the region of 20° C., the insoluble material is filtered, washed with distilled water and dried under partial vacuum (1 mm Hg, 0.13 kPa) at 20° C. There is obtained 0.51 g of 8-[3-(4-nitrophenyl)ureido]-5H,10H-imidazo[1,2a-]indeno[1,2-e]pyrazine-4-one in the form of an ochre solid, the melting point of which is greater than 260° C. (Analysis $C_{20}H_{14}N_6O_4.1.1H_2O$, % calculated C: 59.69, H: 3.51, N: 20.89, % found C: 59.3, H: 3.3, N: 20.8).

EXAMPLE 24

The preparation is carried out in the same way as in Example 20, from 1.5 g of 8-amino-5H,10H-imidazo[1,2a-]indeno[1,2e-]pyrazine-4-one hydrochloride, 1.5 ml of triethylamine and 1.42 ml of 4-methoxyphenyl isocyanate. After reacting for 15 hours at a temperature in the region of 20° C., the insoluble material is filtered and washed with water and then with isopropyl ether. 0.6 g of 8-[3-(4-methoxyphenyl)ureido]-5H,10H-imidazo[1,2a-]indeno[1,2-e]pyrazine-4-one hydrate are thus obtained in the form of a beige solid, the melting point of which is greater than 260° C. (Analysis $C_{21}H_{19}N_5O_4.0.20H_2O$, % calculated C: 62.22, H: 4.72, N: 17.27, % found C: 62.1, H: 4.4, N: 17.4).

EXAMPLE 25

The preparation is carried out as in Example 12, from 5.5 ml of isocaproic acid, 3.9 ml of thionyl chloride, 60 ml of dichloromethane, 1.5 g of 8-amino-5H,10H-imidazo[1,2-a]indeno[1,2-e]pyrazine-4-one and 75 ml of dimethylformamide. After refluxing for 8 hours, the precipitate is filtered and then recrystallized from dimethylformamide. The solid thus obtained is copiously washed with water and dried under partial vacuum (1 mm Hg, 0.13 kPa) at 80° C. in order to lead to 0.81 g of 8-(4-methylpentanoyl)amino-5H,10H-imidazo[1,2-a]indeno[1,2e-]pyrazine-4-one in the form of a yellow powder which decomposes at 220° C. (Analysis $C_{19}H_{20}N_4O_2.1.27H_2O$, % calculated C: 67.84, H: 5.99, N: 16.66, % found C: 67.8, H: 5.7, N: 16.8).

EXAMPLE 26

A solution of 3 g of ethyl 1-[5-(N,N-dimethylsulphamoyl)-1-oxo-2-indaneyl)]imidazole-2-carboxylate in 300 ml of a 5N methanolic ammonia solution is stirred for 20 hours at a temperature in the region of 20° C. The solid which appears is separated by filtration, washed twice with a total of 80 ml of acetone and dried under reduced pressure (15 mm Hg, 2 kPa) at 45° C. A first crop of 1.3 g is thus obtained. The filtrate is concentrated by half under reduced pressure (15 mm Hg, 2 kPa) and the solid which appears is separated by filtration, washed with acetone and dried under reduced pressure (15 mm Hg, 2 kPa) at 45° C. A second crop of 0.2 g is thus obtained. The 2 combined crops are dissolved at 80° C. in 50 ml of a concentrated aqueous hydrochloric acid solution. After cooling to a temperature in the region of 5° C. and addition of 50 ml of distilled water, the solid which appears is separated by filtration, washed 10 times with a total of 100 ml of distilled water and dried under reduced pressure (1 mm Hg, 0.13 kPa) at 80° C. There are thus obtained 1.2 g of N,N-dimethyl-4-oxo-4,5-dihydro-10H-imidazo[1,2-a]indeno[1,2-e]pyrazine-8-sulphonamide melting above 260° C. (N.M.R. spectrum: [200 MHz, $d_6$-$(CD_3)_2SO$, ε in ppm]: 2.66 [s, 6H, —$N(CH_3)_2$], 4.17 (s, 2H, —$CH_2$— at 10), 7.61 and 8.04 (2d, J=1 Hz, each 1H, —H of the imidazole), 7.83 (dd, J=8.5 and 2 Hz, 1H, —H7), 7.97 (d, J=2 Hz, 1H, —H9), 8.10 (d, J=8.5 Hz, 1H, —H6), 12.46 (broad unresolved peak, 1H, —NHCO—)).

Ethyl 1-[5-(N,N-dimethylsulphamoyl)-1-oxo-2-indaneyl)]imidazole-2-carboxylate can be prepared in the following way: a mixture of 3.8 g of ethyl imidazole-2-carboxylate and 4.4 g of 2-bromo-5-(N,N-dimethyl-sulphamoyl)-1-indanone is heated for 8 minutes at 125° C., cooled to 20° C. and chromatographed on 1 kg of neutral silica gel (0.040–0.063 mm) contained in a column with a diameter of 10 cm, elution being carried out with a dichloromethane/ethyl acetate (60/40 by volume) mixture and 100 ml fractions being collected. Fractions 16 to 66 are combined and concentrated to dryness under reduced pressure (15 mm Hg, 2 kPa) at 40° C. The product obtained (4.1 g) is suspended in 50 ml of dichloromethane and, after removal of the insoluble material by filtration, the filtrate is concentrated to dryness under reduced pressure (15 mm Hg, 2 kPa) at 50° C. There are thus obtained 3 g of ethyl 1-[5-(N,N-dimethylsulphamoyl)-1-oxo-2-indaneyl)]imidazole-2-carboxylate in the form of a cream lac.

2-Bromo-5-(N,N-dimethylsulphamoyl)-1-indanone can be prepared in the following way: a solution of 2.2 g of bromine in 10 ml of dichloromethane is added dropwise over 30 minutes at −5° C. to a solution of 3.3 g of 5-(N,N-dimethylsulphamoyl)-1-indanone in a mixture of 30 ml of dichloromethane, 14 ml of acetic acid and 0.1 ml of a 47% aqueous hydrobromic acid solution. The mixture is then stirred for 1 hour at a temperature of between 0° C. and 5° C., stored for 16 hours at a temperature in the region of 5° C., treated with another mixture prepared under the same conditions but from 1.2 g of 5-(N,N-dimethylsulphamoyl)-1-indanone and poured into 150 ml of distilled water. After separation by settling and extraction 3 times with a total of 150 ml of dichloromethane, the combined organic extracts are washed successively with 50 ml of distilled water, 50 ml of a saturated aqueous sodium hydrogencarbonate solution and 50 ml of distilled water, then dried over anhydrous magnesium sulphate and concentrated to dryness under reduced pressure (15 mm Hg, 2 kPa) at 50° C. The product obtained (5.5 g), to which 2 g prepared under the same conditions are added, is chromatographed on 700 g of neutral silica gel (0.040–0.063 mm) contained in a column with a diameter of 8 cm, elution being carried out with dichloromethane and 500 ml fractions being collected. Fractions 3 to 6 are combined and concentrated to dryness under reduced pressure (15 mm Hg, 2 kPa) at 40° C. There are thus obtained 4.4 g of 2-bromo-5-(N,N-dimethylsulphamoyl)-1-indanone, melting at 115° C.

5-(N,N-Dimethylsulphamoyl)-1-indanone can be prepared in the following way: a solution of 7 g of 5-chlorosulphonyl-1-indanone in 70 ml of anhydrous tetrahydrofuran is added dropwise over 30 minutes to 70 ml of dimethylamine maintained at –30° C. The mixture is then stirred for 1 hour at –10° C. and for 16 hours while allowing the temperature to progressively rise to 20° C. and then 300 ml of distilled water and 300 ml of ethyl acetate are added. The organic solution is washed successively with 100 ml of distilled water, with 100 ml of a 1N aqueous hydrochloric acid solution and with distilled water to neutrality, then dried over anhydrous magnesium sulphate and concentrated to dryness under reduced pressure (15 mm Hg, 2 kPa) at 40° C. There are thus obtained 5.8 g of 5-(N,N-dimethylsulphamoyl)-1-indanone, melting at 142° C. 5-Chlorosulphonyl-1-indanone can be prepared as described by J. J. Howbert and T. A. Crowell, Synth. Commun., 20 (20), 3197 (1990).

EXAMPLE 27

1.2 g of triethylamine and then, dropwise over 5 minutes at a temperature in the region of 20° C., a solution of 1.62 g of phenyl isothiocyanate are added to a suspension of 1.3 g of 8-amino-5H,10H-imidazo[1,2-a]indeno[1,2-e]pyrazine-4-one dihydrochloride in 50 ml of anhydrous dimethylformamide. After stirring for 1 hour at the same temperature, the insoluble material which appears is separated by filtration, washed successively with 4 ml of dimethylformamide, 5 ml of distilled water and 5 ml of acetone and dried in the air. The product obtained (1.15 g) is stirred for 1 hour in 15 ml of methanol, filtered, washed with 5 ml of methanol and dried under reduced pressure (1 mm Hg, 0.13 kPa) at 100° C. There is thus obtained 0.9 g of 8-(3-phenylthioureido)-5H,10H-imidazo[1,2-a]indeno[1,2e-]pyrazine-4-one which decomposes without melting above 280° C. (N.M.R. spectrum: [200 MHz, $d_6$-$(CD_3)_2SO$, $\delta$ in ppm]: 4.02 (s, 2H, —$CH_2$— at 10), 7.14 (broad t, J=7.5 Hz, 1H, —H4 of the phenylthioureido), 7.36 (t, J=7.5 Hz, 2H, —H3 and —H5 of the phenylthioureido), 7.45 (dd, J=8.5 and 2 Hz, 1H, —H7), 7.51 (broad d, J=7.5 Hz, 2H, —H2 and —H6 of the phenylthioureido), 7.58 and 7.95 (2d, J=1 Hz, each 1H, —H of the imidazole), 7.76 (d, J=2 Hz, 1H, —H9), 7.80 (d, J=8.5 Hz, 1H, —H6), 9.85 and 9.93 (2 broad s, each 1H, NHCSNH— at 8), 12.50 (broad unresolved peak, 1H, —CONH— of the ring)).

EXAMPLE 28

1.2 g of triethylamine and then, dropwise over 5 minutes at a temperature in the region of 20° C., a solution of 0.9 g of methyl isothiocyanate are added to a suspension of 1.3 g of 8-amino-5H,10H-imidazo[1,2-a]indeno[1,2e-]pyrazine-4-one dihydrochloride in 50 ml of anhydrous dimethylformamide. After stirring for 16 hours at the same temperature, the mixture is poured into 100 ml of distilled water and stirred for 15 minutes. The insoluble material which appears is separated by filtration, washed twice with a total of 10 ml of distilled water and dried under reduced pressure (1 mm Hg, 0.13 kPa) at 100° C. The product obtained (0.25 g) is stirred for 1 hour in 2.5 ml of methanol, filtered, washed with 0.5 ml of methanol and dried under reduced pressure (1 mm Hg, 0.13 kPa) at 100° C. There is thus obtained 0.21 g of 8-(3-methylthioureido)-5H,10H-imidazo[1,2-a]indeno[1,2-e]pyrazine-4-one which decomposes without melting above 280° C. (N.M.R. spectrum: [200 MHz, $d_6$-$(CD_3)_2SO$, $\delta$ in ppm]: 2.96 (d, J=2.5 Hz, 3H, —$CH_3$), 4.10 (broad s, 2H, —$CH_2$— at 10), 7.33 (broad d, J=8.5 Hz, 1H, —H7), 7.56 and 7.96 (2 broad s, each 1H, —H of the imidazole), 7.64 (broad s, 1H, —H9), from 7.65 to 7.80 and 9.65 (2 broad unresolved peaks, each 1H, —NHCSNH— at 8), 7.78 (broad d, J=8.5 Hz, 1H, —H6), 12.34 (broad s, 1H, —NHCO—)).

EXAMPLE 29

A mixture of 0.9 g of 1-(5-benzylthio-1-oxo-2-indaneyl)]imidazole-2-carboxamide and 25 ml of concentrated hydrochloric acid is heated for 20 minutes at 80° C., cooled to a temperature in the region of 20° C. and poured into 25 ml of distilled water. The solid is separated by filtration, washed with distilled water to neutrality and twice with a total of 20 ml of acetone and dried in the air. The product obtained (0.8 g) is dissolved in 150 ml of a boiling mixture of dimethylformamide and distilled water (80/20 by volume) and, after cooling and storing for 1 hour at a temperature in the region of 5° C., the crystals which appear are separated by filtration, washed twice with a total of 20 ml of acetone and dried under reduced pressure (1 mm Hg, 0.13 kPa) at 100° C. There is thus obtained 0.5 g of 8-benzylthio-5H,10H-imidazo[1,2-a]-indeno[1,2e-]pyrazine-4-one which decomposes without melting above 260° C. (N.M.R. spectrum: [200 MHz, $d_6$-$(CD_3)_2SO$, $\delta$ in ppm]: 3.97 (s, 2H, —$CH_2$— at 10), 4.28 (s, 2H, Ar—$CH_2S$—), from 7.15 to 7.45 (mt, 6H, aromatic —H and —H7), 7.56 and 7.95 (2 broad s, each 1H, —H of the imidazole), 7.56 (broad s, 1H, —H9), 7.76 (d, J=8 Hz, 1H, —H6), 12.30 (broad s, 1H, —NHCO—)).

1-(5-Benzylthio-1-oxo-2-indaneyl)]imidazole-2-carboxamide can be prepared in the following way: a solution of 3 g of ethyl 1-(5-benzylthio-1-oxo-2-indaneyl)] imidazole-2-carboxylate in 140 ml of a 5N methanolic ammonia solution is stirred for 20 hours at a temperature in the region of 20° C. After addition of 80 ml of isopropyl ether, the solid which appears is separated by filtration, washed twice with a total of 40 ml of isopropyl ether and dried under reduced pressure (1 mm Hg, 2 kPa) at 60° C. There is thus obtained 0.9 g of 1-(5-benzylthio-1-oxo-2-indaneyl)]imidazole-2-carboxamide, melting at 219° C.

Ethyl 1-(5-benzylthio-1-oxo-2-indaneyl)]-imidazole-2-carboxylate can be prepared in the following way: a mixture of 3 g of ethyl imidazole-2-carboxylate and 3.6 g of 2-bromo-5-benzylthio-1-indanone is heated for 15 minutes at 140° C., cooled to 20° C. and chromatographed on 300 g of neutral silica gel (0.040–0.063 mm) contained in a column with a diameter of 4.5 cm, the elution being carried out with a dichloromethane/ethyl acetate (90/10 by volume) mixture and 30 ml fractions being collected. Fractions 31 to 76 are combined and concentrated to dryness under reduced pressure (15 mm Hg, 2 kPa) at 40° C. The product obtained (1.7 g) is suspended in 50 ml of isopropyl ether and the mixture is stirred for 1 hour at 20° C. The solid is separated by filtration, washed twice with a total of 20 ml of isopropyl ether and dried under reduced pressure (15 mm Hg, 2 kPa) at 40° C. There are thus obtained 1.3 g of ethyl 1-(5-benzylthio-1-oxo-2-indaneyl)]imidazole-2-carboxylate, melting at 131° C.

2-Bromo-5-benzylthio-1-indanone can be prepared in the following way: a solution of 3.2 g of bromine in 25 ml of dichloromethane is added dropwise over 30 minutes at 5° C. to a solution of 5.3 g of 5-benzylthio-1-indanone in 50 ml of dichloromethane. The mixture is stirred for 40 hours at a temperature in the region of 20° C., diluted with 75 ml of dichloromethane, washed 4 times with a total of 200 ml of distilled water, dried over anhydrous sodium sulphate and dried under reduced pressure (15 mm Hg, 2 kPa) at 40° C. The product obtained (7.5 g) is chromatographed on 300 g of neutral silica gel (0.040–0.063 mm) contained in a column with a diameter of 4.5 cm, the elution being carried out with a cyclohexane/ethyl acetate (95/5 by volume) mixture and 30 ml fractions being collected. Fractions 4 to 35 are combined and concentrated to dryness under reduced pressure (15 mm Hg, 2 kPa) at 40° C. There are thus obtained 4 g of 2-bromo-5-benzylthio-1-indanone, melting at 88° C.

5-Benzylthio-1-indanone can be prepared as described by J. J. Howbert and T. A. Crowell, Synth. Commun. 20 (20), 3197 (1990).

EXAMPLE 30

0.29 g of 80% sodium hydride is added, at a temperature in the region of 20° C., to a suspension of 1.37 g of 8-[3-(2-chloroethyl)ureido]-5H,10H-imidazo[1,2-a]indeno[1,2-e]pyrazine-4-one in 35 ml of anhydrous dimethyl sulphoxide. The mixture is then stirred for 1 hour at 50° C., cooled to 20° C., treated with 16 ml of distilled water and acetic acid in order to adjust the pH to 4 and then centrifuged. The supernatant solution is removed and the solid is washed on a filter twice with a total of 10 ml of distilled water and with 5 ml of acetone and then dried under reduced pressure (1 mm Hg, 0.13 kPa) at 100° C. The product obtained (0.93 g) is chromatographed on 28 g of neutral silica gel (0.020–0.045 mm) contained in a column with a diameter of 3.5 cm, elution being carried out under pressure with a chloroform/methanol/28% aqueous ammonia (82/15/3 by volume) mixture and a 170 ml fraction and an 825 ml fraction being collected. The latter is concentrated to dryness under reduced pressure (15 mm Hg, 2 kPa) at 40° C. The product obtained (0.2 g) is stirred for 30 minutes in 2 ml of methanol, separated by filtration, washed twice with a total of 1 ml of methanol and dried under reduced pressure (1 mm Hg, 0.13 kPa) at 100° C. There is thus obtained 0.12 g of 8-(2-oxo-1-imidazolinyl)-5H,10H-imidazo[1,2-a]indeno[1,2-e]pyrazine-4-one which decomposes without melting above 260° C. (N.M.R. spectrum: [200 MHz, d6-(CD$_3$)$_2$SO, δ in ppm]: 3.45 (t, J=7.5 Hz, 2H, —CH$_2$NH—), 3.93 (t, J=7.5 Hz, 2H, —CH$_2$—), 4.00 (s, 2H, —CH$_2$— at 10), 6.97 (broad s, 1H, —CH$_2$—NH—), 7.47 (dd, J=8.5 and 2 Hz, 1H, —H7), 7.56 and 7.92 (2 broad s, each 1H, —H of the imidazole), 7.80 (d, J=8.5 Hz, 1H, —H6), 7.99 (d, J=2 Hz, 1H, —H9), 12.23 (broad s, 1H, —NHCO— of the ring)).

8-[3-(2-Chloroethyl)ureido]-5H,10H-imidazo[1,2-a]indeno[1,2-e]pyrazine-4-one can be prepared in the following way: 2.2 g of triethylamine and then, dropwise at a temperature in the region of 20° C., 1.2 g of 2-chloroethyl isocyanate are added to a suspension of 3.1 g of 8-amino-5H,10H-imidazo[1,2-a]indeno[1,2-e]pyrazine-4-one dihydrochloride in 80 ml of anhydrous dimethylformamide. After stirring for 16 hours at the same temperature, the insoluble material which appears is separated by filtration, washed twice with a total of 40 ml of distilled water and with 20 ml of acetone and then dried under reduced pressure (1 mm Hg, 0.13 kPa) at 100° C. 0.3 g of product obtained (out of 2.63 g obtained in total) is stirred for 5 minutes in 13 ml of dimethyl sulphoxide, separated by filtration, washed twice with a total of 4 ml of distilled water and dried under reduced pressure (1 mm Hg, 0.13 kPa) at 100° C. There is thus obtained 0.15 g of 8-[3-(2-chloroethyl)ureido]-5H,10H-imidazo[1,2-a]indeno[1,2-e]pyrazine-4-one which decomposes without melting above 260° C. (N.M.R. spectrum: [200 MHz, d$_6$-(CD$_3$)$_2$SO, δ in ppm]: 3.47 (q, J=6 Hz, 2H, —CH$_2$—), 3.71 (t, J=6 Hz, 2H, —CH$_2$Cl), 3.97 (s, 2H, —CH$_2$— at 10), 6.50 (t, J=6 Hz, 1H, —CONH—), 7.32 (dd, J=8 and 1.5 Hz, 1H, —H7), 7.57 and 7.92 (2 broad s, each 1H, —H of the imidazole), 7.73 (d, J=8 Hz, 1H, —H6), 7.82 (d, J=1.5 Hz, 1H, —H$_9$), 8.87 (broad s, 1H, —NHCO— at 8), 12.25 (broad s, 1H, —NHCO— of the ring)).

EXAMPLE 31

The mixture of 21.4 g of acetic anhydride and 11.5 g of formic acid is heated for 2 hours at a temperature of between 50° C. and 60° C. and cooled to 20° C. 0.9 g of anhydrous sodium acetate is then added and then, after dissolution, 1.6 g of 8-amino-5H,10H-imidazo[1,2-a]indeno[1,2-e]pyrazine-4-one dihydrochloride. The mixture is stirred for 1 hour at 20° C., cooled to 5° C. and then 10 ml of distilled water are added. The insoluble material which appears is separated by filtration, washed twice with a total of 20 ml of distilled water and dried under reduced pressure (5 mm Hg, 0.65 kPa) at 40° C. 0.5 g of product obtained (out of 1.34 g obtained in total) is stirred for 10 minutes in 10 ml of boiling acetic acid and, after cooling, separated by filtration, washed twice with a total of 2 ml of acetic acid and dried under reduced pressure (1 mm Hg, 0.13 kPa) at 100° C. There is thus obtained 0.45 g of 8-formamido-5H,10H-imidazo[1,2-a]indeno[1,2-e]pyrazine-4-one melting at 280° C. (decomposition) (N.M.R. spectrum [200 MHz, d$_6$-(CD$_3$)$_2$SO, δ in ppm]: Mixture of isomers: 75% of E isomer and 25% of Z isomer: 4.05 (s, 2H, —CH$_2$— at 10), 7.25 (dd, J=8.5 and 2 Hz, 0.25H, —H7 of the Z isomer), 7.50 (S, 0.25H, one of the imidazole —H for the Z isomer), 7.60 (dd, J=8.5 and 2 Hz, 0.75H, —H7 of the E isomer), from 7.70 to 7.90 (mt, 2H, —H6 and —H9), 7.98 and 8.11 (2s, each 0.75H, —H of the imidazole for the E isomer), 8.16 (s, 0.25H, the other imidazole —H for the Z isomer), 8.33 (d, J=2 Hz, 0.75H, —CH=O of the E isomer), 8.86 (d, J=10.5 Hz, 0.25H, —CH=O of the Z isomer), 10.30 (d, J=10.5 Hz, 0.25H, —NHCO at 8 of the Z isomer), 10.41 (broad s, 0.75H, —NHCO— at 8 of the E isomer), 12.70 and 12.74 (2 broad s, 1H in total, —CONH—of the ring)).

EXAMPLE 32

6.25 ml of ethyl 3-(chloroformyl)propionate are added over 5 minutes to a solution of 6 g of 8-amino-5H,10H-imidazo[1,2-a]indeno[1,2-e]pyrazine-4-one hydrochloride, 240 ml of dimethylformamide and 10.75 ml of triethylamine and the reaction mixture is heated at reflux for 6 hours. The mixture is concentrated under reduced pressure and 500 ml of water are added. The precipitate obtained is filtered and dried in the air to give 4.6 g of crude product. A part (2 g) is purified by chromatography on a silica column (80 g), elution being carried out with a mixture of ethyl acetate and methanol (first 70/30 by volume and then 30/70); the silica corresponding to the head of the column is then recovered and treated with 60 ml of dimethylformamide, filtered and rinsed with water. The filtrate is evaporated under reduced pressure and the evaporation residue is dried at 60° C. under vacuum (1 mm Hg, 0.13 kPa). There is obtained 0.27 g of 8-(3-ethoxycarbonylpropionylamino)-5H,10H-imidazo[1,2a-]indeno[1,2-e]pyrazine-4-one in the form of a greenish solid melting above 260° C. (Analysis, % calculated C: 62.29, H: 4.95, N: 15.29, O: 17.47, % % found C: 62.1, H: 4.5, N: 15.7).

EXAMPLE 33

1.19 g of 8-(3-ethoxycarbonylpropionylamino)5H,10H-imidazo[1,2-a]indeno[1,2e-]pyrazine-4-one, 1.2 ml of 10N sodium hydroxide solution and 48 ml of ethanol are heated at 50° C. for 4 hours under an argon blanket. The reaction mixture is filtered and the insoluble material washed with ethanol (2×15 ml) and dried in the air. The solid obtained is triturated in 75 ml of methanol, filtered and dried at 60° C. under vacuum (1 mm Hg, 0.13 kPa). There is obtained 0.32 g of 8-(3-carboxypropionylamino)-5H,10H-imidazo[1,2-a]indeno[1,2-e]pyrazine-4-one in the form of the disodium salt of formula $C_{17}H_{12}N_4O_4Na_2$ (Analysis, % calculated C: 53.41, H: 3.16, N: 14.66, O: 16.74, Na: 12.03, % found C: 53.5, H: 2.7, N: 14.2).

EXAMPLE 34

The preparation is carried out as in Example 32 but from 4 g of 8-amino-5H,10H-imidazo[1,2-a]indeno[1,2-e]pyrazine-4-one hydrochloride, 86 ml of dimethylformamide, 7.3 ml of triethylamine and 4.42 g of ethyl 3-isocyanatopropionate and the reaction mixture is stirred at a temperature in the region of 20° C. for 90 hours. After evaporation of the dimethylformamide, 300 ml of water are added and the precipitate formed is filtered, washed with water (50 ml) and then with acetone (2×50 ml) and dried at 60° C. under vacuum (1 mm Hg, 0.13 kPa). There are obtained 2.1 g of 8-[3-(2-ethoxycarbonylethyl)ureido]-5H,10H-imidazo[1,2-a]indeno[1,2-e]pyrazine-4-one in the form of a beige solid melting above 260° C. (Analysis, % calculated C: 59.84, H: 5.02, N: 18.36, O: 16.78, % found C: 59.5, H: 5.1, N: 18.5).

EXAMPLE 35

The preparation is carried out as in Example 33 but from 0.53 g of 8-[3-(2-ethoxycarbonylethyl)ureido]-5H,10H-imidazo[1,2a-]indeno[1,2-e]pyrazine-4-one, 0.2 ml of 10N sodium hydroxide solution and 8 ml of ethanol. There is obtained 0.47 g of 8-[3-(2-carboxyethyl)ureido]-5H,10H-imidazo[1,2-a]indeno[1,2-e]pyrazine-4-one, melting above 260° C. (Analysis, % calculated C: 51.39, H: 3.30, N: 17.63, O: 16.11, Na: 11.57, % found C: 51.1, H: 2.9, N: 17.3).

EXAMPLE 36

A solution of 1.76 g of 4-fluorophenyl isocyanate in 20 ml of dimethylformamide is added over 30 minutes to a solution of 2 g of 8-amino-5H,10H-imidazo[1,2-a]indeno[1,2-e]pyrazine-4-one hydrochloride, 20 ml of dimethylformamide and 1.3 g of triethylamine and stirring is carried out for 12 hours at a temperature in the region of 20° C. The reaction mixture is filtered and the insoluble material is washed with dimethylformamide (2×10 ml) and then with water (3×15 ml) and dried in the air. The crude product is then triturated in 30 ml of dimethylformamide, filtered, washed with water and then with isopropyl ether and dried at 60° C. under vacuum (1 mm Hg, 0.13 kPa). There are obtained 1.5 g of 8-[3-(4-fluoro-phenyl)ureido]-5H,10H-imidazo[1,2-a]indeno[1,2-e]-pyrazine-4-one in the form of a beige solid melting above 260° C. (Analysis, % calculated C: 64.00, H: 3.76, F: 5.06, N: 18.66, O: 8.52, % found C: 64.0, H: 3.8, N: 19.0).

EXAMPLE 37

The preparation is carried out as in Example 36 but from 1.5 g of 8-amino-5H,10H-imidazo[1,2-a]indeno[1,2-e]pyrazine-4-one hydrochloride, 30 ml of dimethylformamide, 0.97 g of triethylamine and 2.64 g of 3-fluorophenyl isocyanate. There is obtained 0.44 g of 8-[3-(3-fluoro-phenyl)ureido]-5H,10H-imidazo[1,2-a]indeno[1,2-e]-pyrazine-4-one in the form of a light brown solid melting above 260° C. (Analysis, % calculated C: 64.00, H: 3.76, F: 5.06, N: 18.66, O: 8.52, % found C: 64.1, H: 3.4, N: 18.6).

EXAMPLE 38

The preparation is carried out as in Example 36 but from 2 g of 8-amino-5H,10H-imidazo[1,2-a]indeno[1,2-e]pyrazine-4-one hydrochloride, 40 ml of dimethylformamide, 1.3 g of triethylamine and 1.76 g of 2-fluorophenyl isocyanate. There is obtained 1 g of 8-[3-(2-fluorophenyl)ureido]-5H,10H-imidazo[1,2-a]indeno[1,2-e]pyrazine-4-one in the form of a beige solid melting above 260° C. (Analysis, % calculated C: 64.00, H: 3.76, F: 5.06, N: 18.66, O: 8.52, % found C: 64.0, H: 3.5, F: 4.6, N: 18.6).

EXAMPLE 39

The preparation is carried out as in Example 36 but from 2 g of 8-amino-5H,10H-imidazo[1,2-a]indeno[1,2-e]pyrazine-4-one hydrochloride, 40 ml of dimethylformamide, 1.3 g of triethylamine and 1.82 g of ethyl isocyanate. There is obtained 0.85 g of 8-(3-ethylureido]-5H,10H-imidazo[1,2-a]indeno[1,2-e]-pyrazine-4-one in the form of a purple solid melting above 260° C. (Analysis, % calculated C: 62.13, H: 4.89, N: 22.64, O: 10.34, % found C: 61.7, H: 4.9, N: 22.3, O: 9.9).

EXAMPLE 40

50 ml of a solution of 1.5 g of 8-amino-5H,10H-imidazo [1,2-a]indeno[1,2-e]pyrazine-4-one in dimethylformamide are added dropwise to 0.3 g of sodium hydride in suspension in 5 ml of anhydrous dimethylformamide under a nitrogen atmosphere. After stirring for 1 hour at a temperature in the region of 20° C., 2.4 ml of trimethylsilyl chloride are run into the reaction mixture dropwise and stirring is continued for 30 minutes at the same temperature. 2.05 g of 1,1'-carbonyldiimidazole are then progressively added, then, after reacting for 4 hours at 20° C., 2.8 ml of morpholine are added dropwise and the reaction mixture brought to 60° C. for 1 hour. Continuing the reaction overnight at a temperature in the region of 20° C. leads, after filtration of the insoluble material, washing with water and drying under reduced pressure (1 mm Hg, 0.13 kPa) at 50° C., to 1.2 g of crude product in the form of a black powder. This crude product is recrystallized from a mixture of water and dioxane (1/1 by volume) to lead, after washing with water and then drying under reduced pressure, to 0.19 g of 8-[3-morpholinoureido]-5H,10H-imidazo[1,2-a]indeno[1,2-e]-pyrazine-4-one hydrate in the form of a red solid, the melting point of which is greater than 260° C. (Analysis $C_{18}H_{19}N_5O_4.0.26H_2O$, % calculated C: 58.53, H: 5.18, N: 18.96, found C: 58.4, H: 5.2, N: 19.0).

EXAMPLE 41

0.8 g of zinc powder is added to a solution of 1 g of 10-hydroxyimino-8-(3-methylureido)-5H,10H-imidazo[1,2a-]indeno[1,2-e]pyrazine-4-one, 0.1 g of ammonium acetate and 27 ml of aqueous ammonia (28%). The reaction mixture is brought to a temperature in the region of 100° C. for 3 hours. After cooling, 40 ml of hydrochloric acid (6N) are added and the reaction mixture is left stirring for 18 hours at a temperature in the region of 20° C. The suspension thus obtained is filtered and washed with 3 times 25 ml of ethyl ether and 2×25 ml of acetone. The solid residue thus obtained is dried under reduced pressure (0.5–1.5 bar) at 40° C. to lead to 0.56 g of 10-amino-8-(3-methylureido)-5H, 10H-imidazo[1,2-a]indeno[1,2-e]pyrazine-4-one dihydrochloride, melting at a temperature greater than 260° C. (Analysis $C_{15}H_{16}Cl_2N_6O_2.1.31H_2O$: % calculated C: 47.01, H: 4.21, Cl: 18.5, N: 21.93, O: 8.35, % found C: 46.8, H: 4.2, Cl: 16.9, N: 21.2, O: 8.0).

EXAMPLE 42

1.23 g of NaH (80%) are added spatula by spatula to a solution of 5 g of 8-(3-methylureido)-5H,10H-imidazo[1,2-a]indeno[1,2-e]pyrazine-4-one and 50 ml of dimethyl sulfoxide, while maintaining the reaction mixture at a temperature in the region of 20° C. After stirring for one hour at this temperature, a solution of 2.33 g of isoamyl nitrite and 10 ml of dimethyl sulfoxide is added dropwise while maintaining the temperature at 20° C. The reaction mixture is then stirred for 18 hours and then 10 ml of water, 10 ml of acetic acid, 40 ml of methanol and 15 ml of water are successively added. After stirring for 4 hours, the suspension thus obtained is filtered and the solid washed with 3 times 100 ml of water and 2 times 100 ml of methanol. The solid residue thus obtained is dried under reduced pressure (0.5–1.5 bar) at 40° C. to lead to 3 g of 10-hydroxyimino-8-(3-methylureido)-5H,10H-imidazo[1,2-a]indeno[1,2-e]pyrazine-4-one, melting at a temperature greater than 260° C. (Analysis $C_{15}H_{12}N_6O_3.0.25H_2O.0.7DMSO$: % calculated C: 55.56, H: 3.73, N: 25.91, O: 14.81, % found C: 55.0, H: 3.2, N: 26.1, O: 14.5).

EXAMPLE 43

5.6 ml of triethylamine and then 2.36 ml of methyl isocyanate are added dropwise to 2.88 g of 8-amino-5H-imidazo[1,2a-]indeno[1,2-e]pyrazine-4,10-dione hydrochloride, in solution in 40 ml of dimethylformamide, at a temperature in the region of 20° C. Stirring is continued for 15 hours at the same temperature. The precipitate formed is filtered and recrystallized from aqueous dimethyl sulfoxide containing 5% of water. After cooling to a temperature in the region of 20° C., the solid thus obtained is filtered, washed with acetone and dried under reduced pressure (1 mm Hg, 0.13 kPa) at 80° C. to lead to 2.1 g of 8-(3-methylureido)-5H-imidazo[1,2-a]indeno[1,2-e]pyrazine-4,10-dione in the form of a dark-red solid, the melting point of which is greater than 260° C. (Analysis $C_{15}H_{11}N_5O_3.0.17H_2O$, % calculated C: 58.25, H: 3.58, N: 22.64, found C: 58.1, H: 3.6, N: 22.5).

8-Amino-5H-amidazo[1,2-a]indeno[1,2e-]pyrazine-4,10-dione hydrochloride can be prepared according to the following protocol: 5.6 g of 8-nitro-5H-imidazo[1,2-a]indeno[1,2-e]pyrazine-4,10-dione are progressively added to a solution of 14.2 g of tin(II) chloride in 350 ml of concentrated hydrochloric acid stirred at a temperature in the region of 20° C. The reaction mixture is brought to 50° C. for 2 hours, then cooled and poured into 100 ml of ice-cold water. The precipitate thus obtained is filtered, washed with water and acetone and dried under reduced pressure (1 mm Hg, 0.13 kPa). 4.1 g of the expected product are obtained in the form of a greenish solid, the melting point of which is greater than 260° C.

8-Nitro-5H-imidazo[1,2-a]indeno[1,2e-]pyrazine-4,10-dione can be prepared according to the following method: 7.11 g of 5H-imidazo[1,2-a]indeno[1,2e-]pyrazine-4,10-dione are progressively added to 90 ml of concentrated sulphuric acid cooled to 5° C. and then, after stirring for 30 minutes at 10° C., 3.03 g of potassium nitrate are added in a single step. The reaction is continued for 15 hours at a temperature in the region of 20° C. The reaction mixture is run into 500 ml of ice-cold water and the precipitate formed is filtered, washed with water and with acetone and dried. 6.5 g of the expected product are thus obtained in the form of an orangey solid, the melting point of which is greater than 260° C.

5H-Imidazo[1,2-a]indeno[1,2e-]pyrazine-4,10-dione can be obtained in the following way: a suspension of 1.5 g of 10-(hydroxyimino)-5H-imidazo[1,2a-]indeno[1,2e-]pyrazine-4-one in 90 ml of an approximately 5N aqueous hydrochloric acid solution is stirred at boiling point for 7 hours, cooled and then concentrated to dryness under reduced pressure (15 mm Hg, 2kPa) at 70° C. The product obtained (2 g) is dissolved in 50 ml of dimethylformamide and the solution, to which 0.1 g of decolourizing charcoal is added, is filtered and the filter is then washed 3 times with a total of 30 ml of dimethylformamide. The filtrate and the wash are combined, treated with 600 ml of distilled water and centrifuged. The solid is suspended in 20 ml of distilled water, filtered, washed with 20 ml of acetone and dried under reduced pressure (1 mm Hg, 0.13 kPa) at 100° C. The product obtained (1.13 g) is dissolved in 115 ml of dimethyl sulfoxide and the solution, to which 0.1 g of decolourizing charcoal is added, is filtered and the filter is then washed 2 times with a total of 30 ml of dimethyl sulfoxide. The filtrate and the wash are combined, treated with 115 ml of distilled water and centrifuged. The solid is suspended in 20 ml of distilled water, filtered, washed twice with a total of 20 ml of acetone and dried under reduced pressure (1 mm Hg; 0.13 kPa) at 100° C. There is thus obtained 1 g of 5H-imidazo[1,2-a]indeno[1,2-e]pyrazine-4,10-dione in the form of an orangey-red solid melting at 360° C. (decomposition) [N.M.R. spectrum: (220 MHz, $d_6$-DMSO, $\delta$ in ppm): 7.42 and 7.55 (2t, J=7 Hz, 2H, —H7 and —H8), 7.52 and 7.72 (2d, J=7 Hz, each 1H, —H6 and —H9), 7.62 and 8.13 (2d, J=1 Hz, each 1H, —H of the imidazole), 13.60 (broad unresolved peak, 1H, —NH—)].

10-(E-Hydroxyimino)-5H-imidazo[1,2-a]indeno[1,2-e]pyrazine-4-one can be prepared in the following way: 0.4 g of 80% sodium hydride is added to a suspension of 1.1 g of 5H,10H-imidazo[1,2-a]indeno[1,2e-]pyrazine-4-one in 10 ml of anhydrous dimethyl sulfoxide. After stirring for 10 minutes at a temperature in the region of 20° C., a solution of 0.7 g of isoamyl nitrite in 2 ml of anhydrous dimethyl sulfoxide is added dropwise over 5 minutes and the mixture is then stirred for 1 hour at the same temperature. 10 ml of distilled water are slowly added and the mixture is then poured into 120 g of water and of ice, acidified with 1 ml of acetic acid and then centrifuged. After removal of the supernatant solution, the solid is suspended in 25 ml of distilled water, filtered, washed with 10 ml of acetone and dried under reduced pressure (15 mm Hg, 2 kPa) at 20° C. The product obtained (1.5 g) is dissolved in 100 ml of boiling dimethyl formamide and the solution, to which 0.1 g of decolourizing charcoal is added, is filtered while hot, cooled, poured into 800 ml of distilled water and centrifuged. The solid is suspended in 20 ml of distilled water, filtered, washed with 20 ml of acetone and dried under reduced pressure (15 mm Hg, 2 kPa) at 20° C. The product obtained (0.9 g) is dissolved in 75 ml of dimethyl sulfoxide at 20° C. and the solution, to which 0.1 g of decolourizing charcoal is added, is filtered. The filter is washed twice with a total of 20 ml of dimethyl sulfoxide and the filtrate and the wash are then combined, treated with 75 ml of distilled water and centrifuged. The solid is suspended in 25 ml of distilled water, filtered, washed twice with a total of 50 ml of acetone and then dried under reduced pressure (1 mm Hg, 0.13 kPa) at 60° C. There is thus obtained 0.63 g of 10-(E-hydroxyimino)-5H-imidazo[1,2-a]indeno[1,2e-]pyrazine-4-one which decomposes without melting above 300° C. [N.M.R. spectrum: (200 MHz, d₆-DMSO, δ in ppm): 7.40 and 7.48 (2t, J=7 Hz, 2H, —H7 and —H8), 7.60 and 8.00 (2 broad s, each 1H, —H of the imidazole), 7.82 and 8.20 (2d, J=7 Hz, each 1H, —H6 and —H9), 12.70 and 13.00 (2 broad unresolved peaks, each 1H, —NH— and —OH)].

EXAMPLE 44

3 ml of concentrated hydrochloric acid are added dropwise to 0.5 g of 8-[3-(3-nitrophenyl)ureido]-5H,10H-imidazo[1,2-a]indeno[1,2-e]pyrazine-4-one in suspension in 2 ml of methanol. This yellow suspension is then treated with 0.36 g of iron powder and 5 ml of dimethylformamide. The reaction mixture is brought to reflux for 5 hours. After cooling to a temperature in the region of 20° C., the insoluble material is filtered, washed with methanol and dried under partial vacuum (1 mm Hg, 0.13 kPa). There is thus obtained 0.31 g of 8-[3-(3-aminophenyl)ureido]-5H,10H-imidazo[1,2-a]indeno[1,2-e]pyrazine-4-one dihydrochloride dihydrate in the form of an ochre powder, the melting point of which is greater than 260° C. (Analysis $C_{20}H_{16}N_6O_2 \cdot 2.67HCl \cdot 2.64H_2O$, % calculated C: 64.51, H: 4.33, N: 22.57, % found C: 64.1, H: 4.0, N: 22.7).

EXAMPLE 45

0.76 g of 5-trifluoromethoxy-2-(2-ethoxycarbonyl-1H-imidazol-1-yl)indanone and 19 g of ammonium acetate in 30 ml of acetic acid are heated at reflux for 45 minutes. After cooling to a temperature in the region of 20° C., the precipitate formed is filtered, washed with water and dried under reduced pressure (1 mm Hg, 0.13 kPa) at 40° C. There is obtained 0.5 g of 8-trifluoromethoxy-5H,10H-imidazo[1,2-a]indeno[1,2-e]pyrazine-4-one in the form of a beige powder, the melting point of which is greater than 260° C. (Analysis $C_{14}H_8F_3N_3O_2 \cdot 0.9AcOH$, % calculated C: 54.73, H: 2.62, F: 18.55, N: 13.68, % found C: 55.0, H: 2.6, F: 18.3, N: 13.8).

5-Trifluoromethoxy-2-(2-ethoxycarbonyl-1H-imidazol-1-yl)indanone can be obtained according to the following protocol: 1.5 g of ethyl 1H-imidazole-2-carboxylate and 1.6 g of 5-trifluoromethoxy-2-bromoindanone, in solution in 40 ml of toluene, are heated at reflux for 15 hours. After cooling to a temperature in the region of 20° C. and concentration of the reaction mixture to dryness, the crude product is purified by flash chromatography on a silica column, using an ethyl acetate/cyclohexane (75/25 by volume) mixture as eluent. 0.8 g of the expected product is thus isolated in the form of a brown oil used as is in the subsequent syntheses.

5-Trifluoromethoxy-2-bromoindanone can be prepared in the following way: 0.38 ml of bromine, in solution in 15 ml of acetic acid, is added dropwise over 30 minutes to 3.2 g of 5-(trifluoromethoxy)indanone and three drops of concentrated hydrobromic acid in solution in 70 ml of acetic acid. After stirring for 5 hours at a temperature in the region of 20° C., the reaction mixture is poured onto ice and the organic phase extracted with dichloromethane, washed with water and dried. The crude product thus obtained is purified by flash chromatography on a silica column, using a mixture of dichloromethane and cyclohexane (50/50 by volume) as eluent. 1.5 g of the expected product are isolated in the form of a yellow oil used as is in the subsequent syntheses.

5-(Trifluoromethoxy)indanone can be obtained according to the following method: a solution of 6.5 g of the chloride of 3-(3-trifluoromethoxyphenyl)propanoic acid in 30 ml of 1,2-dichloroethane is added dropwise to a suspension, cooled to 0C, of 3.3 g of anhydrous aluminium chloride in 60 ml of the same solvent. The reaction is continued overnight at a temperature in the region of 20° C. The reaction mixture is then poured into ice-cold water and acidified using 1N hydrochloric acid. The organic phase is extracted with ethyl ether, washed with water, dried over magnesium sulphate and then concentrated to dryness under reduced pressure. The crude product thus obtained is purified by flash chromatography on a silica column, using a mixture of dichloromethane and cyclohexane (50/50 by volume) as eluent. 3.4 g of the expected product are obtained in the form of a yellow oil used as is in the subsequent syntheses.

The chloride of 3-(3-trifluoromethoxyphenyl)propanoic acid can be prepared according to the following procedure: 2.2 ml of thionyl chloride are added, dropwise and at a temperature in the region of 20° C., to 6 g of 3-(3-trifluoromethoxyphenyl)propanoic acid in solution in 80 ml of dichloromethane. The reaction mixture is heated at reflux for 2 hours. After cooling to a temperature in the region of 20° C. and concentration to dryness under reduced pressure, 6.5 g of the expected product are obtained in the form of a brown oil used without additional purification in the subsequent syntheses.

3-(3-Trifluoromethoxyphenyl)propanoic acid can be obtained in the following way: 10 g of 3-(trifluoromethoxy)cinnamic acid are dissolved in 170 ml of methanol and brought into the presence of 2.7 g of nickel chloride hexahydrate at 0° C. 7.9 g of sodium borohydride are added dropwise, over approximately 90 minutes, to this brown solution. The reaction mixture is then reheated to a temperature in the region of 20° C. and the reaction continued overnight at the same temperature. The insoluble material is filtered and separated and the filtrate concentrated to dryness under reduced pressure. The residue obtained is taken up in 5% aqueous potassium hydroxide solution, the organic phase extracted with ethyl ether, the aqueous phase then acidified using concentrated hydrochloric acid and the organic phase extracted with ethyl ether. There are thus obtained, after the usual treatment, 7.7 g of the expected acid in the form of a yellow oil used as is in the subsequent syntheses.

EXAMPLE 46

1.3 g of 8-cyano-5H,10H-imidazo[1,2-a]indeno[1,2e-]pyrazine-4-one, in solution in 20 ml of 60% sulphuric acid, are brought to reflux for 2 hours. The reaction mixture is then cooled to a temperature in the region of 20° C. and then poured into 100 ml of ice-cold water. The precipitate formed is filtered, washed with water and then taken up in an aqueous sodium hydroxide solution. The aqueous solution is stirred for 1 hour at 20° C., then filtered and the filtrate acidified using concentrated hydrochloric acid. The precipitate is then filtered and washed with water and then with acetone to lead, after drying under reduced pressure (1 mm Hg, 0.13 kPa), to 0.44 g of 5H,10H-imidazo[1,2-a]indeno[1,2e-]pyrazine-4-one-8-carboxylic acid in the form of a brown powder, the melting point of which is greater than 260° C. [$^1$H N.M.R. spectrum (300 MHz, d₆-(CD₃)₂So, δ in ppm): 4.11 (s, 2H, CH₂ at 10), 7.76 and 8.15 (2 broad s, each 1H, H of the imidazole), 7.95 (d, J=8 Hz, 1H, H₆), 8.05 (broad d, J=8 Hz, 1H, H₇), 8.15 (broad s, 1H, H₉), 12.74 (broad s, 1H, NH at 5)].

8-Cyano-5H,10H-imidazo[1,2-a]indeno[1,2-e]pyrazine-4-one can be obtained in the following way: a solution of 3 g of 5-cyano-2-(2-carboxamido-1H-imidazol-1-yl)indanone in 40 ml of acetic acid is brought to reflux for 15 hours. After cooling to a temperature in the region of 20° C., 100 ml of ethyl ether are added to the reaction mixture and the precipitate formed is filtered, washed with dichloromethane and dried to lead to 1.3 g of the expected product in the form of a brown powder, the melting point of which is greater than 260° C., used as is in the subsequent syntheses.

5-Cyano-2-(2-carboxamido-1H-imidazol-1-yl)indanone can be prepared according to the following procedure: 11 g of 5-cyano-2-(2-ethoxycarbonyl-1H-imidazol-1-yl) indanone, in solution in 200 ml of methanol, are added dropwise to a saturated methanolic ammonia solution (1 liter) which has been cooled to 5° C. After stirring overnight at a temperature in the region of 20° C., the reaction mixture is concentrated to dryness under reduced pressure to lead to 11.3 g of the expected product in the form of a brown powder used without additional purification in the subsequent stages.

5-Cyano-2-(2-ethoxycarbonyl-1H-imidazol-1-yl) indanone can be prepared in the following way: 17.8 g of ethyl 1H-imidazole-2-carboxylate are added to a solution of 15 g of 2-bromo-5-cyanoindanone in 400 ml of toluene and the mixture is brought to reflux for 6 hours. After cooling to a temperature in the region of 20° C., the precipitate is filtered, washed with toluene and the filtrate concentrated to dryness under reduced pressure. The crude product thus obtained is purified by flash chromatography on a silica column, using a mixture of dichloromethane and methanol (98/2 by volume) as eluent. 11 g of the expected product are thus obtained in the form of a brown foam used as is in the subsequent syntheses.

2-Bromo-5-cyanoindanone can be obtained according to the following protocol: a solution of 8.4 ml of bromine in 100 ml of chloroform is added dropwise to a solution of 26 g of 5-cyanoindanone in 600 ml of chloroform cooled to 5° C. The reaction is continued for 3 hours at a temperature in the region of 20° C. and the reaction mixture is then poured into 1.5 liters of a saturated sodium bicarbonate solution. The organic phase is separated by settling, washed with water, dried over sodium sulphate and concentrated to dryness under reduced pressure. The crude product thus obtained is purified by flash chromatography on a silica column, using a mixture of cyclohexane and ethyl acetate (80/20 by volume) as eluent. 17 g of the expected product are obtained in the form of a yellow powder melting at 124° C.

5-Cyanoindanone can be obtained according to the method described by N. L. Allinger and E. S. Jones, J. Org. Chem. 27, 70 (1962).

EXAMPLE 47

A solution of 1.4 g of trimethylsilyl isocyanate in 4 ml of anhydrous dimethylformamide is added dropwise at 20° C. over 5 minutes to a solution of 1.25 g of 8-amino-5H,10H-imidazo[1,2-a]indeno[1,2-e]pyrazine-4-one hydrochloride and 0.8 g of triethylamine in 40 ml of anhydrous dimethylformamide. After stirring for 15 hours at the same temperature, the insoluble material which appears is separated by filtration, successively washed twice with a total of 20 ml of dimethylformamide, twice with a total of 20 ml of acetone, 3 times with a total of 60 ml of distilled water and twice with a total of 10 ml of acetone and then dried under reduced pressure (1 mm Hg, 0.13 kPa) at a temperature in the region of 20° C. There is thus obtained 1 g of 8-ureido-5H,10H-imidazo[1,2-a]indeno[1,2-e]pyrazine-4-one which decomposes without melting above 260° C. (Analysis, % calculated C: 59.78, H: 3.94, N: 24.90, O: 11.38, % found C: 59.5, H: 3.4, N: 25.3).

EXAMPLE 48

1.3 g of 2-tert-butyloxycarbonylaminoethyl isothiocyanate are added to a solution of 0.48 g of 8-amino-5H,10H-imidazo[1,2-a]indeno[1,2-e]pyrazine-4-one in 20 ml of anhydrous dimethylformamide. The solution is stirred for 15 hours at a temperature in the region of 20° C. and for 2 hours 30 minutes at 60° C. and then concentrated to dryness under reduced pressure (15 mm Hg, 2 kPa) at the same temperature. The product obtained is suspended in 50 ml of acetone and the insoluble material is separated by filtration, washed twice with a total of 10 ml of acetone and dried. The product obtained (0.88 g) is chromatographed on 15 g of neutral silica gel (0.040–0.063 mm) contained in a column with a diameter of 2.5 cm, elution being carried out with a chloroform/ethanol/28% aqueous ammonia (75/20/5 by volume) mixture and 100 ml fractions being collected. The fractions containing the expected product are concentrated to dryness under reduced pressure (15 mm Hg, 2 kPa) at 50° C. The product obtained is suspended in 20 ml of a chloroform/methanol (80/20 by volume) mixture, separated by filtration, washed with 5 ml of the same mixture and 5 ml of acetone and then dried. There is thus obtained 0.1 g of 8-[3-(2-tert-butyloxycarbonylaminoethyl)thioureido]-5H,10H-imidazo[1,2-a]indeno[1,2-e]pyrazine-4-one.

0.45 g of 8-[3-(2-tert-butyloxycarbonylaminoethyl) thioureido]-5H,10H-imidazo[1,2-a]indeno[1,2-e]pyrazine-4-one is dissolved in 8 ml of trifluoroacetic acid and the solution is stored for 30 minutes at 20° C. and then concentrated to dryness under reduced pressure (15 mm Hg, 2 kPa) at 30° C. The product obtained is suspended in 20 ml of boiling ethanol and, after cooling to 20° C., separated by filtration, washed with 5 ml of ethanol and twice with a total of 10 ml of acetone and then dried under reduced pressure (1 mm Hg, 0.13 kPa) at 20° C. There is thus obtained 0.32 g of 8-[3-(2-aminoethyl)thioureido]-5H,10H-imidazo[1,2-a]indeno[1,2-e]pyrazine-4-one trifluoroacetate which decomposes without melting above 260° C. (Analysis, % calculated C: 47.58, H: 3.77, F: 12.54, N: 18.49, O: 10.56, S: 7.06, % found C: 47.4, H: 3.3, N: 18.8, S: 7.1).

2-tert-Butyloxycarbonylaminoethyl isothiocyanate can be prepared as described by K. Ariga and E. V. Anslyn, J. Org. Chem., 57 (2), 417 (1992).

EXAMPLE 49

2.1 g of benzoyl isothiocyanate are added to a stirred solution of 1 g of 8-amino-5H,10H-imidazo[1,2-a]indeno[1,2-e]pyrazine-4-one in 40 ml of anhydrous dimethylformamide and stirring is continued for 15 hours at a temperature in the region of 25° C. The insoluble material which appears is separated by filtration, washed twice with a total of 10 ml of methanol and twice with a total of 20 ml of acetone; a first crop of 0.5 g is thus obtained. The filtrate is concentrated to dryness under reduced pressure (15 mm Hg, 2 kPa) at 60° C. and the product obtained is suspended in 50 ml of acetone, separated by filtration, again suspended in 50 ml of methanol, separated by filtration, washed with 5 ml of methanol and then dried; a second crop of 0.64 g is thus obtained. The 2 crops are combined and chromatographed on 20 g of neutral silica gel (0.040–0.063 mm) contained in a column with a diameter of 2.5 cm, elution being carried out with a chloroform/ethanol/28% aqueous ammonia (75/20/5 by volume) mixture and 150 ml fractions being collected.

The fractions containing the expected product are concentrated to dryness under reduced pressure (15 mm Hg, 2 kPa) at 50° C. The product obtained (0.35 g) is suspended in 40 ml of methanol, separated by filtration, washed 3 times with a total of 15 ml of methanol and twice with a total of 10 ml of acetone and dried under reduced pressure (1 mm Hg, 0.13 kPa) at 70° C. There is thus obtained 0.3 g of 8-(3-benzoylthioureido)-5H,10H-imidazo[1,2-e]pyrazine-4-one which decomposes without melting above 260° C.

A suspension of 0.4 g of 8-(3-benzoylthioureido)-5H, 10H-imidazo[1,2a-]indeno[1,2-e]pyrazine-4-one in 10 ml of a 0.12N aqueous sodium hydroxide solution is stirred for 1 hour at 80° C. After cooling to 20° C., the insoluble material is separated by filtration, washed twice with a total of 10 ml of distilled water and 3 times with a total of 15 ml of acetone and then dried under reduced pressure (1 mm Hg, 0.13 kPa) at 20° C. There is thus obtained 0.17 g of 8-thioureido-5H, 10H-imidazo[1,2a-]indeno[1,2-e]pyrazine-4-one which decomposes without melting above 260° C. (Analysis, % calculated C: 56.55, H: 3.73, N: 23.55, O: 5.38, S: 10.78, % found C: 56.9, H: 3.6, N: 23.1, S: 10.0).

EXAMPLE 50

0.16 g of sodium is dissolved in 15 ml of methanol and then a solution of 1.17 g of 8-[3-(2-aminoethyl)-2-methylisothioureido]-5H,10H-imidazo[1,2-a]indeno[1,2-e]pyrazine-4-one trifluoroacetate hydriodide in 25 ml of methanol is added dropwise over 15 minutes at a temperature in the region of 20° C. After stirring for 15 hours at the same temperature, the insoluble material which appears is separated by filtration, washed twice with a total of 10 ml of methanol and twice with a total of 10 ml of ethyl ether and dried under reduced pressure (1 mm Hg, 0.13 kPa) at 50° C. There is thus obtained 0.4 g of 8-[(2-imidazoline-2-yl)amino]-5H,10H-imidazo[1,2-a]indeno[1,2-e]pyrazine-4-one which decomposes without melting above 260° C. (Analysis, % calculated C: 62.74, H: 4.61, N: 27.43, O: 5.22, % found C: 63.1, N: 27.0).

8-[3-(2-Aminoethyl)-2-methylisothioureido]-5H,10H-imidazo[1,2-a]indeno[1,2-e]pyrazine-4-one trifluoroacetate hydriodide can be prepared in the following way: 0.58 g of 8-[3-(2-tert-butoxycarbonylaminoethyl)-2-methylisothioureido]-5H,10H-imidazo[1,2-a]indeno[1,2-e]pyrazine-4-one hydriodide is dissolved in 8 ml of trifluoroacetic acid and the solution is stored for 30 minutes at a temperature in the region of 20° C. and then concentrated to dryness under reduced pressure (15 mm Hg, 2 kPa) at 40° C. The product obtained is dissolved in 50 ml of ethanol and, after crystallization and then addition of 10 ml of ethyl ether, the crystals which appear are separated by filtration, washed twice with a total of 10 ml of ethyl ether and dried under reduced pressure (15 mm Hg, 2 kPa) at 20° C. There is thus obtained 0.55 g of 8-[3-(2-aminoethyl)-2-methylisothioureido]-5H,10H-imidazo[1,2-a]indeno[1,2-e]pyrazine-4-one trifluoroacetate hydriodide, melting at 220° C.

8-[3-(2-tert-Butoxycarbonylaminoethyl)-2-methylisothioureido]-5H,10H-imidazo[1,2-a]indeno[1,2-e]pyrazine-4-one hydriodide can be prepared in the following way: 2.1 g of methyl iodide are added to a stirred solution of 6.2 g of 8-[3-(2-tert-butoxycarbonylaminoethyl)thioureido]-5H,10H-imidazo[1,2-a]indeno[1,2e-]pyrazine-4-one in 200 ml of anhydrous dimethylformamide. After stirring for 2 hours at 40° C., the solution is concentrated to dryness under reduced pressure (1 mm Hg, 0.13 kPa) at 50° C. The product obtained is suspended in 300 ml of methanol, the insoluble material is removed by filtration and the filtrate, to which decolorizing charcoal is added, is again filtered and concentrated to dryness under reduced pressure (15 mm Hg, 2 kPa) at 40° C. The product obtained (8 g) is dissolved in a boiling mixture of 150 ml of ethanol and 200 ml of isopropanol and, after cooling to a temperature in the region of 20° C., the crystals which appear are separated by filtration, washed twice with a total of 20 ml of isopropanol and 3 times with a total of 30 ml of ethyl ether and then dried under reduced pressure (1 mm Hg, 0.13 kPa) at 50° C. There are thus obtained 2.3 g of 8-[3-(2-tert-butoxycarbonylaminoethyl)-2-methylisothioureido]-5H,10H-imidazo[1,2-a]indeno[1,2e-]pyrazine-4-one hydriodide.

EXAMPLE 51

A solution of 1.57 g of 8-amino-5H,10H-imidazo[1,2-a]indeno[1,2-e]pyrazine-4-one in 75 ml of anhydrous dimethylformamide is added dropwise over 15 minutes at a temperature in the region of 20° C. to a suspension of 0.36 g of 80% sodium hydride in 5 ml of anhydrous dimethylformamide. The mixture is then stirred for 1 hour at the same temperature and then 2.1 g of of trimethylsilyl chloride are added dropwise over 5 minutes. The mixture is then stirred for 30 minutes and then 2.1 g of 1,1'-carbonyldiimidazole are added over 5 minutes. After stirring for 4 hours, 2.2 g of pyrrolidine are added dropwise over 10 minutes and the mixture is then stirred for 1 hour at 60° C. and then for 15 hours at a temperature in the region of 20° C. 10 ml of distilled water and 20 ml of acetic acid are then slowly added, the mixture is then stirred for 15 minutes and concentrated to dryness under reduced pressure (1 mm Hg, 0.13 kPa) at 60° C. The product obtained is suspended in 50 ml of distilled water, separated by filtration, washed 4 times with a total of 40 ml of distilled water and 5 times with a total of 50 ml of acetone and then dried under reduced pressure (1 mm Hg, 0.13 kPa) at 50° C. There are thus obtained 1.7 g of 8-[(1-pyrrolidinyl)carbonylamino]-5H,10H-imidazo[1,2-a]indeno[1,2-e]pyrazine-4-one (Analysis, % calculated C: 64.47, H: 5.11, N: 20.88, O: 9.54, % found C: 64.3, H: 4.6, N: 20.6, O: 9.5).

EXAMPLE 52

By carrying out the preparation as in Example 51 but replacing pyrrolidine with azetidine (1.8 g), there are obtained 1.6 g of 8-[(1-azetidinyl)carbonylamino]-5H,10H-imidazo[1,2-a]indeno[1,2-e]-pyrazine-4-one ($^1$H N.M.R. spectrum (300 MHz, $d_6$-$(CD_3)_2SO$, δ in ppm): 2.19 (mt, 2H, $CH_2$), 3.96 (mt, 6H, $NCH_2$ and $CH_2$ at 10), 7.47 (broad d, J=8 Hz, 1H, $H_7$), 7.62 (broad s, 1H, $H_9$), 7.68 (d, J=8 Hz, 1H, $H_6$), 7.82 and 7.97 (2 broad s, each 1H, H of the imidazole), 8.50 (broad s, 1H, ArNH), 12.40 (broad s, 1H, NH at 5).

EXAMPLE 53

1.4 ml of triethylamine and then 1.3 g of propyl isocyanate, in solution in 5 ml of anhydrous dimethylformamide, are added dropwise to a suspension of 1.6 g of 8-amino-5H,10H-imidazo[1,2-a]indeno[1,2-e]pyrazine-4-one dihydrochloride in 35 ml of anhydrous dimethylformamide. The reaction mixture is stirred for 15 hours at a temperature in the region of 20° C. The insoluble material which appears is separated by filtration, washed with 2 ml of dimethylformamide, twice with a total of 10 ml of distilled water and with 5 ml of acetone and then dried under reduced pressure (15 mm Hg, 2 kPa) at 20° C. The product obtained (1 g) is stirred in suspension for 15 minutes in 15 ml of methanol, separated by filtration, washed twice with a total of 4 ml of methanol and dried under reduced pressure (1 mm Hg, 0.13 kPa) at 100° C. There is thus obtained 0.82 g of 8-(3-propylureido)-5H,10H-imidazo[1,2-a]indeno[1,2-e]pyrazine-4-one (Analysis, % calculated C: 63.15, H: 5.30, N: 21.66, O: 9.90, % found C: 62.8, H: 5.5, N: 21.7).

EXAMPLE 54

1.4 ml of triethylamine and then 1.3 g of isopropyl isocyanate, in solution in 5 ml of anhydrous dimethylformamide, are added dropwise to a suspension of 1.6 g of 8-amino-5H,10H-imidazo[1,2-a]indeno[1,2-e]pyrazine-4-one dihydrochloride in 35 ml of anhydrous dimethylformamide. The reaction mixture is stirred for 15 hours at a temperature in the region of 20° C. The insoluble material which appears is separated by filtration, washed with 2 ml of dimethylformamide, twice with a total of 10 ml of distilled water and with 5 ml of acetone and then dried under reduced pressure (15 mm Hg, 2 kPa) at 20° C. The product obtained (1.14 g) is stirred in suspension for 15 minutes in 10 ml of methanol, separated by filtration, washed with 2 ml of methanol and dried under reduced pressure (1 mm Hg, 0.13 kPa) at 100° C. The product obtained (0.75 g) is stirred in suspension for 15 minutes in 15 ml of acetic acid, separated by filtration, washed with 3 ml of acetic acid, twice with a total of 10 ml of distilled water and with 5 ml of acetone and then dried under reduced pressure (1 mm Hg, 0.13 kPa) at 100° C. There is thus obtained 0.52 g of 8-(3-isopropylureido)-5H,10H-imidazo[1,2-a]indeno[1,2-e]pyrazine-4-one (Analysis, % calculated C: 63.15, H: 5.30, N: 21.66, O: 9.90, % found C: 62.9, H: 4.6, N: 21.8).

EXAMPLE 55

1.4 ml of triethylamine and then 1.5 g of butyl isocyanate, in solution in 5 ml of anhydrous dimethylformamide, are added dropwise to a suspension of 1.6 g of 8-amino-5H,10H-imidazo[1,2-a]indeno[1,2e]pyrazine-4-one dihydrochloride in 35 ml of anhydrous dimethylformamide. The reaction mixture is stirred for 15 hours at a temperature in the region of 20° C. The insoluble material which appears is separated by filtration, washed with 2 ml of dimethylformamide, twice with a total of 10 ml of distilled water and with 5 ml of acetone and then dried under reduced pressure (15 mm Hg, 2 kPa) at 20° C. The product obtained (1.2 g) is purified by chromatography on a silica column, elution being carried out with a chloroform/ethanol/28% aqueous ammonia (75/20/5 by volume) mixture. The product obtained (0.66 g) is stirred in suspension for 30 minutes in 10 ml of methanol, separated by filtration, washed twice with a total of 2 ml of methanol and dried under reduced pressure (1 mm Hg, 0.13 kPa) at 100° C. There is thus obtained 0.49 g of 8-(3-butylureido)-5H,10H-imidazo[1,2-a]indeno[1,2-e]pyrazine-4-one (Analysis, % calculated C: 64.08, H: 5.68, N: 20.76, O: 9.48, % found C: 64.1, H: 5.2, N: 20.1).

EXAMPLE 56

1.4 ml of triethylamine and then 1.9 g of 2-chloroethyl isothiocyanate, in solution in 5 ml of anhydrous dimethylformamide, are added dropwise to a suspension of 1.6 g of 8-amino-5H,10H-imidazo[1,2-a]indeno[1,2e-]pyrazine-4-one dihydrochloride in 35 ml of anhydrous dimethylformamide. The reaction mixture is stirred for 15 hours at a temperature in the region of 20° C. The insoluble material which appears is separated by filtration, washed with 2 ml of dimethylformamide, twice with a total of 10 ml of distilled water and with 5 ml of acetone and then dried under reduced pressure (15 mm Hg, 2 kPa) at 20° C. The product obtained (1.7 g) is purified by chromatography on a silica column, elution being carried out with a chloroform/ethanol/28% aqueous ammonia (75/20/5 by volume) mixture. The product obtained (0.78 g) is stirred in suspension for 30 minutes in 10 ml of propanol, separated by filtration, washed twice with a total of 2 ml of propanol and dried under reduced pressure (1 mm Hg, 0.13 kPa) at 100° C. There is thus obtained 0.63 g of 8-[(2-thiazolin-2-yl)amino]-5H,10H-imidazo[1,2-a]indeno[1,2e-]pyrazine-4-one which is partially salified (40%) in the hydrochloride form (Analysis, % calculated C: 56.86, H: 4.00, Cl: 4.20, N: 20.72, O: 4.73, S: 9.49, % found C: 56.9, H: 3.7, Cl: 4.2, N: 20.7, O: 4.4, S: 9.8).

EXAMPLE 57

0.5 ml of triethylamine and then 0.5 g of methyl isocyanate, in solution in 2 ml of anhydrous dimethylformamide, are added dropwise to a suspension of 0.96 g of a 70/30 mixture of 8-amino-5H,10H-imidazo[1,2-a]indeno[1,2-e]pyrazine-4-one hydrochloride and 8-methylamino-5H,10H-imidazo[1,2-a]indeno[1,2-e]pyrazine-4-one hydrochloride respectively in 25 ml of anhydrous dimethylformamide. The reaction mixture is stirred for 15 hours at a temperature in the region of 20° C. The insoluble material which appears is separated by filtration and the filtrate is concentrated to dryness under reduced pressure (1 mm Hg, 0.13 kPa) at 60° C. The product obtained (1.26 g) is stirred in suspension for 30 minutes in 20 ml of distilled water, separated by filtration, washed twice with a total of 10 ml of distilled water and dried under reduced pressure (5 mm Hg, 0.65 kPa) at 100° C. The product obtained (0.14 g) is purified by chromatography on a silica column, elution being carried out with a chloroform/ethanol/28% aqueous ammonia (75/20/5 by volume) mixture. The fractions containing the expected product are concentrated to dryness under reduced pressure (1 mm Hg, 0.13 kPa) at 60° C. There are thus obtained 26 mg of 8-(1,3-dimethylureido)-5H,10H-imidazo[1,2-a]indeno[1,2e-]pyrazine-4-one ($^1$H N.M.R. spectrum (300 MHz, $d_6$-$(CD_3)_2SO$, δ in ppm): 2.57 (d, J=5.5 Hz, 3H, $CH_3$), 3.17 (s, 3H, $ArNCH_3$), 4.00 (s, 2H, $CH_2$ at 10), 5.95 (t, J=5.5 Hz, 1H, NHCO), 7.28 (broad d, J=8 Hz, 1H, $H_7$), 7.50 (broad s, 1H, H9), 7.60 and 7.99 (2 broad s, each 1H, H of the imidazole), 7.85 (d, J=8 Hz, 1H, $H_6$), 12.40 (broad s, 1H, NH at 5). 8-Methylamino-5H,10H-imidazo[1,2-a]indeno[1,2-e]pyrazine-4-one hydrochloride can be prepared in the following way: 14 ml of a 2 mol per liter solution in tetrahydrofuran of the borane-dimethyl sulphide complex are added dropwise, at a temperature in the region of 20° C., to a suspension of 3 g of 8-formylamino-5H,10H-imidazo[1,2-a]indeno[1,2-e]pyrazine-4-one in 155 ml of anhydrous tetrahydrofuran. The mixture is then stirred for 3 hours at boiling point and, after cooling and addition of 155 ml of methanol, saturated with a stream of gaseous hydrochloric acid and again stirred at boiling point for 1 hour and then for 15 hours at a temperature in the region of 20° C. The insoluble material is separated by filtration, washed with 40 ml of methanol and dried under reduced pressure (5 mm Hg, 0.65 kPa) at 40° C. There are thus obtained 2.64 g of a 70/30 mixture respectively of 8-amino-5H,10H-imidazo[1,2-a]indeno[1,2-e]pyrazine-4-one hydrochloride and 8-methylamino-5H,10H-imidazo[1,2-a]indeno[1,2e-]pyrazine-4-one hydrochloride, used as is in the following stage.

8-Formylamino-5H,10H-imidazo[1,2-a]indeno[1,2-e]pyrazine-4-one can be prepared in the following way: the mixture of 171 g of acetic anhydride and 92 g of formic acid is stirred for 2 hours at 55° C. and cooled to a temperature in the region of 20° C. 7.2 g of anhydrous sodium acetate and, in small fractions, 12.7 g of 8-amino-5H,10H-imidazo[1,2-a]indeno[1,2-e]pyrazine-4-one dihydrochloride are then added. The mixture is stirred for 15 hours at a temperature in the region of 20° C. and, after slow addition of 80 ml of distilled water at 5° C., the insoluble material is separated by filtration, washed twice with a total of 160 ml of distilled water and dried under reduced pressure (5 mm Hg, 0.65 kPa) at 80° C. There are thus obtained 8.37 g of 8-formylamino-5H,10H-imidazo[1,2-a]indeno[1,2-e]pyrazine-4-one.

EXAMPLE 58

2.70 ml of triethylamine and then 3.41 g of 2-carbomethoxyphenyl isocyanate, in solution in 30 ml of dimethylformamide, are added dropwise to a suspension of 3 g of 8-amino-5H,10H-imidazo[1,2-a]indeno[1,2-e]pyrazine-4-one hydrochloride in 30 ml of dimethylformamide. The reaction mixture is stirred overnight at a temperature in the region of 20° C. The precipitate formed is filtered, washed with distilled water, acetone and diethyl ether and then dried under reduced pressure (1 mm Hg, 0.13 kPa) at 30° C. The solid thus obtained is taken up in 20 ml of dimethylformamide, filtered, rinsed with 10 ml of dimethylformamide and dried under reduced pressure (1 mm Hg, 0.13 kPa) at 47° C. There are thus obtained 2.45 g of 8-[3-(2-carbomethoxyphenyl)ureido]-5H,10H-imidazo[1,2-a]indeno[1,2-e]pyrazine-4-one in the form of a beige solid, the melting point of which is greater than 260° C. (Analysis $C_{22}H_{17}N_5O_4 \cdot 0.26H_2O \cdot 0.60DMF$, % calculated C: 63.61, H: 4.12, N: 16.86, O: 15.41, % found C: 63.1, H: 4.4, N: 16.3, O: 14.9).

EXAMPLE 59

2.70 ml of triethylamine and then 3.41 g of 3-carbomethoxyphenyl isocyanate, in solution in 30 ml of dimethylformamide, are added dropwise to a suspension of 3 g of 8-amino-5H,10H-imidazo[1,2-a]indeno[1,2-e]pyrazine-4-one hydrochloride in 30 ml of dimethylformamide. The reaction mixture is stirred overnight at a temperature in the region of 20° C. The precipitate formed is filtered, washed with dimethylformamide and distilled water and then dried under reduced pressure (1 mm Hg, 0.13 kPa) at 50° C. The solid thus obtained is taken up in 50 ml of dimethylformamide, filtered, rinsed with dimethylformamide, distilled water and acetone and then dried under reduced pressure (1 mm Hg, 0.13 kPa) at 50° C. There are thus obtained 1.80 g of 8-[3-(3-carbomethoxyphenyl)ureido]-5H,10H-imidazo[1,2-a]indeno[1,2-e]pyrazine-4-one in the form of a purple solid, the melting point of which is greater than 260° C. (Analysis $C_{22}H_{17}N_5O_4 \cdot 0.80H_2O \cdot 0.44DMF$, % calculated C: 63.61, H: 4.12, N: 16.86, O: 15.41, % found C: 63.6, H: 4.0, N: 16.7, O: 15.4).

3-Carbomethoxyphenyl isocyanate can be obtained according to the method described by R. Katakai, J. Org. Chem., 50 715 (1885).

EXAMPLE 60

1 ml of 30% aqueous sodium hydroxide solution is added dropwise, at a temperature in the region of 20° C., to a suspension of 1 g of 8-[3-(3-carbomethoxyphenyl)ureido]-5H,10H-imidazo[1,2-a]indeno[1,2e-]pyrazine-4-one in 35 ml of ethanol. The reaction is continued for 5 hours at 50° C. After cooling, the reaction mixture is concentrated under reduced pressure (1 mm Hg, 0.13 kPa) at 45° C. 10 ml of distilled water and 15 ml of 1N hydrochloric acid are added to the solid thus obtained. After filtration, washing with methanol and then drying under reduced pressure (1 mm Hg, 0.13 kPa) at 40° C., there is obtained 0.9 g of 8-[3-(3-carboxyphenyl)ureido]-5H,10H-imidazo[1,2-a]indeno[1,2-e]pyrazine-4-one hydrochloride in the form of a greenish solid, the melting point of which is greater than 260° C. (Analysis $C_{21}H_{16}ClN_5O_4 \cdot 0.47H_2O$, % calculated C: 57.61, H: 3.68, Cl: 8.10, N: 16.00, O: 14.62, % found C: 57.3, H: 4.0, N: 15.7, O: 14.6).

EXAMPLE 61

2.70 ml of triethylamine and then 3.68 g of 4-carbethoxyphenyl isocyanate, in solution in 30 ml of dimethylformamide, are added dropwise to a suspension of 3 g of 8-amino-5H,10H-imidazo[1,2-a]indeno[1,2-e]pyrazine-4-one hydrochloride in 30 ml of dimethylformamide. The reaction mixture is stirred overnight at a temperature in the region of 20° C. The precipitate formed is filtered, washed with dimethylformamide, distilled water and ethyl ether and then dried under reduced pressure (1 mm Hg, 0.13 kPa) at 42° C. The solid thus obtained is taken up in distilled water, filtered, rinsed with acetone and then dried under reduced pressure (1 mm Hg, 0.13 kPa) at 45° C. There are thus obtained 2.5 g of 8-[3-(4-carbethoxyphenyl)ureido]-5H,10H-imidazo[1,2-a]indeno[1,2-e]pyrazine-4-one in the form of a beige solid, the melting point of which is greater than 260° C. (Analysis $C_{23}H_{19}N_5O_4 \cdot 0.18H_2O \cdot 0.51DMF$, % calculated C: 64.33, H: 4.46, N: 16.31, O: 14.90, % found C: 64.0, H: 4.5, N: 15.5, O: 14.3).

EXAMPLE 62

1.7 ml of 30% aqueous sodium hydroxide solution are added dropwise, at a temperature in the region of 20° C., to a suspension of 1.74 g of 8-[3-(4-carboethoxyphenyl)ureido]-5H,10H-imidazo[1,2-a]indeno[1,2-e]pyrazine-4-one in 55 ml of ethanol. The reaction is continued for 12 hours at 50° C. After cooling the reaction mixture, the precipitate formed is filtered, washed with ethanol and acetone and dried under ordinary pressure at 20° C. The solid thus obtained is taken up in 20 ml of distilled water and acidified with 10 ml of 1N hydrochloric acid. After stirring for 1 hour, the solid is filtered, washed with distilled water, acetone and methanol and then dried under reduced pressure (1 mm Hg, 0.13 kPa) at 45° C. There is thus obtained 0.5 g of 8-[3-(4-carboxyphenyl)ureido]-5H,10H-imidazo[1,2-a]indeno[1,2e-]pyrazine-4-one in the form of an ochre solid, the melting point of which is greater than 260° C. (Analysis $C_{21}H_{15}N_5O_4 \cdot 2.15H_2O$, % calculated C: 62.84, H: 3.77, N: 17.45, O: 15.94, % found C: 62.8, H: 3.5, N: 17.3).

EXAMPLE 63

3.20 ml of triethylamine and then 6.16 g of 4-carbomethoxybenzyl isocyanate, in solution in 36 ml of dimethylformamide, are added dropwise to a suspension of 3.58 g of 8-amino-5H,10H-imidazo[1,2-a]indeno[1,2-e]pyrazine-4-one hydrochloride in 36 ml of dimethylformamide. The reaction mixture is stirred overnight at a temperature in the region of 20° C. The precipitate formed is filtered, washed with distilled water, dimethylformamide and diethyl ether and then dried under reduced pressure (1 mm Hg, 0.13 kPa) at 30° C. The solid thus obtained is taken up in 30 ml of methanol and washed with diethyl ether. After drying, the residue is recrystallized from 200 ml of dimethylformamide and there are thus obtained 1.1 g of 8-[3-(4-carbomethoxybenzyl)ureido]-5H,10H-imidazo[1,2-a]indeno[1,2-e]pyrazine-4-one in the form of a beige solid, the melting point of which is greater than 260° C. (Analysis $C_{23}H_{19}N_5O_4.0.82H_2O.0.46DMF$, % calculated C: 64.33, H: 4.46, N: 16.31, O: 14.90, % found C: 64.0, H: 4.8, N: 16.8 14.3).

4-Carbomethoxybenzyl isocyanate can be obtained according to the method described by R. Katakai, J. Org. Chem., 50, 715 (1885).

EXAMPLE 64

3.9 ml of 30% aqueous sodium hydroxide solution are added dropwise, at a temperature in the region of 20° C., to a suspension of 1.5 g of 8-[3-(4-carbomethoxybenzyl)ureido)-5H,10H-imidazo[1,2-a]indeno[1,2-e]pyrazine-4-one in 52 ml of methanol. The reaction is continued for 20 hours at 50° C. After cooling the reaction mixture, the precipitate formed is filtered, washed with methanol and acetone and dried under ordinary pressure at 20° C. The solid thus obtained is taken up in 20 ml of distilled water and acidified with 4 ml of 6N hydrochloric acid. After stirring for 1 hour, the solid is filtered, washed with distilled water and diethyl ether and then dried under reduced pressure (1 mm Hg, 0.13 kPa) at 45° C. The residue is recrystallized from 80 ml of dimethylformamide and there is thus obtained 0.15 g of 8-[3-(4-carboxy-benzyl)ureido]-5H,10H-imidazo[1,2a-]indeno[1,2-e]-pyrazine-4-one in the form of a pink solid, the melting point of which is greater than 260° C. (Analysis $C_{22}H_{17}N_5O_4.0.05H_2O.2.30DMF$, % calculated C: 63.61, H: 4.12, N: 16.86, O: 15.41, % found C: 63.3, H: 3.4, N: 16.8).

EXAMPLE 65

1.35 ml of triethylamine and then 1.67 g of 2-fluorobenzyl isocyanate, in solution in 15 ml of dimethylformamide, are added dropwise to a suspension of 1.5 g of 8-amino-5H, 10H-imidazo[1,2-a]indeno[1,2-e]pyrazine-4-one hydrochloride in 15 ml of dimethylformamide. The reaction mixture is stirred overnight at a temperature in the region of 20° C. The precipitate formed is filtered, washed with dimethylformamide, distilled water, acetone and diethyl ether and then dried under reduced pressure (1 mm Hg, 0.13 kPa) at 50° C. The solid thus obtained is taken up in 20 ml of dimethylformamide, filtered, rinsed with 40 ml of distilled water and diethyl ether and then dried under reduced pressure (1 mm Hg, 0.13 kPa) at 40° C. There is thus obtained 0.45 g of 8-[3-(2-fluorobenzyl)ureido]-5H,10H-imidazo[1,2-a]indeno[1,2-e]pyrazine-4-one in the form of a purple solid, the melting point of which is greater than 260° C. (Analysis $C_{21}H_{16}FN_5O_2.1.45H_2O$, % calculated C: 64.78, H: 4.14, F: 4.88, N: 17.99, O: 8.22, % found C: 64.7, H: 4.0, F: 4.2, N: 18.3).

2-Fluorobenzyl isocyanate can be obtained according to the method described by R. Katakai, J. Org. Chem., 50, 715 (1885).

EXAMPLE 66

1.8 ml of triethylamine and then 3.88 g of 3-fluorobenzyl isocyanate, in solution in 20 ml of dimethylformamide, are added dropwise to a suspension of 2 g of 8-amino-5H,10H-imidazo[1,2-a]indeno[1,2-e]pyrazine-4-one hydrochloride in 20 ml of dimethylformamide. The reaction mixture is stirred overnight at a temperature in the region of 20° C. The precipitate formed is filtered, washed with distilled water, acetone and diethyl ether and then dried under reduced pressure (1 mm Hg, 0.13 kPa) at 50° C. The solid thus obtained is taken up in 20 ml of dimethylformamide, filtered, rinsed with 30 ml of distilled water and diisopropyl ether and then dried under reduced pressure (1 mm Hg, 0.13 kPa) at 40° C. The residue is recrystallized from 20 ml of dimethylformamide and there is thus obtained 0.38 g of 8-[3-(3-fluorobenzyl)ureido]-5H,10H-imidazo 1,2-a]indeno [1,2e-]pyrazine-4-one in the form of a beige solid, the melting point of which is greater than 260° C. (Analysis $C_{21}H_{16}FN_5O_2.0.56H_2O.0.33DMF$, % calculated C: 64.78, H: 4.14, F: 4.88, N: 17.99, O: 8.22, % found C: 64.9, H: 3.8, F: 4.4, N: 18.8).

3-Fluorobenzyl isocyanate can be obtained according to the method described by R. Katakai, J. Org. Chem., 50, 715 (1885).

EXAMPLE 67

1.35 ml of triethylamine and then 1.67 g of 4-fluorobenzyl isocyanate, in solution in 15 ml of dimethylformamide, are added dropwise to a suspension of 1.5 g of 8-amino-5H, 10H-imidazo[1,2-a]indeno[1,2-e]pyrazine-4-one hydrochloride in 15 ml of dimethylformamide. The reaction mixture is stirred overnight at a temperature in the region of 20° C. The precipitate formed is filtered, washed with distilled water, acetone and diethyl ether and then dried under reduced pressure (1 mm Hg, 0.13 kPa) at 50° C. The solid thus obtained is taken up in 20 ml of dimethylformamide, filtered, rinsed with ethyl ether and acetone and then dried under reduced pressure (1 mm Hg, 0.13 kPa) at 40° C. The residue is recrystallized from 15 ml of dimethylformamide and there is thus obtained 0.2 g of 8-[3-(4-fluorobenzyl)ureido]-5H,10H-imidazo[1,2-a]indeno [1,2e-]pyrazine-4-one in the form of a grey solid, the melting point of which is greater than 260° C. (Analysis $C_{21}H_6FN_5O_2.0.57H_2O.0.93DMF$, % calculated C: 64.78, H: 4.14, F: 4.88, N: 17.99, O: 8.22, % found C: 64.8, H: 3.9, F: 4.3, N: 18.3).

4-Fluorobenzyl isocyanate can be obtained according to the method described by R. Katakai, J. Org. Chem., 50, 715 (1885).

EXAMPLE 68

0.24 g of 9-cyano-5H,10H-imidazo[1,2-a]indeno[1,2-e]pyrazine-4-one and 4 ml of concentrated sulphuric acid are brought to reflux for 2 hours. The reaction mixture is poured into ice-cold water. The precipitate formed is filtered and dried under reduced pressure (1 mm Hg, 0.13 kPa) at 40° C. There are thus obtained 240 mg of 9-carboxy-5H,10H-imidazo[1,2-a]indeno[1,2-e]pyrazine-4-one in the form of a beige solid, the melting point of which is greater than 260° C. (Analysis $C_{14}H_9N_3O_3.1.32H_2O.0.18H_2SO_4$, % calculated C: 62.92, H: 3.39, N: 15.72, O: 17.96, % found C: 62.5, H: 3.2, N: 15.5, O: 17.6).

9-Cyano-5H,10H-imidazo[1,2-a]indeno[1,2-e]pyrazine-4-one can be obtained in the following way: 1 g of 1-[2-(4-cyano-1-oxoindanyl)]imidazole-2-carboxamide is dissolved in 10 ml of acetic acid and the solution is brought to reflux for 22 hours. After cooling the reaction mixture, the suspension is filtered and washed with 5 ml of acetic acid, distilled water and ethyl ether. The solid is dried under reduced pressure (15 mm Hg, 2 kPa) at 30° C. and there is thus obtained 0.4 g of 9-cyano-5H,10H-imidazo[1,2-a]indeno[1,2-e]-pyrazine-4-one melting at a temperature greater than 260° C. (Analysis $C_{14}H_8N_4O.0.21H_2O$, % calculated C: 67.74, H: 3.25, N: 22.57, O: 6.45, % found C: 68.1, H: 3.3, N: 22.6, O: 6.7).

1-[2-(4-Cyano-1-oxoindanyl)]imidazole-2-carboxamide can be obtained in the following way: a solution of 1.5 g of ethyl 1-[2-(4-cyano-1-oxoindanyl)]-imidazole-2-carboxylate in 130 ml of methanol is kept saturated for 1 hour at a temperature in the region of 20° C. with a stream of ammonia gas. The reaction mixture is then concentrated to dryness under reduced pressure (15 mm Hg, 2 kPa) at 50° C. There are thus obtained 1.2 g of 1-[2-(4-cyano-1-oxoindanyl)]imidazole-2-carboxamide, melting at 216° C.

Ethyl 1-[2-(4-cyano-1-oxoindanyl)]imidazole-2-carboxylate can be obtained in the following way: a mixture of 3.92 g of ethyl imidazole-2-carboxylate and 3.4 g of 2-bromo-4-cyano-1-indanone is heated at 130° C. for 20 minutes, cooled to 20° C. and dissolved in 20 ml of dichloromethane. The mixture is then concentrated to dryness under reduced pressure (15 mm Hg, 2 kPa) at 40° C. The residue thus obtained is purified by flash chromatography on a silica column, under a stream of nitrogen at moderate pressure (0.5 bar) with a dichloromethane/methanol (95/5 by volume) mixture as eluent. There are thus obtained 1.5 g of ethyl 1-[2-(4-cyano-1-oxoindanyl)] imidazole-2-carboxylate, melting at 159° C.

2-Bromo-4-cyano-1-indanone can be obtained in the following way: a solution of 6.9 g of 4-cyano-1-indanone and 95 ml of chloroform is cooled to 5° C. A solution of 7.04 g of bromine and 20 ml of chloroform is then added dropwise over 2 hours at a temperature of between 0° and 5° C. After having left the reaction mixture stirring for 1 hour while retaining the temperature of introduction, the solution is left to return to room temperature and stirred further overnight. The reaction mixture is then concentrated to dryness under reduced pressure (15 mm Hg, 2 kPa) at 40° C. The residue thus obtained is purified by flash chromatography on a silica column, under a stream of nitrogen at moderate pressure (0.5 bar) with an ethyl ether/cyclohexane (20/80 by volume) mixture as eluent. There are thus obtained 3.43 g of 2-bromo-4-cyano-1-indanone, melting at 124° C.

4-Cyano-1-indanone can be prepared in the following way: 12.61 g of copper cyanide are added to a solution of 10 g of 4-bromo-1-indanone in 94 ml of dimethylformamide, the reaction mixture is then brought to reflux for 6 hours and stirred at a temperature in the region of 20° C. overnight. The solution is then poured into an aqueous sodium cyanide solution (5%), stirred for 15 minutes and extracted with three times 500 ml of ethyl acetate. The organic phases are dried over sodium sulphate and concentrated under reduced pressure (15 mm Hg, 2 kPa) at 40° C. The residue thus obtained is purified by flash chromatography on a silica column, under a stream of nitrogen at moderate pressure (0.5 bar) with an ethyl acetate/cyclohexane (20/80 by volume) mixture as eluent. There are thus obtained 5.9 g of 4-cyano-1-indanone, melting at 122° C.

4-Bromo-1-indanone can be prepared as described by F. G. Holliman, F. G. Manne and D. A. Thornton, J. Chem. Soc., 9 (1960).

EXAMPLE 69

0.5 g of 9-carboxy-5H,10H-imidazo[1,2-a]indeno[1,2e-]pyrazine-4-one and 14.2 ml of thionyl chloride are brought to reflux for 3 hours. After cooling the reaction mass and distillation of the excess thionyl chloride, 20 ml of toluene are added. Gaseous ammonia is sparged into the solution over 15 minutes at a temperature in the region of 5° C. After having left to stir overnight at a temperature in the region of 20° C., sparging is again carried out with gaseous ammonia for 15 minutes and the reaction mixture is brought to reflux for two hours. After cooling, the reaction mixture is concentrated under reduced pressure (1 mm Hg, 0.13 kPa) at 40° C. The residue is taken up in 10 ml of distilled water, filtered and washed with distilled water and acetone. The solid thus obtained is taken up in 10 ml of distilled water and 5 ml of concentrated hydrochloric acid and is stirred overnight at a temperature in the region of 20° C. The precipitate formed is filtered, washed with 40 ml of a solution of hydrochloric acid in ethyl ether and dried under reduced pressure (1 mm Hg, 0.13 kPa) at 40° C. There is thus obtained 0.27 g of 9-carboxamido-5H,10H-imidazo[1,2-a]indeno[1,2-e]pyrazine-4-one hydrochloride in the form of a brown solid, the melting point of which is greater than 260° C. (Analysis $C_{14}H_{11}ClN_4O_2 \cdot 0.77H_2O$, % calculated C: 55.55, H: 3.66, Cl: 11.71, N: 18.51, O: 10.57, % found C: 52.2, H: 3.9, Cl: 11.1, N: 17.3).

EXAMPLE 70

0.4 g of 9-carboxy-5H,10H-imidazo[1,2-a]indeno[1,2e-]pyrazine-4-one and 3.2 ml of thionyl chloride are brought to reflux for 2 hours. After cooling the reaction mass and distillation of the excess thionyl chloride, 10 ml of toluene are added. 2 ml of diethylamine are added dropwise at a temperature in the region of 20° C. and the reaction mixture is brought to reflux for 3 hours. After cooling, the reaction mixture is taken up in 10 ml of distilled water and stirred for 1 hour. The precipitate formed is filtered and washed with distilled water and ethyl ether. The solid thus obtained is recrystallized from 2 ml of dimethylformamide and there is thus obtained 0.10 g of 9-(N-diethylcarboxamido)-5H,10H-imidazo[1,2-a]indeno[1,2-e]pyrazine-4-one in the form of a pink solid, the melting point of which is greater than 260° C. (Analysis $C_{18}H_{18}N_4O_2 \cdot 1.33H_2O$, % calculated C: 67.07, H: 5.63, N: 17.38, O: 9.93, % found C: 67.8, H: 5.5, N: 17.7).

EXAMPLE 71

0.6 g of 9-carboxy-5H,10H-imidazo[1,2-a]indeno[1,2e-]pyrazine-4-one and 10 ml of thionyl chloride are brought to reflux for 1 hour and 30 minutes. After cooling the reaction mass and distillation of the excess thionyl chloride, 20 ml of toluene are added. 20 ml of a solution of ethylamine in toluene (10%) are added dropwise at a temperature in the region of 20° C. After having left to stir overnight at a temperature in the region of 20° C., the reaction mixture is concentrated under reduced pressure (1 mm Hg, 0.13 kPa) at 55C. The residue is taken up in 10 ml of distilled water, filtered and washed with distilled water and ethanol. The solid thus obtained is recrystallized from 10 ml of dimethylformamide, filtered, washed with diisopropyl ether and dried under reduced pressure (1 mm Hg, 0.13 kPa) at 50° C. There is thus obtained 0.17 g of 9-(N-ethylcarboxamido)-5H,10H-imidazo[1,2-a]indeno[1,2e-]pyrazine-4-one in the form of a beige solid, the melting point of which is greater than 260° C. (Analysis $C_{16}H_{14}N_4O_2 \cdot 0.88H_2O$, % calculated C: 65.30, H: 4.79, N: 19.04, O: 10.87, % found C: 64.7, H: 4.5, N: 18.7).

EXAMPLE 72

3.5 g of p-nitrophenyl-N-methylcarbamate are added to a suspension of 1 g of 9-amino-5H,10H-imidazo[1,2-a]indeno [1,2-e]pyrazine-4-one in 55 ml of dimethylformamide. After heating for 4 hours at reflux, the reaction mixture is poured into 500 ml of ice-cold water. The solution obtained is extracted 3 times with 150 ml of dichloromethane and it is then evaporated. The residue is suspended in 50 ml of 0.5N hydrochloric acid and it is filtered. There are thus obtained 62 mg of 9-(3-methylureido)-5H,10H-imidazo[1,2-a]indeno[1,2e-]pyrazine-4-one in the form of a beige solid melting above 260° C. [$^1$H N.M.R. spectrum (250 MHz, d$_6$-($_c$D$_3$δ)$_2$SOn ppm): 2.70 (s, 3H, NCH$_3$), 4.01 (s, 2H, CH$_2$ at 10), 6.56 (broad unresolved peak, 1H, CONH), 7.37 (t, J=8 Hz, 1H, H$_7$), 7.60 and 7.78 (2 broad d, each 1H, H$_6$ and H$_8$), 8.00 and 8.17 (2 broad s, each 1H, H of the imidazole), 8.54 (broad s, 1H, ArNHCO), 13.07 (broad unresolved peak, 1H, NH at 5)].

p-Nitrophenyl-N-methylcarbamate can be prepared as described by T. Konakahara et al., Synthesis, 103 (1993).

EXAMPLE 73

4.1 g of p-methoxybenzyl isocyanate, in solution in 15 ml of 1,4-dioxane, are added to a suspension of 1.5 g of 8-amino-5H,10H-imidazo[1,2-a]indeno[1,2-e]pyrazine-4-one in 15 ml of 1,4-dioxane maintained under nitrogen. After stirring for 18 hours at a temperature in the region of 20° C., the reaction mixture is filtered on sintered glass. The solid is triturated with 100 ml of 0.1N hydrochloric acid. The supernatant is removed and the residue is suspended in 200 ml of methanol. The mixture is heated at reflux for 15 hours and it is then filtered. There are thus obtained 220 mg of 8-[3-(4-methoxybenzyl)ureido]- 5H,10H-imidazo[1,2-a]indeno[1,2e-]pyrazine-4-one in the form of a brown solid melting above 260° C. ($^1$H N.M.R. spectrum (250 MHz, d$_6$-(CD$_3$)$_2$SO, δ in ppm): 3.75 (s, 2H, CH$_2$ at 10), 4.00 (s, 3H, OCH$_3$), 4.26 (d, J=6 Hz, 2H, ArCH$_2$N), 678 (t, J=6 Hz, 1H, NHCO), 6.90 (d, J=8 Hz, 2H, aromatic H ortho to OCH$_3$), 7.00 (broad d, J=8 Hz, 1H, H$_7$), 7.22–7.75 and 7.88 (3 broad s, each 1H, H of the imidazole and H$_9$), 7.28 (d, J=8 Hz, 2H, aromatic H meta to OCH$_3$), 7.32 (d, J=8 Hz, 1H, H$_6$), 9.00 (broad unresolved peak, 1H, ArNH), 12.64 (broad unresolved peak, 1H, NH at 5)].

p-Methoxybenzyl isocyanate can be prepared according to the method described by R. Katakai, J. Org. Chem., 50, 715 (1985).

EXAMPLE 74

1.2 ml of triethylamine and then 0.65 ml of methanesulphonyl chloride are added to a suspension of 1 g of 8-amino-5H,10H-imidazo[1,2a-]indeno[1,2-e]pyrazine-4-one in 20 ml of dimethylformamide maintained under nitrogen. After stirring for 15 hours at a temperature in the region of 20° C., 0.32 ml of methanesulphonyl chloride is again added. The reaction is continued for 4 hours at the same temperature. The reaction mixture is then filtered on sintered glass and rinsed successively with 10 ml of dimethylformamide and two times 10 ml of distilled water. There are thus obtained 600 mg of 8-methylsulphonamido-5H,10H-imidazo[1,2a-]indeno[1,2e-]pyrazine-4-one in the form of a brown solid melting above 260° C. [$^1$H N.M.R. spectrum (400 MHz, d$_6$-(CD$_3$)$_2$SO, δ in ppm): 3.02 (s, 3H, SO$_2$CH$_3$), 4.02 (s, 2H, CH$_2$ at 10), 7.25 (dd, J=8 and 2 Hz, 1H, H$_7$), 7.45 (broad s, 1H, H$_9$), 7.68 and 7.95 (2s, each 1H, H of the imidazole), 7.82 (d, J=8 Hz, 1H, H$_6$), 9.83 (broad unresolved peak, 1H, ArNH), 12.34 (broad unresolved peak, 1H, NH at 5)].

EXAMPLE 75

0.6 ml of triethylamine and then 0.45 ml of dimethylsulphamoyl chloride are added to a solution of 0.5 g of 8-amino-5H,10H-imidazo[1,2-a]indeno[1,2-e]pyrazine-4-one in 15 ml of 1,3-dimethyl-2-imidazolidinone maintained under nitrogen. After stirring for 15 hours at a temperature in the region of 20° C., 0.6 ml of triethylamine and then 0.22 ml of dimethylsulphamoyl chloride are again added. The reaction is continued for 15 hours at the same temperature. The reaction mixture is then filtered on sintered glass. 150 ml of ethyl acetate are added to the filtrate and the precipitate is collected on sintered glass. The solid is crystallized from a mixture of 30 ml of 1,4-dioxane and 20 ml of distilled water. There are thus obtained 120 mg of 8-(N,N-dimethylaminosulphonamido)-5H,10H-imidazo[1,2a-]indeno[1,2e-]pyrazine-4-one in the form of a brown solid melting above 260° C. [$^1$H N.M.R. spectrum (300 MHz, d$_6$-($_c$D$_3$δ)$_2$SO in ppm): 2.72 (s, 6H, SO$_2$N(CH$_3$)$_2$), 4.02 (s, 2H, CH$_2$ at 10), 7.25 (broad d, J=8 Hz, 1H, H$_7$), 7.42 (broad s, 1H, H$_9$), 7.73 and 8.05 (2s, each 1, H of the imidazole), 7.79 (d, J=8 Hz, 1H, H$_6$), 10.05 (broad unresolved peak, 1H, ArNH), 12.64 (broad unresolved peak, 1H, NH at 5)].

The medicaments according to the invention consist of a compound of formula (I) or a salt of such a compound, in the pure state or in the form of a composition in which it is combined with any other pharmaceutically compatible product, which can be inert or physiologically active. The medicaments according to the invention can be used orally, parenterally, rectally or topically.

Tablets, pills, powders (gelatin capsules or cachets) or granules can be used as solid compositions for oral administration. In these compositions, the active principle according to the invention is mixed with one or a number of inert diluents, such as starch, cellulose, sucrose, lactose or silica, under a stream of argon. These compositions can also comprise substances other than the diluents, for example one or a number of lubricating agents such as magnesium stearate or talc, a colouring agent, a coating (dragées) or a varnish.

Pharmaceutically acceptable solutions, suspensions, emulsions, syrups and elixirs containing inert diluents such as water, ethanol, glycerol, vegetable oils or paraffin oil can be used as liquid compositions for oral administration. These compositions can comprise substances other than the diluents, for example wetting, sweetening, thickening, flavouring or stabilizing substances.

The sterile compositions for parenteral administration can preferably be suspensions, emulsions or aqueous or non-aqueous solutions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which contain, besides the active product, excipients such as cocoa butter, semi-synthetic glycerides or poly(ethylene glycol)s.

The compositions for topical administration can be, for example, creams, lotions, eye drops, mouth washes, nose drops or aerosols.

In human therapeutics, the compounds according to the invention are particularly useful for the treatment and/or the prevention of conditions which require the administration of an antagonist of the AMPA receptor or of an antagonist of the NMDA receptor. These compounds are especially useful for treating or preventing all ischaemias and in particular cerebral ischaemia, the effects due to anoxia, the development of neurodegenerative diseases, Huntington's chorea, Alzheimer's disease, amyotrophic lateral sclerosis, olivopontocerebellar atrophy and Parkinson's disease, with respect to epileptogenic and/or convulsive symptoms, for the treatment of cerebral and spinal traumas, traumas related to degeneration of the inner ear or of the retina, anxiety, depression, schizophrenia, Tourette's syndrome or hepatic encephalopathy, as analgesics, anti-inflammatories, antianorexics, antimigraines or antiemetics and for treating poisonings by neurotoxins or other agonist substances of the NMDA receptor, as well as the neurological disorders associated with viral diseases such as AIDS, rabies, measles and tetanus. These compounds are also useful for preventing symptoms of withdrawal from drugs and from alcohol and inhibiting addiction to and dependence on opiates as well as in the treatment of deficiencies related to mitochondrial anomalies such as mitochondrial myopathy, Leber's syndrome, Wernicke's encephalopathy, Rett's syndrome, homocysteinaemia, hyperprolinaemia, hydroxybutiricaminoaciduria, saturnine encephalopathy (chronic lead poisoning) and sulphite oxidase deficiency.

The doses depend on the desired effect, on the duration of treatment and on the administration route used; they are generally between 10 mg and 100 mg per day orally for an adult with unit doses ranging from 5 mg to 50 mg of active substance.

Generally, the doctor will determine the appropriate dosage depending on the age, weight and all the other factors specific to the subject to be treated.

The following examples illustrate compositions according to the invention:

Example A

Gelatin capsules containing 50 mg of active product are prepared, according to the usual technique, which have the following composition:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

Example B

Tablets containing 50 mg of active product are prepared, according to the usual technique, which have the following composition:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) qs 1 coated tablet completed to | 245 mg |

Example C

An injectable solution containing 10 mg of active product is prepared which has the following composition:

| | |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water q.s. | 4 ml |

What is claimed is:

1. A compound of formula (I):

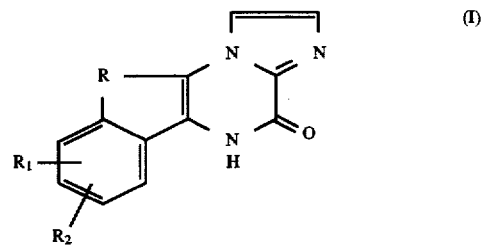

in which

R represents a C=$R_3$, C($R_4$)$R_5$ or CH—$R_6$ radical, $R_1$ represents a hydroxyl, polyfluoroalkoxy, carboxyl, alkoxycarbonyl, —NH—CHO, —NH—CO—N(alk)Ar, in which Ar is optionally substituted by one or a number of substituents selected from halogen atoms and alkyl, alkoxy, nitro, amino, hydroxyl, -alk-$NH_2$, —COO$R_{21}$, cyano and -alk-COO$R_{21}$ radicals, —N(alk)-CO—N$R_8R_9$, —N(alk-Ar)—CO—N$R_8R_9$, —NH—CO—N$R_9R_{12}$, —NH—CS—N$R_8R_9$, —N(alk)-CS—N$R_8R_9$, —NH—CO—$R_{10}$, —NH—CS—$R_{20}$, —NH—C(=N$R_{21}$)—N$R_7R_9$, —N(alk)-C(=N$R_{21}$)—N$R_7R_9$, —NH—$SO_2$—N$R_7R_9$, —N(alk)-$SO_2$—N$R_7R_9$, —CO—N$R_7R_9$, —NH—$SO_2$—$CF_3$, —NH—$SO_2$-alk, —N$R_9R_{11}$, —S(O)$_m$-alk-Ar, —$SO_2$—N$R_7R_9$, 2-oxo-1-imidazolidinyl, in which the 3-position is optionally substituted by an alkyl radical, or 2-oxo-1-perhydropyrimidinyl, in which the 3-position is optionally substituted by an alkyl radical, $R_2$ represents a hydrogen or halogen atom or an alkyl, alkoxy, amino, —NH—CO—NH—Ar, —N=CH—N(alk)alk', nitro, cyano, phenyl, imidazolyl, acylamino, $SO_3H$, hydroxyl, polyfluoroalkoxy, carboxyl, alkoxycarbonyl, —NH—CHO, —NH—CO—N(alk)Ar, in which Ar is optionally substituted by one or a number of substituents selected from halogen atoms and alkyl, alkoxy, nitro, amino, hydroxyl, -alk-$NH_2$, —COO$R_{21}$, cyano and -alk-COO$R_{21}$ radicals, —N(alk)-CO—N$R_8R_9$, —N(alk-Ar)—CO—N$R_8R_9$, —NH—CO—N$R_9R_{12}$, —NH—CS—N$R_8R_9$, —N(alk)-CS—N$R_8R_9$, —NH—CO—$R_{10}$, —NH—CS—$R_{20}$, —NH—C(=N$R_{21}$)—N$R_7R_9$, —N(alk)-C(=N$R_{21}$)—N$R_7R_9$, —NH—$SO_2$—N$R_7R_9$, —N(alk)-$SO_2$—N$R_7R_9$, —CO—N$R_7R_9$, —NH—$SO_2$—$CF_3$, —NH—$SO_2$-alk, —N$R_9R_{11}$, —S(O)$_m$-alk-Ar, —$SO_2$—N$R_7R_9$, 2-oxo-1-imidazolidinyl, in which the 3-position is optionally substituted by an alkyl radical, or 2-oxo-1-perhydropyrimidinyl, in which the 3-position is optionally substituted by an alkyl radical, $R_3$ represents an oxygen atom or an NOH, NO-alk-COOX or CH—$R_{13}$ radical, $R_4$ represents an alkyl, -alk-Het or -alk-Ar radical, $R_5$ represents an alkyl radical having 1 to 11 carbon atoms in a straight or branched chain, an -alk-Het or -alk-Ar radical, or else $R_4$ and $R_5$, together with the carbon atom to which they are attached, form a cycloalkyl radical, $R_6$ represents a hydrogen atom, radical, a hydroxyl radical, an alkyl radical having 1 to 11 carbon atoms in a straight or branched chain, an —$NR_{14}R_{15}$, -alk-OH, -alk-$NR_{14}R_{15}$, -alk-Ar or -alk-Het radical, $R_7$ represents a hydrogen atom or an alkyl radical, $R_8$ represents a hydrogen atom or an alkyl, -alk-$COOR_{21}$, -alk-Het", -alk-$NR_9R_7$, phenylalkyl, in which the phenyl ring is optionally substituted by one or a number of substituents selected from halogen atoms and alkyl, alkoxy, nitro, amino, hydroxyl, -alk-$NH_2$, —$COOR_{21}$, cyano and -alk-$COOR_{21}$ radicals, phenyl, optionally substituted by one or a number of substituents selected from halogen atoms and alkyl, alkoxy, nitro, amino, hydroxyl, -alk-$NH_2$, —$COOR_{21}$ cyano and -alk-$COOR_{21}$ radicals, or -Het" radical, $R_9$ represents a hydrogen atom or an alkyl radical, $R_{10}$ represents an alkyl (5–9 C in a straight or branched chain), alkoxy, -alk-$COOR_{21}$, -alk-Het", -alk-$NR_9R_7$, phenylalkyl, in which the phenyl ring is optionally substituted by one or a number of substituents selected from halogen atoms and alkyl, alkoxy, nitro, amino, hydroxyl, -alk-$NH_2$, —$COOR_{21}$ cyano and -alk-$COOR_{21}$ radicals, phenyl, optionally substituted by one or a number of substituents selected from halogen atoms and alkyl, alkoxy, nitro, amino, hydroxyl, -alk-$NH_2$, —$COOR_{21}$ cyano and -alk-$COOR_{21}$ radicals, or -Het" radical, $R_{11}$ represents an alkyl or Het" radical, $R_{12}$ represents a hydrogen atom or an alkyl, -alk-$COOR_{21}$, -alk-Het", -alk-$NR_9R_7$, phenylalkyl in which the phenyl ring is optionally substituted by one or a number of substituents selected from halogen atoms, alkyl, alkoxy, nitro, amino, hydroxyl, -alk-$NH_2$, —$COOR_{21}$, cyano and -alk-$COOR_{21}$ radicals; phenyl substituted by one or a number of substituents selected from halogen atoms, alkyl, alkoxy, nitro, amino, hydroxyl, -alk-$NH_2$, —$COOR_{21}$ cyano and -alk-$COOR_{21}$, radicals; or -Het" radical, $R_{13}$ represents a hydroxyl, alkyl, phenyl, -alk-Ar, -alk-Het, —$NR_{16}R_{17}$ or -Het radical, $R_{14}$ and $R_{15}$, which are identical or different, each represent an alkyl radical or else $R_{14}$ represents a hydrogen atom and $R_{15}$ represents a hydrogen atom or an alkyl, —$COR_{18}$, —$CSR_{19}$ or —$SO_2R_{20}$ radical, $R_{16}$ and $R_{17}$, which are identical or different, each represent an alkyl or cycloalkyl radical, $R_{18}$ represents an alkyl, cycloalkyl, phenyl, —COO-alk, —$CH_2$—$COOR_{21}$, —$CH_2$—$NH_2$, —NH-alk, —$NH_2$, —NH—Ar or —NH-Het radical, $R_1$ represents an —NH-alk, —NH—Ar, —$NH_2$ or —NH-Het radical, $R_{20}$ represents an alkyl or phenyl radical, $R_{21}$ represents a hydrogen atom or an alkyl radical, X represents a hydrogen atom or an alkyl radical, alk represents an alkyl or alkylene radical, alk' represents an alkyl radical, m is equal to 0, 1 or 2, Ar represents a phenyl radical, Het represents a pyridyl, furyl or pyrimidinyl ring, Het" represents furyl, pyridyl, pyrimidinyl, thiazolinyl, pyrazinyl, thiazolyl, triazolyl, tetrazolyl, imidazolinyl, morpholinyl, imidazolyl, pyrrolyl, pyrrolidinyl, azetidinyl, piperazinyl, piperidinyl, thenyl, oxazolyl or oxazolinyl ring, each of said rings optionally being substituted by one or more alkyl, phenyl or phenylalkyl radicals, it being understood that, except where otherwise mentioned, the alkyl and alkoxy radicals and portions of radicals contain 1 to 6 straight- or branched-chain carbon atoms, the acyl portions of radicals contain 2 to 4 carbon atoms including the carbonyl carbon and the cycloalkyl radicals contain 3 to 6 carbon atoms, an isomer of a compound of formula (I) in which $R_2$ represents an —N=CH—N(alk)alk' radical and/or $R_3$ represents an NOH, NO-alk-COOX or CH—$R_{13}$ radical, an enantiomer or diastereoisomer of a compound of formula (I) in which R represents a $C(R_4)R_5$, in which $R_4$ is other than $R_5$, or CH—$R_6$ radical, or a salt of one of said compounds.

2. A pharmaceutical composition comprising a pharmaceutically effective amount for antagonizing at least one AMPA or NMDA receptor of at least one compound according to claim 1 or a salt thereof, together with a pharmaceutically acceptable carrier.

3. A compound selected from:

9-phenylacetamido-5H,10H-imidazo[1,2-a]indeno-[1,2-e]pyrazine-4-one, 8-ethoxycarbonylamino-5H,10H-imidazo[1,2-a]indeno-[1,2-e]pyrazine-4-one, 8-[3-(3-cyanophenyl)ureido]-5H,10H-imidazo[1,2-a]-indeno[1,2-e]pyrazine-4-one, 8-[3-(3-methoxyphenyl)ureido]-5H,10H-imidazo[1,2-a]-indeno[1,2-e]pyrazine-4-one, 8-phenylacetamido-5H,10H-imidazo[1,2-a]indeno-[1,2-e]pyrazine-4-one, 8-(3-phenylethylureido)-5H,10H-imidazo[1,2-a]indeno-[1,2-e]pyrazine-4-one, 8-(3-methylureido)-5H,10H-imidazo[1,2-a]indeno-[1,2-e]pyrazine-4-one, 8-(3-benzylureido)-5H,10H-imidazo[1,2-a]indeno-[1,2-e]pyrazine-4-one, 8-(3-tert-butylureido)-5H,10H-imidazo[1,2-a]indeno-[1,2-e]pyrazine-4-one, 8-(3-phenylpropionamido)-5H,10H-imidazo[1,2-a]indeno-[1,2-e]pyrazine-4-one, 8-benzamido-5H,10H-imidazo[1,2-a]indeno[1,2-e]-pyrazine-4-one, 8-(4-phenylbutyrylamino)-5H,10H-imidazo[1,2-a]indeno-[1,2-e]pyrazine-4-one, 8-(5-phenylvalerylamino)-5H,10H-imidazo[1,2-a]indeno-[1,2-e]pyrazine-4-one, 8-(3-ethoxycarbonylmethylureido)-5H,10H-imidazo-[1,2-a]indeno[1,2-e]pyrazine-4-one, 8-(3-carboxymethylureido)-5H,10H-imidazo[1,2-a]-indeno[1,2-e]pyrazine-4-one, 8-(3,3-dimethylureido)-5H,10H-imidazo[1,2-a]indeno-[1,2-e]pyrazine-4-one, 8-hydroxy-5H,10H-imidazo[1,2-a]indeno[1,2-e]pyrazine-4-one, 8-(3-aminopropionamido)-5H,10H-imidazo[1,2-a]indeno-[1,2-e]pyrazine-4-one, 8-aminoacetamido-5H,10H-imidazo[1,2-a]indeno[1,2-e]-pyrazine-4-one, 8-[3-(3-nitrophenyl)ureido]-5H,10H-imidazo[1,2-a]-indeno[1,2-e]pyrazine-4-one, 8-[3-(2-methoxyphenyl)ureido]-5H,10H-imidazo[1,2-a]-indeno[1,2-e]pyrazine-4-one, 8-[3-(2-nitrophenyl)ureido]-5H,10H-imidazo[1,2-a]-indeno[1,2-e]pyrazine-4-one, 8-[3-(4-aminophenyl)ureido]-5H,10H-imidazo[1,2-a]-indeno[1,2-e]pyrazine-4-one, 8-[3-(4-methoxyphenyl)ureido]-5H,10H-imidazo[1,2-a]-indeno[1,2-e]pyrazine-4-one, 8-(4-methylpentanoyl)amino-5H,10H-imidazo[1,2-a]-indeno[1,2-e]pyrazine-4-one, N,N-dimethyl-4-oxo-4,5-dihydro-10H-imidazo[1,2-a]-indeno[1,2-e]pyrazine-8-sulphonamide, 8-(3-phenylthioureido)-5H,10H-imidazo[1,2-a]indeno-[1,2-e]pyrazine-4-one, 8-(3-methylthioureido)-5H,10H-imidazo[1,2-a]indeno-[1,2-e]pyrazine-4-one, 8-(2-oxo-1-imidazolinyl)-5H,10H-imidazo[1,2-a]-indeno[1,2-e]pyrazine-4-one, 8-formamido-5H,10H-imidazo[1,2-a]indeno[1,2-e]-pyrazine-4-one, 8-(3-ethoxycarbonylpropionylamino)-5H,10H-imidazo-[1,2-a]indeno[1,2-e]pyrazine-4-one, 8-[3-(2-ethoxycarbonylethyl)ureido]-5H,10H-imidazo-[1,2-a]indeno[1,2-e]pyrazine-4-one, 8-[3-(2-carboxyethyl)ureido]-5H,10H-imidazo[1,2-a]-indeno[1,2-e]pyrazine-4-one, 8-[3-(4-fluorophenyl)ureido]-5H,10H-imidazo[1,2-a]-indeno[1,2-e]pyrazine-4-one, 8-[3-(3-fluorophenyl)ureido]-5H,10H-imidazo[1,2-a]-indeno[1,2-e]pyrazine-4-one, 8-[3-(2-fluorophenyl)ureido]-5H,10H-imidazo[1,2-a]-indeno[1,2-e]pyrazine-4-one, 8-(3-ethylureido)-5H,10H-imidazo[1,2-a]indeno[1,2-e]-pyrazine-4-one, 8-[3-morpholinoureido]-5H,10H-imidazo[1,2-a]indeno-[1,2-e]pyrazine-4-one, 10-amino-8-(3-methylureido)-5H,10H-imidazo[1,2-a]-indeno[1,2-e]pyrazine-4-one, 10-hydroxyimino-8-(3-methylureido)-5H,10H-imidazo-[1,2-a]indeno[1,2e-]pyrazine-4-one, and 8-(3-methylureido)-5H-imidazo[1,2-a]indeno[1,2-e]-pyrazine-4,10-dione and their salts.

4. A process for the preparation of a compound of formula (I) as defined in claim 1, in which $R_1$ and optionally $R_2$ represent an —NH—CONR$_9$R$_{12}$, —N(alk)CONR$_8$R$_9$, or —N(alk-Ar)CONR$_8$R$_9$ radical in which R$_9$ represents a hydrogen atom, R$_8$ represents a hydrogen atom or an optionally substituted phenylalkyl, an alkyl radical, an alk-COOR$_{21}$ radical or an optionally substituted phenyl radical and R$_{12}$ represents a hydrogen atom or an optionally substituted phenylalkyl, an alkyl radical, an -alk-COOR$_{21}$ radical or a substituted phenyl radical, which comprises the steps of reacting a compound of formula:

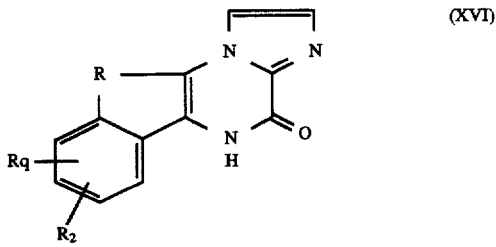

in which R and R$_2$ have the same meaning as recited in claim 1, and Rq represents an —NH$_2$, —NHalk or —NHalk-Ar radical, alk and Ar having the same meaning as recited in claim 1, with a derivative of formula Rs=C=N-Rt in which Rt represents an —Si(CH$_3$)$_3$, a benzoyl an alkyl radical, a phenylalkyl radical in which the phenyl ring is optionally substituted by one or a number of substituents selected from halogen atoms and alkyl, alkoxy, nitro, amino, hydroxyl, -alk-NH$_2$, carboxyl, cyano, —COOR$_{21}$ and -alk-COOR$_{21}$ radicals, an -alk-COOR$_{21}$ radical or a phenyl radical which is optionally substituted by one or a number of substituents selected from halogen atoms and alkyl, alkoxy, nitro, amino, hydroxyl, -alk-NH$_2$, carboxyl, cyano, —COOR$_{21}$ and -alk-COOR$_{21}$ radicals, in which alk and R$_{21}$ have the same meaning as recited in claim 1, and Rs represents an oxygen, isolating the product of said reaction and optionally converting said isolated product to a salt.

5. A process for the preparation of a compound of formula (I) as defined in claim 1, in which $R_1$ and optionally $R_2$ represent an —NHCSNR$_8$R$_9$ or —N(alk)CSNR$_8$R$_9$ radical in which R$_9$ represents a hydrogen atom, R$_8$ represents a hydrogen atom or an optionally substituted phenylalkyl, an alkyl radical, an alk-COOR$_{21}$ radical or an optionally substituted phenyl radical and R$_{12}$ represents a hydrogen atom or an optionally substituted phenylalkyl, an alkyl radical, an -alk-COOR$_{21}$ radical or a substituted phenyl radical, which comprises the steps of reacting a compound of formula:

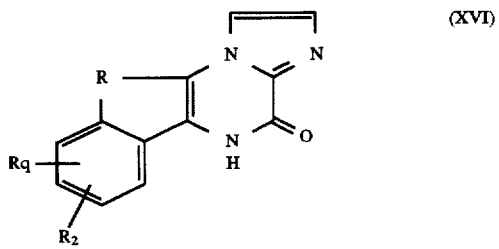

in which R and R$_2$ have the same meaning as recited in claim 1, and Rq represents an —NH$_2$ or —NHalk radical, alk having the same meaning as recited in claim 1, with a derivative of formula Rs=C=N-Rt in which Rt represents an —Si(CH$_3$)$_3$, a benzoyl, an alkyl radical, a phenylalkyl radical in which the phenyl ring is optionally substituted by one or a number of substituents selected from halogen atoms and alkyl, alkoxy, nitro, amino, hydroxyl, -alk-NH$_2$, carboxyl, cyano, —COOR$_{21}$ and -alk-COOR$_{21}$ radicals, an -alk-COOR$_{21}$ radical or a phenyl radical which is optionally substituted by one or a number of substituents selected from halogen atoms and alkyl, alkoxy, nitro, amino, hydroxyl, -alk-NH$_2$, carboxyl, cyano, —COOR$_{21}$ and -alk-COOR$_{21}$ radicals, in which alk and R$_{21}$ have the same meaning as recited in claim 1, and Rs represents a sulphur atom, isolating the product of said reaction and optionally converting said isolated product to a salt.

6. A compound of formula (I) according to claim 1, which said polyfluoroalkoxy radicals are trifluoromethoxy radicals.

7. A compound of formula (I) according to claim 1, in which R represents a C=R$_3$ radical, R$_1$ represents a hydroxyl, polyfluoroalkoxy, carboxyl, —NH—CHO, —N(alk)-CO—NR$_8$R$_9$, —NH—CO—NR$_9$R$_{12}$, —NH—CS—NR$_8$R$_9$, NH—CO—R$_{10}$, —NH—SO$_2$—NR$_7$R$_9$, —CO—NR$_7$R$_9$, —NH—SO$_2$-alk, —NR$_9$R$_{11}$, —S(O)$_m$-alk-Ar, —SO$_2$—NR$_7$R$_9$ or 2-oxo-1-imidazolidinyl radical, R$_2$ represents a hydrogen atom and R$_3$ represents an oxygen atom or an NOH radical, or an enantiomer, diastereoisomer, or salt thereof.

8. A compound of formula (I) according to claim 1, in which R represents a CH—R$_6$ radical, R$_1$ represents a hydroxyl, polyfluoroalkoxy, carboxyl, —NH—CHO, —N(alk)-CO—NR$_8$R$_9$, —NH—CO—NR$_9$R$_{12}$, —NH—CS—NR$_8$R$_9$, NH—CO—R$_{10}$, —NH—SO$_2$—NR$_7$R$_9$, —CO—NR$_7$R$_9$, —NH—SO$_2$-alk, —NR$_9$R$_{11}$, —S(O)$_m$-alk-Ar, —SO$_2$—NR$_7$R$_9$ or 2-oxo-1-imidazolidinyl radical, R$_2$ represents a hydrogen atom and R$_6$ represents a hydrogen atom radical or an —NR$_{14}$R$_{15}$ radical, or an enantiomer, diastereoisomer or salt thereof.

9. A compound of formula (I) according to claim 1, in which the R$_1$ substituent is in the 8- or 9-position.

* * * * *

UNITED STATES PATENT AND TRADEMARK OFFICE
CERTIFICATE OF CORRECTION

PATENT NO. : 5,789,406
DATED : August 4, 1998
INVENTOR(S) : Aloup et al.

It is certified that error appears in the above-identified patent and that said Letters Patent is hereby corrected as shown below:

Title Page, Item [75], in the Inventors, line 1, "Villeneuve le Roi" should read --Villeneuve-le-Roi--; line 2, "Charenton le Pont" should read -- Charenton-le-Pont--; and line 8, "Villemoisson Sur Orge" should read --Villemoisson-sur-Orge--.

Claim 1, column 65, line 41, "$COOR_{21}$, radicals" should read --$COOR_{21}$ radicals--.

Claim 1, column 65, line 54, "$R_1$" should read --$R_{19}$--.

Claim 3, column 67, line 32, "[1,2e-]" should read --[1,2-e]--.

Claim 4, column 67, line 60, after "benzoyl", insert --,--.

Claim 6, column 68, line 43, before "which", insert --in--.

Claim 9, column 68, line 65, after "$R_1$", delete ",".

Signed and Sealed this

Seventeenth Day of August, 1999

Attest:

Q. TODD DICKINSON

*Attesting Officer*   *Acting Commissioner of Patents and Trademarks*